(12) United States Patent
Zha et al.

(10) Patent No.: US 10,435,470 B2
(45) Date of Patent: Oct. 8, 2019

(54) ANTI-PD-L1 ANTIBODIES

(71) Applicant: CB Therapeutics, Inc., Santa Clara, CA (US)

(72) Inventors: Jiping Zha, Santa Clara, CA (US); Ziyong Sun, Santa Clara, CA (US); Junzhuan Qiu, Santa Clara, CA (US)

(73) Assignee: CB Therapeutics, Inc., Santa Clara, CA (US)

( * ) Notice: Subject to any disclaimer, the term of this patent is extended or adjusted under 35 U.S.C. 154(b) by 36 days.

(21) Appl. No.: 15/328,232

(22) PCT Filed: Aug. 5, 2015

(86) PCT No.: PCT/US2015/043723
§ 371 (c)(1),
(2) Date: Jan. 23, 2017

(87) PCT Pub. No.: WO2016/022630
PCT Pub. Date: Feb. 11, 2016

(65) Prior Publication Data
US 2017/0204184 A1    Jul. 20, 2017

(30) Foreign Application Priority Data

Aug. 5, 2014    (WO) ................ PCT/CN2014/083715

(51) Int. Cl.
*C07K 16/28* (2006.01)
*A61K 47/68* (2017.01)

(52) U.S. Cl.
CPC ...... *C07K 16/2827* (2013.01); *A61K 47/6849* (2017.08); *C07K 2317/24* (2013.01); *C07K 2317/565* (2013.01); *C07K 2317/74* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,225,539 A | 7/1993 | Winter |
| 5,624,821 A | 4/1997 | Winter et al. |
| 5,629,204 A | 5/1997 | Honjo et al. |
| 5,648,260 A | 7/1997 | Winter et al. |
| 5,698,520 A | 12/1997 | Honjo et al. |
| 5,994,514 A | 11/1999 | Jardieu et al. |
| 6,165,745 A | 12/2000 | Ward et al. |
| 6,194,551 B1 | 2/2001 | Idusogie et al. |
| 6,528,624 B1 | 3/2003 | Idusogie et al. |
| 6,632,927 B2 | 10/2003 | Adair et al. |
| 6,737,056 B1 | 5/2004 | Presta |
| 6,808,710 B1 | 10/2004 | Wood et al. |
| 6,936,704 B1 | 8/2005 | Freeman et al. |
| 7,029,674 B2 | 4/2006 | Carreno et al. |
| 7,038,013 B2 | 5/2006 | Freeman et al. |
| 7,101,550 B2 | 9/2006 | Wood et al. |
| 7,122,637 B2 | 10/2006 | Presta |
| 7,297,775 B2 | 11/2007 | Idusogie et al. |
| 7,317,091 B2 | 1/2008 | Lazar et al. |
| 7,332,581 B2 | 2/2008 | Presta |
| 7,335,742 B2 | 2/2008 | Presta |
| 7,355,008 B2 | 4/2008 | Stavenhagen et al. |
| 7,364,731 B2 | 4/2008 | Idusogie et al. |
| 7,371,826 B2 | 5/2008 | Presta |
| 7,414,171 B2 | 8/2008 | Honjo et al. |
| 7,416,726 B2 | 8/2008 | Ravetch |
| 7,488,802 B2 | 2/2009 | Collins et al. |
| 7,563,869 B2 | 7/2009 | Honjo et al. |
| 7,595,048 B2 | 9/2009 | Honjo et al. |
| 7,597,889 B1 | 10/2009 | Armour et al. |
| 7,608,429 B2 | 10/2009 | Reilly et al. |
| 7,635,757 B2 | 12/2009 | Freeman et al. |
| 7,638,492 B2 | 12/2009 | Wood et al. |
| 7,655,783 B2 | 2/2010 | Reilly et al. |
| 7,670,600 B2 | 3/2010 | Dall'Acqua et al. |
| 7,741,072 B2 | 6/2010 | Idusogie et al. |
| 7,790,858 B2 | 9/2010 | Presta |
| 7,851,598 B2 | 12/2010 | Davis |
| 7,863,419 B2 | 1/2011 | Taylor et al. |
| 7,943,743 B2 | 5/2011 | Korman et al. |
| 7,998,479 B2 | 8/2011 | Honjo et al. |
| 8,008,449 B2 | 8/2011 | Korman et al. |
| 8,088,905 B2 | 1/2012 | Collins et al. |
| 8,168,179 B2 | 5/2012 | Honjo et al. |
| 8,168,757 B2 | 5/2012 | Finnefrock et al. |
| 8,246,955 B2 | 8/2012 | Honjo et al. |

(Continued)

FOREIGN PATENT DOCUMENTS

| | | |
|---|---|---|
| AU | 2014201367 A1 | 4/2014 |
| CN | 1687135 A | 10/2005 |

(Continued)

OTHER PUBLICATIONS

Brown et al. (J Immunol. May 1996;156(9):3285-91 ).*
Vajdos et al. (J Mol Biol. Jul. 5, 2002;320(2):415-28).*
Agata et al., "Expression of the PD-1 antigen on the surface of stimulated mouse T and B lymphocytes." Int Immunol. (1996); 8(5): 765-772.
Ahmadzadeh, M. et al., "Tumor antigen-specific CD8 T cells infiltrating the tumor express high levels of PD-1 and are functionally impaired," Blood. Aug. 20, 2009;114(8):1537-1544. doi: 10.1182/blood-2008-12-195792. Epub May 7, 2009.
Amarnath, et al. "The PDL1-PD1 Axis Converts Human Th1 Cells Into Regulatory T Cells." Sci Transl Med. (2011); 3(111): 111ra120.
Araki, K. et al., "Programmed cell death 1-directed immunotherapy for enhancing T-cell function," Cold Spring Harbor Symposia on Quantitative Biology, vol. LXXVIII, 239-247 (2013).

(Continued)

*Primary Examiner* — Brian Gangle
(74) *Attorney, Agent, or Firm* — Cooley LLP

(57) ABSTRACT

The present disclosure relates to antibodies and antigen-binding fragments thereof that bind to PD-L1, and to methods of using such antibodies and antigen-binding fragments. For example, the present invention provides humanized anti-PD-L1 antibodies and methods of use thereof.

30 Claims, 19 Drawing Sheets

Specification includes a Sequence Listing.

(56) References Cited

U.S. PATENT DOCUMENTS

| | | | |
|---|---|---|---|
| 8,354,509 | B2 | 1/2013 | Carven et al. |
| 8,617,546 | B2 | 12/2013 | Kang et al. |
| 8,728,474 | B2 | 5/2014 | Honjo et al. |
| 8,735,553 | B1 | 5/2014 | Li et al. |
| 8,779,105 | B2 | 7/2014 | Korman et al. |
| 8,911,726 | B2 | 12/2014 | Takahashi et al. |
| 8,945,561 | B2 | 2/2015 | Davis |
| 9,067,999 | B1 | 6/2015 | Honjo et al. |
| 9,073,994 | B2 | 7/2015 | Honjo et al. |
| 9,084,776 | B2 | 7/2015 | Korman et al. |
| 9,139,653 | B1 | 9/2015 | Campbell et al. |
| 9,217,034 | B2 | 12/2015 | Li et al. |
| 9,492,540 | B2 | 11/2016 | Korman et al. |
| 9,834,606 | B2 | 12/2017 | Li et al. |
| 9,988,450 | B2 | 6/2018 | Li et al. |
| 2004/0038339 | A1 | 2/2004 | Kufer et al. |
| 2005/0064514 | A1 | 3/2005 | Stavenhagen et al. |
| 2005/0202028 | A1 | 9/2005 | Ledbetter et al. |
| 2006/0121032 | A1 | 6/2006 | Dahiyat et al. |
| 2006/0134105 | A1 | 6/2006 | Lazar et al. |
| 2006/0263856 | A1 | 11/2006 | Gillies et al. |
| 2007/0160597 | A1 | 7/2007 | Lazar et al. |
| 2008/0227704 | A1 | 9/2008 | Kamens et al. |
| 2009/0068175 | A1 | 3/2009 | Lazar et al. |
| 2009/0155256 | A1 | 6/2009 | Black et al. |
| 2009/0217401 | A1 | 8/2009 | Korman et al. |
| 2010/0151492 | A1 | 6/2010 | Ahmed et al. |
| 2010/0197924 | A1 | 8/2010 | Gould et al. |
| 2010/0278832 | A1 | 11/2010 | Kamogawa et al. |
| 2010/0317834 | A1 | 12/2010 | Lazar et al. |
| 2011/0008369 | A1 | 1/2011 | Finnefrock et al. |
| 2011/0052584 | A1 | 3/2011 | Ravetch |
| 2011/0054151 | A1 | 3/2011 | Lazar et al. |
| 2011/0159023 | A1 | 6/2011 | Langermann |
| 2011/0171215 | A1 | 7/2011 | Davis et al. |
| 2011/0171220 | A1 | 7/2011 | Davis et al. |
| 2011/0177088 | A1 | 7/2011 | Olive et al. |
| 2011/0195068 | A1 | 8/2011 | Langermann et al. |
| 2011/0271358 | A1 | 11/2011 | Freeman et al. |
| 2011/0287032 | A1 | 11/2011 | Lazar et al. |
| 2012/0076726 | A1 | 3/2012 | Gellerfors et al. |
| 2012/0251531 | A1 | 10/2012 | Baehner et al. |
| 2013/0004514 | A1 | 1/2013 | Zahn et al. |
| 2013/0089541 | A1 | 4/2013 | D'Angelo et al. |
| 2013/0133091 | A1 | 5/2013 | Korman et al. |
| 2013/0259868 | A1 | 10/2013 | Roschke et al. |
| 2013/0291136 | A1 | 10/2013 | Freeman et al. |
| 2013/0309250 | A1 | 11/2013 | Cogswell et al. |
| 2014/0044738 | A1 | 2/2014 | Langermann et al. |
| 2014/0162316 | A1 | 6/2014 | O'Neil et al. |
| 2014/0243504 | A1 | 8/2014 | Davis et al. |
| 2014/0245468 | A1 | 8/2014 | McWhirter et al. |
| 2014/0271642 | A1 | 9/2014 | Murphy et al. |
| 2014/0314714 | A1 | 10/2014 | Honjo et al. |
| 2014/0341902 | A1 | 11/2014 | Maecker et al. |
| 2014/0356363 | A1 | 12/2014 | Zhou et al. |
| 2014/0377269 | A1 | 12/2014 | Mabry et al. |
| 2015/0044231 | A1 | 2/2015 | Kjaergaard et al. |
| 2015/0125444 | A1 | 5/2015 | Tsui et al. |
| 2015/0210763 | A1 | 7/2015 | Kuramochi et al. |
| 2015/0315274 | A1 | 11/2015 | Li et al. |
| 2015/0337053 | A1 | 11/2015 | McCarthy et al. |
| 2015/0353631 | A1 | 12/2015 | Buttini et al. |
| 2017/0044260 | A1 | 2/2017 | Baruah et al. |
| 2017/0267762 | A1 | 9/2017 | Qiu et al. |
| 2018/0111995 | A1 | 4/2018 | Li et al. |
| 2018/0215825 | A1 | 8/2018 | Li et al. |
| 2018/0251551 | A1 | 9/2018 | Li et al. |

FOREIGN PATENT DOCUMENTS

| | | |
|---|---|---|
| CN | 101104640 A | 1/2008 |
| CN | 101899114 A | 12/2010 |
| RU | 2478400 C2 | 4/2013 |
| WO | WO 1994/029351 | 12/1994 |
| WO | WO 2005/077981 | 8/2005 |
| WO | WO 2006/084015 | 8/2006 |
| WO | WO 2006/121168 | 11/2006 |
| WO | WO 2007/005874 | 1/2007 |
| WO | WO 2007/064972 | 6/2007 |
| WO | WO 2007/067444 | 6/2007 |
| WO | WO 2007/136572 | 11/2007 |
| WO | WO 2008/008315 | 1/2008 |
| WO | WO 2008/083174 A2 | 7/2008 |
| WO | WO 2008/145142 | 12/2008 |
| WO | WO 2008/156712 | 12/2008 |
| WO | WO 2010/036959 | 4/2010 |
| WO | WO 2010/089411 | 8/2010 |
| WO | WO 2010/104949 | 9/2010 |
| WO | WO 2011/110604 A1 | 9/2011 |
| WO | WO 2012/135408 | 10/2012 |
| WO | WO 2012/145493 | 10/2012 |
| WO | WO 2013/079174 | 6/2013 |
| WO | WO 2013/173223 | 11/2013 |
| WO | WO 2013/181452 | 12/2013 |
| WO | WO 2013/181634 | 12/2013 |
| WO | WO 2014/022758 | 2/2014 |
| WO | WO 2014/055897 | 4/2014 |
| WO | WO 2014/066834 | 5/2014 |
| WO | WO 2014/100079 | 6/2014 |
| WO | WO 2015/035606 | 3/2015 |
| WO | WO 2016/000619 | 1/2016 |
| WO | WO 2016/014688 | 1/2016 |
| WO | WO 2016/022630 | 2/2016 |
| WO | WO 2017/011580 A2 | 1/2017 |

OTHER PUBLICATIONS

Arlauckas, S.P. et al., "In vivo imaging reveals a tumor-associated macrophage-mediated resistance pathway in anti-PD-1 therapy," Sci. Transl. Med., 9, eaal3604 (May 2017).

Barber, et al. "Restoring function in exhausted CD8 T cells during chronic viral infection." Nature (2006); 439.7077: 682.

Bennett, et al. "Program death-1 engagement upon TCR activation has distinct effects on costimulation and cytokine-driven proliferation: attenuation of ICOS, IL-4, and IL-21, but not CD28, IL-7, and IL-15 responses." The Journal of Immunology (2003); 170(2): 711-718.

Berger, R. et al., "Phase I safety and pharmacokinetic study of CT-011, a humanized antibody interacting with PD-1, in patients with advanced hematologic malignancies," Clinical Cancer Research (2008); 14(10): 3044-3051.

Blank et al. "Blockade of PD-L1 (B7-H1) augments human tumor-specific T cell responses in vitro." International Journal of Cancer (2006); 119(2): 317-327.

Blank, et al. "Interaction of PD-L1 on tumor cells with PD-1 on tumor-specific T cells as a mechanism of immune evasion: implications for tumor immunotherapy." Cancer Immunology, Immunotherapy (2005); 54(4): 307-314.

Brahmer, J. R. et al., "Phase I study of single-agent anti-programmed death-1 (MDX-1106) in refractory solid tumors: safety, clinical activity, pharmacodynamics, and immunologic correlates," J Clin Oncol. (2010); 28(19): 3167-3175.

Brahmer, J. R. et al., "Safety and Activity of Anti-PD-L1 Antibody in Patients with Advanced Cancer," N Engl J Med. (Jun. 28, 2012), 366(26):2455-2465.

Brown, et al. "Blockade of programmed death-1 ligands on dendritic cells enhances T cell activation and cytokine production." The Journal of Immunology (2003); 170(3): 1257-1266.

Carter, et al. "PD-1: PD-L inhibitory pathway affects both CD4+ and CD8+T cells and is overcome by IL-2." European Journal of Immunology (2002); 32(3): 634-643.

Chemnitz, et al. "SHP-1 and SHP-2 associate with immunoreceptor tyrosine-based switch motif of programmed death 1 upon primary human T cell stimulation, but only receptor ligation prevents T cell activation." The Journal of Immunology (2004); 173(2): 945-954.

Chia-Jui, Y. et al., Abstract of "Preliminary results of a phase 1A/1B study of BGB-A317, an anti-PD-1 monoclonal antibody (mAb), in patients with advanced hepatocellular carcinoma (HCC)," Annals of Oncology (2017).

(56) References Cited

OTHER PUBLICATIONS

Clynes, R. A. et al., "Inhibitory Fc receptors modulate in vivo cytoxicity against tumor targets," Nat. Med. 6(4):443-446 (Apr. 2000).

Dahan, R. et al., "FcγRs Modulate the Anti-tumor Activity of Antibodies Targeting the PD-1/PD-L1 Axis," Cancer Cell. Sep. 14, 2015;28(3):285-95. doi: 10.1016/j.ccell.2015.08.004.

Datta-Mannan, et al. "Humanized IgG1 variants with differential binding properties to the neonatal Fc receptor: relationship to pharmacokinetics in mice and primates." Drug Metab Dispos. (2007); 35(1): 86-94.

Dong, et al. "B7-H1 pathway and its role in the evasion of tumor immunity." Journal of Molecular Medicine (2003); 81(5): 281-287.

Dong, et al. "Tumor-associated B7-H1 promotes T-cell apoptosis: a potential mechanism of immune evasion." Nature Medicine (2002); 8(8): 793-800.

Dorfman, D. M. et al., "Programmed death-1 (PD-1) is a marker of germinal center-associated T Cells and angioimmunoblastic T-cell lymphoma," American Journal of Surgical Pathology (2006); 30(7): 802-810.

European Search Report for European Application No. 16167542.6, dated Nov. 14, 2016, 5 pages.

Fife, et al. "Interactions between PD-1 and PD-L1 promote tolerance by blocking the TCR-induced stop signal." Nature Immunolog (2009); 10(11): 1185-1192.

Francisco, et al. "PD-L1 regulates the development, maintenance, and function of induced regulatory T cells." Journal of Experimental Medicine (2009); 206(13): 3015-3029.

Freeman, et al. "Engagement of the PD-1 immunoinhibitory receptor by a novel B7 family member leads to negative regulation of lymphocyte activation." Journal of Experimental Medicine (2000); 192(7): 1027-1034.

Fuller, M. J. et al., "Immunotherapy of chronic hepatitis C virus infection with antibodies against programmed cell death-1 (PD-1)," Proceedings of the National Academy of Sciences (2013); 110(37):15001-15006.

Gelderman, K. A. et al., "Complement function in mAb-mediated cancer immunotherapy," Trends in Immunology (2004); 25(3): 158-164.

Graziani, et al., "Ipilimumab: A novel immunostimulatory monoclonal antibody for the treatment of cancer." Pharmacological Research (2012); 65(1): 9-22.

Hamid, O. et al., "Safety and tumor responses with lambrolizumab (Anti-PD-1) in melanoma," New England Journal of Medicine (2013); 369(2): 134-144.

Hofmeyer, et al. "The PD-1/PD-L1 (B7-H1) pathway in chronic infection-induced cytotoxic T lymphocyte exhaustion." BioMed Research International (2011); vol. 2011, Article ID 451694, 9 pages.

Idusogie, et al. "Mapping of the C1q binding site on rituxan, a chimeric antibody with a human IgG1 Fc." The Journal of Immunology (2000); 164(8): 4178-4184.

International Search Report and Written Opinion for International Application No. PCT/CN2013/083467, dated Jun. 16, 2014, 9 pages.

International Search Report and Written Opinion for International Application No. PCT/CN2015/083066, dated Sep. 24, 2015, 8 pages.

International Preliminary Report on Patentability for International Application No. PCT/US2015/041575, dated Jan. 24, 2017, 8 pages.

International Search Report and Written Opinion for International Application No. PCT/US2015/041575, dated Jan. 6, 2016, 12 pages.

International Preliminary Report on Patentability for International Application No. PCT/US2015/043723, dated Feb. 7, 2017, 9 pages.

International Search Report and Written Opinion for International Application No. PCT/US2015/043723, dated Jan. 6, 2016, 14 pages.

InvivoGen Insight, "IgG-Fc Engineering for Therapeutic Use," Apr./May 2006, 4 pages.

Iwai, et al. "Involvement of PD-L1 on tumor cells in the escape from host immune system and tumor immunotherapy by PD-L1 blockade." Proceedings of the National Academy of Sciences (2002); 99(19): 12293-12297.

James, L. K. et al., "Potential Mechanisms for IgG4 Inhibition of Immediate Hypersensitivity Reactions," Curr Allergy Asthma Rep. 2016; 16: 23. Published online Feb. 18, 2016. doi: 10.1007/s11882-016-0600-2.

Jiao, Yu et al., "Advances in the research of the anti-cancer agent—Raf kinase inhibitor," Strait Pharmaceutical Journal, vol. 19, No. 8, 2007, pp. 1-5 (with English Abstract).

Kettleborough, et al. "Optimization of primers for cloning libraries of mouse immunoglobulin genes using the polymerase chain reaction." European Journal of Immunology (1993); 23(1): 206-211.

Konishi, et al. "B7-H1 expression on non-small cell lung cancer cells and its relationship with tumor-infiltrating lymphocytes and their PD-1 expression." Clinical Cancer Research (2004); 10(15): 5094-5100.

Latchman, et al. "PD-L1-deficient mice show that PD-L1 on T cells, antigen-presenting cells, and host tissues negatively regulates T cells." Proceedings of the National Academy of Sciences of the United States of America (2004); 101(29): 10691-10696.

Latchman, Yvette, et al. "PD-L2 is a second ligand for PD-1 and inhibits T cell activation." Nature immunology (2001); 2(3): 261.

Lee, et al. "Blocking the monocyte chemoattractant protein-1/CCR2 chemokine pathway induces permanent survival of islet allografts through a programmed death-1 ligand-1-dependent mechanism." The Journal of Immunology (2003); 171(12): 6929-6935.

Lund, J. et al., "Multiple interactions of IgG with its core oligosaccharide can modulate recognition by complement and human Fc gamma receptor I and influence the synthesis of its oligosaccharide chains," J Immunol. (1996); 157(11): 4963-4969.

Medzihradszky, et al. "Characterization of site-specific N-glycosylation." Methods Mol Biol. (2008); 446: 293-316.

Moore, et al. "Engineered Fc variant antibodies with enhanced ability to recruit complement and mediate effector functions." MAbs. (2010); 2(2): 181-189.

Mueller, et al. "PD-L1 has distinct functions in hematopoietic and nonhematopoietic cells in regulating T cell responses during chronic infection in mice." The Journal of Clinical Investigation (2010); 120(7): 2508-2515.

Nomi, et al. "Clinical significance and therapeutic potential of the programmed death-1 ligand/programmed death-1 pathway in human pancreatic cancer." Clinical Cancer Research (2007); 13(7): 2151-2157.

Office Action for U.S. Appl. No. 14/736,966, dated Jun. 1, 2017, 18 pages.

Okazaki, et al. "New regulatory co-receptors: inducible co-stimulator and PD-1." Current Opinion in Immunology (2002); 14(6): 779-782.

Okazaki, et al. "PD-1 and PD-1 ligands: from discovery to clinical application." International Immunology (2007); 19(7): 813-824.

Panka, D. J. et al., "Variable region framework differences result in decreased or increased affinity of variant anti-digoxin antibodies," Proc. Natl. Acad. Sci. USA (1988); 85: 3080-3084.

Partial Search Report for European Application No. 15829791.1 dated Nov. 23, 2017, 12 pages.

Presta, L. G. et al., "Engineering therapeutic antibodies for improved function," Biochemical Society Transactions (2002); 30(4): 487-490.

Rudikoff, S. et al., "Single amino acid substitution altering antigen-binding specificity," Proc. Natl. Acad. Sci. USA (1982); 79: 1979-1983.

Sequence Alignment, 2014, 1 page.

Shields, R. L. et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry (2001); 276(9): 6591-6604.

Smith, K. G. et al., "FcγRIIB in autoimmunity and infection: evolutionary and therapeutic implications," Nat Rev Immunol. (2010); 10(5): 328-343.

(56) References Cited

OTHER PUBLICATIONS

Spiekermann, et al. "Receptor-mediated immunoglobulin G transport across mucosal barriers in adult life." Journal of Experimental Medicine (2002); 196(3): 303-310.
Stave, J. W. et al., "Antibody and antigen contact residues define epitope and paratope size and structure," The Journal of Immunology (2013); 191: 1428-1435.
Strebe, et al. "Cloning of variable domains from mouse hybridoma by PCR." Antibody Engineering (2010):3-14.
Strome, et al. "B7-H1 blockade augments adoptive T-cell immunotherapy for squamous cell carcinoma." Cancer Research (2003); 63(19): 6501-6505.
Supplementary Partial European Search Report for European Application No. 13893636.4, dated Feb. 28, 2017, 13 pages.
Supplementary European Search Report for European Application No. 15824277.6 dated Dec. 15, 2017, 11 pages.
Sznol, M. et al., "Antagonist antibodies to PD-1 and B7-H1 (PD-L1) in the treatment of advanced human cancer," Clinical Cancer Research (2013); 19(5): 1021-1034.
Tai, et al. "Potent in vitro and in vivo activity of an Fc-engineered humanized anti-HM1. 24 antibody against multiple myeloma via augmented effector function." Blood (2012); 119(9): 2074-2082.
Thompson, et al. "PD-1 is expressed by tumor-infiltrating immune cells and is associated with poor outcome for patients with renal cell carcinoma." Clinical Cancer Research (2007); 13(6): 1757-1761.
Thompson, et al. "Tumor B7-H1 is associated with poor prognosis in renal cell carcinoma patients with long-term follow-up." Cancer Research (2006); 66(7): 3381-3385.
Tsushima, et al. "Predominant expression of B7-H1 and its immunoregulatory roles in oral squamous cell carcinoma." Oral Oncology (2006); 42(3): 268-274.
KOIZ16, UniProtKB Accession No. KOIZ16, Uncharacterized protein, Dec. 11, 2013 1-3 [online]. [Retrieved on Nov. 2, 2015]. Retrieved from the internet <URL: http://www.uniprot.org/uniprot/KOIZ 16.txt?version= 10> Entire document, 1 page.
Wang, C. et al., "In Vitro Characterization of the Anti-PD-1 Antibody Nivolumab, BMS-936558, and in Vivo Toxicology in Non-Human Primates," Cancer Immunol Res (2014); 2(9): 846-856.
Wherry, E. J., "T cell exhaustion," Nature Immunology 12(6):492-499 (2011). Published online May 18, 2011.
Wintterle, et al. "Expression of the B7-Related Molecule B7-H1 by Glioma Cells." Cancer Research (2003); 63(21): 7462-7467.
Wong, et al. "Programmed death-1 blockade enhances expansion and functional capacity of human melanoma antigen-specific CTLs." International Immunology(2007); 19(10): 1223-1234.
Wu, H. et al., "Humanization of a murine monoclonal antibody by simultaneous optimization of framework and CDR residues," Journal of Molecular Biology, 294(1):151-162 (Nov. 1999).
Xu, D. et al., "In vitro characterization of five humanized OKT3 effector function variant antibodies," Cell Immunol. (2000); 200(1): 16-26.

Office Action for European Application No. 15824277.6, dated Nov. 2, 2018, 6 pages.
Extended European Search Report for European Application No. 15829791.1 dated Mar. 28, 2018, 17 pages.
Abdiche, et al., "Assessing kinetic and epitopic diversity across orthogonal monoclonal antibody generation platforms." mABs (Feb.-Mar. 2016); 8(2): 264-277.
Boyd and Crowe Jr., "Deep sequencing and human antibody repertoire analysis." Current Opinion in Immunology (Jun. 2016); 40: 103-109. Epub Apr. 8, 2016.
Conroy, et al., "Antibodies: From novel repertoires to defining and refining the structure of biologically important targets." Methods (Mar. 2017); 116: 12-22. Epub Jan. 11, 2017.
Damschroder, et al., "Analysis of human and primate CD2 molecules by protein sequence and epitope mapping with anti-human CD2 antibodies." Mol Immunol. (Aug. 2004); 41(10): 985-1000.
Ferrara, et al., "Recombinant renewable polyclonal antibodies." mABs (2015); 7(1): 32-41.
Khan, et al., "Cross-neutralizing anti-HIV-1 human single chain variable fragments (scFvs) against CD4 binding site and N332 glycan identified from a recombinant phage library." Scientific Reports (2017); Article No. 45163, 12 pages.
Könitzer, et al., "Generation of a highly diverse panel of antagonistic chicken monoclonal antibodies against the GIP receptor." mABs (Apr. 2017); 9(3): 536-549. Epub Jan. 5, 2017.
Lee, et al., "Molecular-level analysis of the serum antibody repertoire in young adults before and after seasonal influenza vaccination." Nat Med. (Dec. 2016); 22(12): 1456-1464. Epub Nov. 7, 2016.
Parola, et al., "Integrating high-throughput screening and sequencing for monoclonal antibody discovery and engineering." Immunology (Jan. 2018); 153(1): 31-41. Epub Oct. 30, 2017.
Roitt, et al., "Antibody Specificity and Affinity". Immunology, Moscow, 2000, Publishing House "Mir", p. 153 (with English summary/abstract of pertinent p. 153), 594 pages.
Sheehan and Marasco, "Phage and Yeast Display." Microbial. Spectr. (2015); 3(1): AID-0028-2014; 17 pages.
Van Regenmortel, Marc H. V., "Development of a Preventive HIV Vaccine Requires Solving Inverse Problems Which Is Unattainable by Rational Vaccine Design." Front Immunol. (Jan. 2018); 8: 2009. eCollection 2017.
Zhou, et al., "Structural Repertoire of HIV-1-Neutralizing Antibodies Targeting the CD4 Supersite in 14 Donors." Cell (Jun. 2015); 161(6): 1280-1292.
Invitation to Pay Additional Fees for International Application No. PCT/US2015/041575, dated Oct. 30, 2015, 3 pages.
Invitation to Pay Additional Fees for International Application No. PCT/US2015/043723, dated Oct. 30, 2015, 3 pages.
Köhler, G., "Immunoglobulin chain loss in hybridoma lines." Proc Natl Acad Sci USA (Apr. 1980); 77(4): 2197-2199.
Ozturk and Palsson, "Loss of antibody productivity during long-term cultivation of a hybridoma cell line in low serum and serum-free media." Hybridoma (Apr. 1990); 9(2): 167-175.

\* cited by examiner

Figure 3
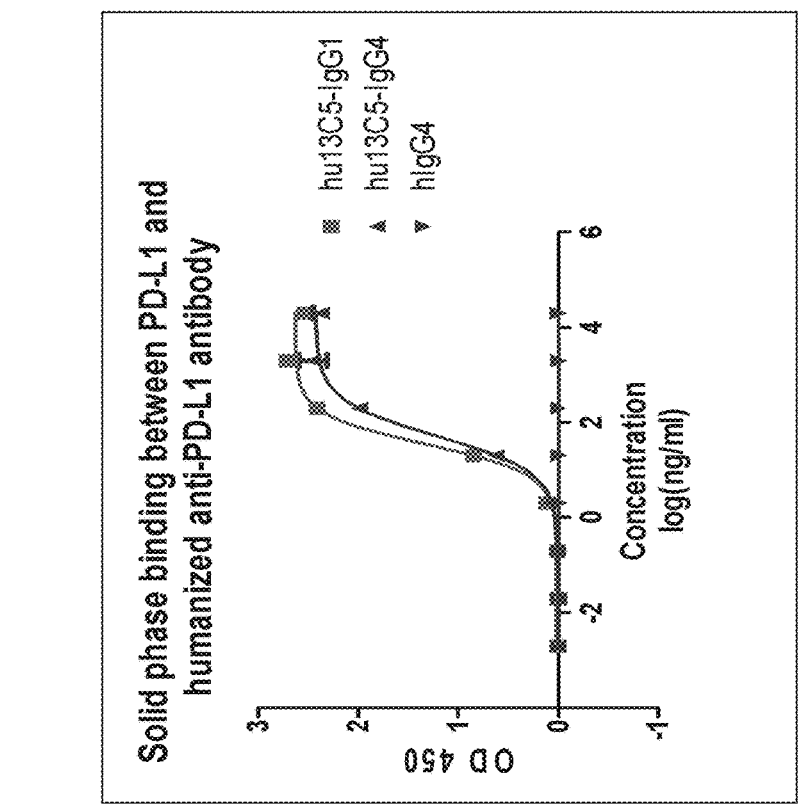
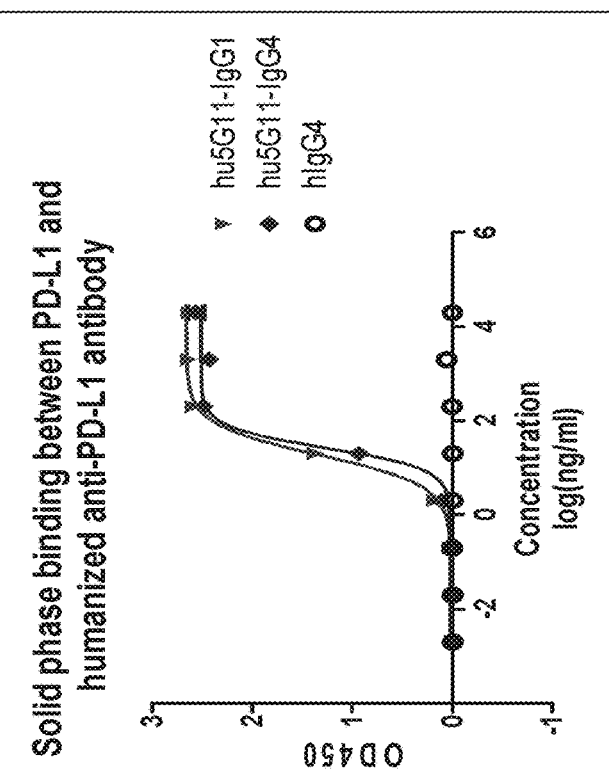

Figure 7
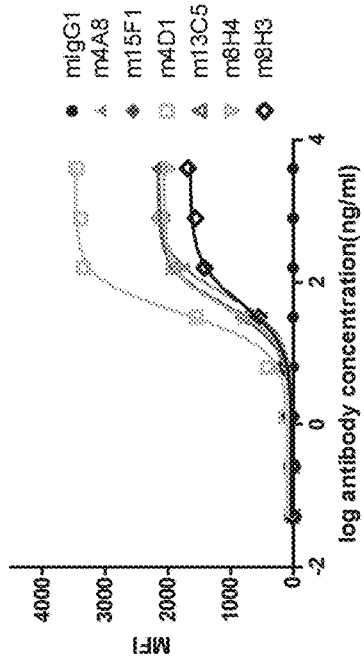
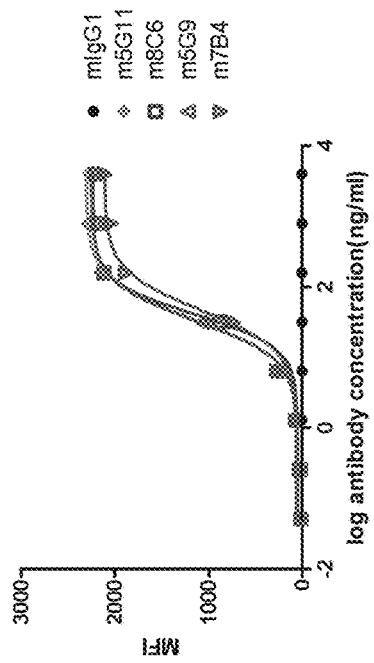

ANTI-PD-L1 ANTIBODIES

CROSS-REFERENCE TO RELATED APPLICATIONS

This application is a U.S. National Stage of International Application No. PCT/US2015/043723, filed Aug. 5, 2015, which claims priority to International Application No. PCT/CN2014/083715, filed Aug. 5, 2014, each of which is incorporated herein by reference in its entirety for all purposes.

FIELD OF THE INVENTION

The present invention relates to antibodies and antigen-binding fragments thereof that bind to PD-L1, and to methods of using such antibodies and antigen-binding fragments.

DESCRIPTION OF THE TEXT FILE SUBMITTED ELECTRONICALLY

The content of the text file submitted electronically herewith is incorporated herein by reference in its entirety: A computer readable format copy of the Sequence Listing (filename: CRBI_007_01WO_SeqList_ST25.txt); date recorded: Aug. 4, 2015; file size 153 KB).

BACKGROUND

Programmed death receptor Ligand 1 (PD-L1) is a ligand of programmed death receptor 1 (PD-1). PD-1 is primarily expressed on lymphocytes and has two ligands, PD-L1 and PD-L2. PD-L2 is not as common as PD-L1. PD-L1 is also known as cluster of differentiation 274 (CD274) or B7 homolog 1 (B7-H1) and is a 40 kDa type 1 transmembrane protein which is encoded by the CD274 gene. Both PD-L1 and PD-1 belong to immunoglobulin superfamily and consist of two extracellular Ig domains, an N-terminal V domain, and a C-terminal constant domain. The binding interface of PD-L1 to programmed death 1 (PD-1) and B7-1 (CD80) is on the IgV-like domain (Lin et al. (2008) PNAS 105:3011-3016). While PD-L1 contains a conserved short intracellular tail (about 30 amino acids), PD-1 contains two cytoplasmic tyrosine-based signaling motifs, an immunoreceptor tyrosine-based inhibition motif (ITIM) and an immunoreceptor tyrosine-based switch motif (ITSM). Following T cell stimulation, PD-1 recruits the tyrosine phosphatase SHP-2 to the ITSM motif within its cytoplasmic tail, leading to the dephosphorylation of effector molecules such as CD3 Zeta, PKC theta and ZAP70 that are involved in the CD3 T cell signaling cascade (Freeman et al. (2000) J Exp Med 192:1027-34; Latchman, et. al. (2001) Nat Immunol 2:261-8; Carter et al. (2002) Eur J Immunol 32:634-43).

PD-L1 is not only widely distributed on leukocytes and nonhematopoietic cells in lymphoid and nonlymphoid tissues, but also in various cancer cells. Clinical data suggest that high tumor expression of PD-L1 is associated with increased tumor aggressiveness and poorer prognosis. The formation of PD-1/PD-L1 complex transmits an inhibitory signal and negatively regulates T cell immune responses; it inhibits TCR-mediated T cell activation, cytokine production and T cell proliferation (Fife et al. (2011) Nature Immunology 10:1185-1193); induces exhaustion or anergy among cognate antigen-specific T cells (Hofmeyer et al. (2011) Journal of Biomedicine and Biotechnology 2011:1-9); promotes the differentiation of TH1 cells into Foxp3+ regulatory T cells (Armanath et al. (2011) Science TransMed 3:1-13; Francisco et al. (2009) J. Exp. Med. 206:3015-3029); and induces apoptosis of effctor T cells. Disruption of the PD-L1 gene leads to up-regulated T cell responses and the generation of self-reactive T cells (Latchman et al. (2004) PNAS 101:10691-10696). Antibody blockade of either PD-1 or PD-L1 leads to increased antitumor immunity (Iwai et al. (2002) PNAS 99:12293-12297).

Thus, there is an important role for the PD-1/PD-L1 pathway in controlling immune responses. Dysfunction of PD-1/PD-L1 signaling appears to be correlated with initiation and development of diseases such as cancer and viral infection. Analysis of knockout animals has led to the understanding that PD-1/PD-L1 functions mainly in inducing and regulating peripheral tolerance. Thus, therapeutic blockade of the PD-1/PD-L1 pathway would be helpful in overcoming immune tolerance and in the treatment of cancer or infection as well as in boosting immunity during vaccination (either prophylactic or therapeutic). There is a need in the art for improved methods for blocking the PD-1/PD-L1 pathway.

SUMMARY OF THE INVENTION

In one aspect, the present invention provides antibodies and antigen-binding fragments thereof that bind to programmed death-1 ligand 1(PD-L1). In some embodiments, the antibodies and antigen-binding fragments thereof bind to human PD-L1. In some embodiments, the antibodies and antigen-binding fragments thereof bind to PD-L1 and block binding of PD-1 and/or CD80 to PD-L1. In further embodiments, the anti-PD-L1 antibodies and fragments thereof bind to PD-L1 and disrupt the PD-L1/PD-1 or PD-L1/CD80 pathway. In one embodiment, the antibody or fragment thereof is a murine antibody, a chimeric antibody, a human antibody or a humanized antibody. In one embodiment, the anti-PD-L1 antibody or fragment thereof is a monoclonal antibody, scFv, Fab fragment, Fab' fragment, F(ab)' fragment, bispecific antibody, immunoconjugate, or a combination thereof In one embodiment, the present invention provides an isolated antibody or fragment thereof comprising one or more CDRs selected from the group consisting of SEQ ID NOs: 81-140.

In one embodiment, the antibody or fragment thereof comprises a heavy chain CDR1 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 81, 87, 93, 99, 105, 111, 117, 123, 129, and 135.

In one embodiment, the antibody or fragment thereof comprises a heavy chain CDR2 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 82, 88, 94, 100, 106, 112, 118, 124, 130, and 136.

In one embodiment, the antibody or fragment thereof comprises a heavy chain CDR3 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 83, 89, 95, 101, 107, 113, 119, 125, 131, and 137.

In one embodiment, the antibody or fragment thereof comprises a light chain CDR1 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 84, 90, 96, 102, 108, 114, 120, 126, 132, and 138.

In one embodiment, the antibody or fragment thereof comprises a light chain CDR2 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 85, 91, 97, 103, 109, 115, 121, 127, 133, and 139.

In one embodiment, the antibody or fragment thereof comprises a light chain CDR3 sequence having at least 80% homology, at least 81% homology, at least 82% homology, at least 83% homology, at least 84% homology, at least 85% homology, at least 86% homology, at least 87% homology, at least 88% homology, at least 89% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 86, 92, 98, 104, 110, 116, 122, 128, 134, and 140.

In one embodiment, the antibody or fragment thereof comprises a heavy chain CDR1 consisting of an amino acid sequence selected from the group consisting of SEQ ID NOs: 81, 87, 93, 99, 105, 111, 117, 123, 129, and 135; a heavy chain CDR2 consisting of an amino acid sequence selected from the group consisting of SEQ ID NOs: 82, 88, 94, 100, 106, 112, 118, 124, 130, and 136; a heavy chain CDR3 consisting of an amino acid sequences selected from the group consisting of SEQ ID NOs: 83, 89, 95, 101, 107, 113, 119, 125, 131, and 137; a light chain CDR1 consisting of an amino acid sequence selected from the group consisting of SEQ ID NOs: 84, 90, 96, 102, 108, 114, 120, 126, 132, and 138; a light chain CDR2 consisting of an amino acid sequence selected from the group consisting of SEQ ID NOs: 85, 91, 97, 103, 109, 115, 121, 127, 133, and 139 and a light chain CDR3 consisting of an amino acid sequence selected from the group consisting of SEQ ID NOs: 86, 92, 98, 104, 110, 116, 122, 128, 134, and 140.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 81, 82, and 83, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 84, 85, and 86, respectively. In a further embodiment, the antibody or antibody fragment thereof comprises a heavy chain CDR1, CDR2, and CDR3 according to SEQ ID NOs: 81, 82, and 83, respectively, and a light chain CDR1, CDR2, and CDR3 according to SEQ ID NOs: 84, 85, and 86, respectively.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 87, 88, and 89, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 90, 91, and 92, respectively. In a further embodiment, the antibody or antibody fragment thereof comprises a heavy chain CDR1, CDR2, and CDR3 according to SEQ ID NOs: 87, 88, and 89, respectively, and a light chain CDR1, CDR2, and CDR3 according to SEQ ID NOs: 90, 91, and 92, respectively.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 93, 94, and 95, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 96, 97, and 98, respectively. In a further embodiment, the antibody or antibody fragment thereof comprises a heavy chain CDR1, CDR2, and CDR3 according to SEQ ID NOs: 93, 94, and 95, respectively, and a light chain CDR1, CDR2, and CDR3 according to SEQ ID NOs: 96, 97, and 98, respectively.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 99, 100, and 101, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 102, 103, and 104, respectively. In a further embodiment, the antibody or antibody fragment thereof comprises a heavy chain CDR1, CDR2, and CDR3 according to SEQ ID NOs: 99, 100, and 101, respectively, and a light chain CDR1, CDR2, and CDR3 according to SEQ ID NOs: 102, 103, and 104, respectively.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 105, 106, and 107, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 108, 109, and 110, respectively. In a further embodiment, the antibody or antibody fragment thereof comprises a heavy chain CDR1, CDR2, and CDR3 according to SEQ ID NOs: 105, 106, and 107, respectively, and a light chain CDR1, CDR2, and CDR3 according to SEQ ID NOs: 108, 109, and 110, respectively.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 111, 112, and 113, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 114, 115, and 116, respectively. In a further embodiment, the antibody or antibody fragment thereof comprises a heavy chain CDR1, CDR2, and CDR3 according to SEQ ID NOs: 111, 112, and 113, respectively, and a light chain CDR1, CDR2, and CDR3 according to SEQ ID NOs: 114, 115, and 116, respectively.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 117, 118, and 119, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 120, 121, and 122, respectively. In a further embodiment, the antibody or antibody fragment thereof comprises a heavy chain CDR1, CDR2, and CDR3 according to SEQ ID NOs: 117, 118, and 119, respectively, and a light chain CDR1, CDR2, and CDR3 according to SEQ ID NOs: 120, 121, and 122, respectively.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 123, 124, and 125, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 126, 127, and 128, respectively. In a further embodiment, the antibody or antibody fragment thereof comprises a heavy chain CDR1, CDR2, and CDR3 according to SEQ ID NOs: 123, 124, and 125, respectively, and a light chain CDR1, CDR2, and CDR3 according to SEQ ID NOs: 126, 127, and 128, respectively.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 129, 130, and 131, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 132, 133, and 134, respectively. In a further embodiment, the antibody or antibody fragment thereof comprises a heavy chain CDR1, CDR2, and CDR3 according to SEQ ID NOs: 129, 130, and 131, respectively, and a light chain CDR1, CDR2, and CDR3 according to SEQ ID NOs: 132, 133, and 134, respectively.

In one embodiment, the antibody or fragment thereof binds PD-L1 and comprises a heavy chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 135, 136, and 137, respectively; and a light chain CDR1, CDR2, and CDR3 comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence according to SEQ ID NOs: 138, 139, and 140, respectively. In a further embodiment, the antibody or antibody fragment thereof comprises a heavy chain CDR1, CDR2, and CDR3 according to SEQ ID NOs: 135, 136, and 137, respectively, and a light chain CDR1, CDR2, and CDR3 according to SEQ ID NOs: 138, 139, and 140, respectively.

In one embodiment, the antibody or fragment thereof binds PD-L1 and comprises a heavy chain variable region comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 2, 6, 10, 14, 18, 22, 26, 30, 34, 38, 42, and 46; and a light chain variable region comprising an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 4, 8, 12, 16, 20, 24, 28, 32, 36, 40, 44, and 48. In a further embodiment, the isolated antibody or fragment thereof binds PD-L1 and comprises a heavy chain variable region comprising, consisting essentially of, or consisting of an amino acid sequence selected from the group consisting of SEQ ID NOs: 2, 6, 10, 14, 18, 22, 26, 30, 34, 38, 42, and 46; and a light chain variable region comprising, consisting essentially of, or consisting of an amino acid sequence selected from the group consisting of SEQ ID NOs: 4, 8, 12, 16, 20, 24, 28, 32, 36, 40, 44, and 48.

In one embodiment, the invention provides anti-PD-L1 antibodies that comprise a variable heavy chain of an antibody selected from the group consisting of 13C5, 5G9, 5G11, 8C6, 7B4, 4D1, 4A8, 8H4, 8H3, and 15F1 and a variable light chain of an antibody selected from the group consisting of 13C5, 5G9, 5G11, 8C6, 7B4, 4D1, 4A8, 8H4, 8H3, and 15F1. Thus, in one embodiment, the invention provides an antibody or fragment thereof comprising a heavy chain variable region comprising SEQ ID NO: 2 and a light chain variable region comprising SEQ ID NO: 4; a heavy chain variable region comprising SEQ ID NO: 6 and a light chain variable region comprising SEQ ID NO: 8; a heavy chain variable region comprising SEQ ID NO: 10 and a light chain variable region comprising SEQ ID NO: 12; a heavy chain variable region comprising SEQ ID NO: 14 and a light chain variable region comprising SEQ ID NO: 16; a heavy chain variable region comprising SEQ ID NO: 18 and a light chain variable region comprising SEQ ID NO: 20; a heavy chain variable region comprising SEQ ID NO: 22 and a light chain variable region comprising SEQ ID NO: 24; a heavy chain variable region comprising SEQ ID NO: 26 and a light chain variable region comprising SEQ ID NO: 28; a heavy chain variable region comprising SEQ ID NO: 30 and a light chain variable region comprising SEQ ID NO: 32; a heavy chain variable region comprising SEQ ID NO: 34 and a light chain variable region comprising SEQ ID NO: 36; or a heavy chain variable region comprising SEQ ID NO: 38 and a light chain variable region comprising SEQ ID NO: 40.

In one embodiment, the present invention provides a chimeric anti-PD-L1 antibody, wherein the antibody comprises a heavy chain having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 50, 54, 58, 60, 64, and 66; and a light chain having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 52, 56, 62 and 68.

In one embodiment, the present invention provides a humanized anti-PD-L1 antibody, wherein the antibody comprises a heavy chain variable region having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 42 and 46. In another embodiment, the present invention provides a humanized anti-PD-L1 antibody, wherein the antibody comprises a light chain variable region having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 44 and 48.

In another embodiment, the present invention provides a humanized anti-PD-L1 antibody, wherein the antibody comprises a heavy chain variable region having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to SEQ ID NO: 42 and a light chain variable region having least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to SEQ ID NO: 44. In another embodiment, the present invention provides a humanized anti-PD-L1 antibody, wherein the antibody comprises a heavy chain variable region having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to SEQ ID NO: 46 and a light chain variable region having least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to SEQ ID NO: 48.

In one embodiment, the present invention provides a humanized anti-PD-L1 antibody, wherein the antibody comprises a full heavy chain having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 70, 72, 76, and 78. In another embodiment, the present invention provides a humanized anti-PD-L1 antibody, wherein the antibody comprises a full light chain having an amino acid sequence having at least 80% homology, at least 85% homology, at least 90% homology, at least 91% homology, at least 92% homology, at least 93% homology, at least 94% homology, at least 95% homology, at least 96% homology, at least 97% homology, at least 98% homology, or at least 99% homology to an amino acid sequence selected from the group consisting of SEQ ID NOs: 74 and 80.

In one embodiment, the present invention provides a humanized anti-PD-L1 antibody, wherein the antibody comprises a heavy chain according to SEQ ID NO: 70 and a light chain according to SEQ ID NO: 74. In another embodiment, the present invention provides a humanized anti-PD-L1 antibody, wherein the antibody comprises a heavy chain according to SEQ ID NO: 72 and a light chain according to SEQ ID NO: 74. In another embodiment, the present invention provides a humanized anti-PD-L1 antibody, wherein the antibody comprises a heavy chain according to SEQ ID NO: 76 and a light chain according to SEQ ID NO: 80. In another embodiment, the present invention provides a humanized anti-PD-L1 antibody, wherein the antibody comprises a heavy chain according to SEQ ID NO: 78 and a light chain according to SEQ ID NO: 80.

In one embodiment, the present invention provides anti-PD-L1 antibodies or fragments thereof that bind to the same epitope on PD-L1 as any of the exemplary antibodies provided herein. In one embodiment, the antibodies or fragments thereof compete with any of the exemplary antibodies provided herein for binding to PD-L1. Binding to PD-L1 may be measured by ELISA, flow cytometry, surface plasmon resonance (SPR) assay, or any other method known in the art.

In one embodiment, the present invention provides anti-PD-L1 antibodies and fragments thereof that bind to PD-L1 with a binding affinity kD of about 10 nM to about 0.01 nM. In a further embodiment, the anti-PD-L1 antibodies and fragments thereof provided herein bind to PD-L1 with a binding affinity kD of from about 10 nM to about 0.05 nM. In a further embodiment, the anti-PD-L1 antibodies and fragments thereof provided herein bind to PD-L1 with a binding affinity kD of from about 8 nM to about 0.1 nM. In a further embodiment, the anti-PD-L1 antibodies and fragments thereof provided herein bind to PD-L1 with a binding affinity kD of from about 5 nM to about 0.2 nM. In another embodiment, the anti-PD-L1 antibodies and fragments thereof provided herein bind to PD-L1 with a binding affinity kD of about 10 nM or less. In a further embodiment, the anti-PD-L1 antibodies and fragments thereof provided herein bind to PD-L1 with a binding affinity kD of about 6 nM or less. In a further embodiment, the anti-PD-L1 antibodies and fragments thereof provided herein bind to PD-L1 with a binding affinity kD of about 4 nM or less. In a further embodiment, the anti-PD-L1 antibodies and fragments thereof provided herein bind to PD-L1 with a binding affinity kD of about 2 nM or less. In a further embodiment, the anti-PD-L1 antibodies and fragments thereof provided herein bind to PD-L1 with a binding affinity kD of about 1 nM or less. In a further embodiment, the anti-PD-L1 antibodies and fragments thereof provided herein bind to PD-L1 with a binding affinity kD of about 0.75 nM or less. In a further embodiment, the anti-PD-L1 antibodies and fragments thereof provided herein bind to PD-L1 with a binding affinity kD of about 0.5 nM or less. In a further embodiment, the anti-PD-L1 antibodies and fragments thereof provided herein bind to PD-L1 with a binding affinity kD of about 0.25 nM or less. In a further embodiment, the anti-PD-L1 antibodies and fragments thereof provided herein bind to PD-L1 with a binding affinity kD of about 0.2 nM or less. In a further embodiment, the anti-PD-L1 antibodies and fragments thereof provided herein bind to PD-L1 with a binding affinity kD of about 0.15 nM or less. In a further embodiment, the anti-PD-L1 antibodies and fragments thereof provided herein bind to PD-L1 with a binding affinity kD of about 0.1 nM or less. In a further embodiment, the anti-PD-L1 antibodies and fragments thereof provided herein bind to PD-L1 with a binding affinity kD of about 0.075 nM or less. In a further embodiment, the anti-PD-L1 antibodies and fragments thereof provided herein bind to PD-L1 with a binding affinity kD of about 0.05 nM or less. In a further embodiment, the anti-PD-L1 antibodies and fragments thereof provided herein bind to PD-L1 with a binding affinity kD of about 0.025 nM or less. In a further embodiment, the anti-PD-L1 antibodies and fragments thereof provided herein bind to PD-L1 with a binding affinity kD of about 0.02 nM or less. In a further embodiment, the anti-PD-L1 antibodies and fragments thereof provided herein bind to PD-L1 with a binding affinity kD of about 0.015 nM or less. In a further embodiment, the anti-PD-L1 antibodies and fragments thereof provided herein bind to PD-L1 with a binding affinity kD of about 0.01 nM or less. In one embodiment, the binding affinity kD of the anti-PD-L1 antibodies and fragments provided herein is measured by Biacore assay.

In one embodiment, the anti PD-L1 antibodies and fragments thereof provided herein have a binding EC50 for PD-L1 of about 1 ng/mL to about 2000 ng/mL. In a further embodiment, the anti PD-L1 antibodies and fragments thereof provided herein have a binding EC50 for PD-L1 of about 1 ng/mL to about 1500 ng/mL. In a further embodiment, the anti PD-L1 antibodies and fragments thereof provided herein have a binding EC50 for PD-L1 of about 1 ng/mL to about 1000 ng/mL. In a further embodiment, the anti PD-L1 antibodies and fragments thereof provided herein have a binding EC50 for PD-L1 of about 2 ng/mL to about 500 ng/mL. In a further embodiment, the anti PD-L1 antibodies and fragments thereof provided herein have a binding EC50 for PD-L1 of about 2 ng/mL to about 250 ng/mL. In a further embodiment, the anti PD-L1 antibodies and fragments thereof provided herein have a binding EC50 for PD-L1 of about 5 ng/mL to about 200 ng/mL. In a further embodiment, the anti PD-L1 antibodies and fragments thereof provided herein have a binding EC50 for PD-L1 of about 5 ng/mL to about 50 ng/mL. In one embodiment, the anti PD-L1 antibodies and fragments thereof provided herein have a binding EC50 for PD-L1 of about 500 ng/mL or less, about 400 ng/mL or less, about 300 ng/mL or less, about 250 ng/mL or less, about 200 ng/mL or less, about 150 ng/mL or less, about 100 ng/mL or less, about 75 ng/mL or less, about 60 ng/mL or less, about 50 ng/mL or less, about 40 ng/mL or less, or about 30 ng/mL or less. In one embodiment, the EC50 of the anti-PD-L1 antibodies and fragments provided herein is measured by ELISA or FACS.

In one embodiment, the anti PD-L1 antibodies and fragments thereof provided herein inhibit PDL1/PD-1 binding with an IC50 of about of about 1 ng/mL to about 1500 ng/mL. In a further embodiment, the anti PD-L1 antibodies and fragments thereof provided herein inhibit PDL1/PD-1 binding with an IC50 of about 2 ng/mL to about 1200 ng/mL. In a further embodiment, the anti PD-L1 antibodies and fragments thereof provided herein inhibit PDL1/PD-1 binding with an IC50 of about 5 ng/mL to about 500 ng/mL. In a further embodiment, the anti PD-L1 antibodies and fragments thereof provided herein inhibit PDL1/PD-1 binding with an IC50 of about 5 ng/mL to about 100 ng/mL. In a further embodiment, the anti PD-L1 antibodies and fragments thereof provided herein inhibit PDL1/PD-1 binding with an IC50 of about 10 ng/mL to about 50 ng/mL. In one embodiment, the anti PD-L1 antibodies and fragments thereof provided herein inhibit PDL1/PD-1 binding with an IC50 of about 1200 ng/mL or less, about 1000 ng/mL or less, about 800 ng/mL or less, about 400 ng/mL or less, about 300 ng/mL or less, about 250 ng/mL or less, about 200 ng/mL or less, about 150 ng/mL or less, about 100 ng/mL or less, about 75 ng/mL or less, about 60 ng/mL or less, about 50 ng/mL or less, about 40 ng/mL or less, about 30 ng/mL or less, about 20 ng/mL or less, or about 10 ng/mL or less. In one embodiment, the IC50 of the anti-PD-L1 antibodies and fragments provided herein is measured by ELISA or FACS.

In one embodiment, the anti-PD-L1 antibody provided herein is a humanized antibody having a heavy chain variable region amino acid sequence according to SEQ ID NO: 42 and a light chain variable region amino acid according to SEQ ID NO: 44; or having a heavy chain variable region amino acid sequence according to SEQ ID NO: 46 and a light chain variable region amino acid sequence according to SEQ ID NO: 48; wherein the anti-PD-L1 antibody has a PD-L1 binding EC50 of about 200 ng/mL or less or about 150 ng/mL or less or about 100 ng/mL or less or about 80 ng/ml or less or about 60 ng/mL or less or about 50 ng/mL or less, as measured by ELISA or FACS. In another embodiment, the anti-PD-L1 antibody provided herein is a humanized antibody having a heavy chain variable region amino acid sequence according to SEQ ID NO: 42 and a light chain variable region amino acid according to SEQ ID NO: 44; or having a heavy chain variable region amino acid sequence according to SEQ ID NO: 46 and a light chain variable region amino acid sequence according to SEQ ID NO: 48; wherein the anti-PD-L1 antibody has a PDL1/PD-1 blockage IC50 of about 1200 ng/mL or less, or about 1000 ng/mL or less, or about 800 ng/mL or less, or about 600 ng/mL or less, or about 500 ng/mL or less, or about 400 ng/mL or less, or about 300 ng/mL or less, or about 200 ng/mL or less, or about 100 ng/mL or less, or about 60 ng/mL or less, or about 30 ng/mL or less, or about 25 ng/mL or less, or about 20 ng/mL or less, or about 10 ng/mL or less, as measured by ELISA or FACS. In another embodiment, the anti-PD-L1 antibody provided herein is a humanized antibody having a heavy chain variable region amino acid sequence according to SEQ ID NO: 42 and a light chain variable region amino acid according to SEQ ID NO: 44; or having a heavy chain variable region amino acid sequence according to SEQ ID NO: 46 and a light chain variable region amino acid sequence according to SEQ ID NO: 48; wherein the anti-PD-L1 antibody has a binding affinity kD for PD-L1 of about 10 nM or less, or about 5 nM or less, or about 2 nM or less, or about 1 nM or less, or about 0.5 nM or less, or about 0.1 nM or less, or about 0.05 nM or less, as measured by Biacore assay. In one embodiment, the humanized anti-PD-L1 antibody has a binding affinity kD for PD-L1 of about 2 nM. In another embodiment, the humanized anti-PD-L1 antibody has a binding affinity kD for PD-L1 of about 1 nM. In another embodiment, the humanized anti-PD-L1 antibody has a binding affinity kD for PD-L1 of about 0.5 nM. In another embodiment, the humanized anti-PD-L1 antibody has a binding affinity kD for PD-L1 of about 0.1 nM.

In one embodiment, the anti-PD-L1 antibodies and fragments thereof provided herein bind to PD-L1, disrupting the PD-1/PD-L1 interaction and resulting in an increase in T cell activation. In a further embodiment, the antibodies and fragments thereof bind PD-L1 and result in an increase in T cell proliferation and/or cytokine production. In a yet further embodiment, the antibodies and fragments thereof bind PD-L1 and result in an increase of one or more cytokines selected from the group consisting of IL-2, IFNγ, TNF, IL-1, IL-4, IL-5, IL-6, IL-12, IL-13, IL-17, and GM-CSF. Thus, in one aspect, the present invention provides methods for modulating an immune response comprising contacting T cells and antigen presenting cells with the anti-PD-L1 antibody or fragment thereof. In one embodiment, the modulation of an immune response by the anti-PD-L1 antibodies and fragments provided herein may be measured in a mixed lymphocyte (MLR) reaction. In one embodiment, the anti-PD-L1 antibodies provided herein increase the level of cytokine production from lymphocytes in an MLR. In a further embodiment, the anti-PD-L1 antibodies increase the level of IL-2 production and/or IFNγ production in an MLR. In a yet further embodiment, the anti-PD-L1 antibodies increase the level of IL-2 production and IFNγ production in an MLR. In one embodiment, the anti-PD-L1 antibodies enhance memory T cell responses. In a further embodiment, the anti-PD-L1 antibodies enhance memory T cell responses as measured by an increase in IFNγ production from memory T cells.

In one embodiment, the anti-PD-L1 antibodies and fragments thereof provided herein inhibit regulatory T cell function. In a further embodiment, the anti-PD-L1 antibodies and fragments thereof inhibit the suppression of effector T cells by regulatory T cells. In another embodiment, the anti-PD-L1 antibodies and fragments thereof restore the effector functions of T cells in the presence of regulatory T cells. In a further embodiment, the anti-PD-L1 antibodies and fragments thereof restore the ability of effector T cells to proliferate and/or produce cytokines in the presence of regulatory T cells. Thus, in one embodiment, the present invention provides a method for inhibiting the suppressive effects of regulatory T cells in vitro or in a subject in need thereof.

In one aspect, an isolated antibody or fragment thereof that binds to PD-L1 is provided, wherein the antibody is produced by a hybridoma selected from the group consisting of the hybridomas herein termed 13C5, 5G9, 5G11, 8C6, 7B4, 4D1, 4A8, 8H4, 8H3, and 15F1. Thus, the present invention also encompasses the hybridomas 13C5, 5G9, 5G11, 8C6, 7B4, 4D1, 4A8, 8H4, 8H3, and 15F1, as well as any hybridoma producing an antibody disclosed herein. The present invention also provides isolated polynucleotides encoding the antibodies and fragments thereof provided herein. Expression vectors comprising the isolated polynucleotides, and host cells comprising such expression vectors, are also encompassed in the invention.

In one embodiment, the present invention provides anti-PD-L1 antibody immunoconjugates. Thus, the present invention provides an antibody or fragment thereof that binds to PD-L1 and that is linked or conjugated to a therapeutic agent. Therapeutic agents that may be linked or conjugated to the anti-PD-L1 antibody may include, but are not limited to, cytotoxic drugs, radioactive isotopes, immunomodulators, or antibodies.

In one aspect, the present invention provides compositions comprising one or more anti-PD-L1 antibody or fragment thereof provided herein, and a pharmaceutically acceptable carrier.

In one aspect, the present invention provides methods for modulating an immune response in a subject, the method comprising administering to the subject a therapeutically effective amount of an anti-PD-L1 antibody or fragment thereof provided herein. In one embodiment, the present invention provides methods for treating or preventing a disease or disorder in a subject in need thereof, comprising administering to the subject a therapeutically effective amount of an anti-PD-L1 antibody or fragment thereof provided herein.

In one embodiment, the present invention provides a method for enhancing anti-tumor responses in a subject in need thereof, comprising administering to the subject a therapeutically effective amount of an anti-PD-L1 antibody or fragment of the invention. In another embodiment, the present invention provides a method for reducing tumors or inhibiting the growth of tumor cells in a subject in need thereof, comprising administering to the subject a therapeutically effective amount of an anti-PD-L1 antibody or fragment of the invention. In another embodiment, the present invention provides a method for treating cancer in a subject in need thereof, comprising administering to the subject a therapeutically effective amount of an anti-PD-L1 antibody or fragment of the invention. In a further embodiment, the cancer is selected from the group consisting of lymphoma, leukemia, melanoma, glioma, breast cancer, lung cancer, colon cancer, bone cancer, ovarian cancer, bladder cancer, kidney cancer, liver cancer, stomach cancer, rectal cancer, testicular cancer, salivary cancer, thyroid cancer, thymic cancer, epithelial cancer, head or neck cancer, gastric cancer, pancreatic cancer, or a combination thereof.

In one embodiment, the present invention provides a method for treating an infectious disease in a subject in need thereof, comprising administering to the subject a therapeutically effective amount of an anti-PD-L1 antibody or fragment of the invention. In a further embodiment, the infectious disease is selected from the group consisting of candidiasis, candidemia, aspergillosis, streptococcal pneumonia, streptococcal skin and oropharyngeal conditions, gram negative sepsis, tuberculosis, mononucleosis, influenza, respiratory illness caused by Respiratory Syncytial Virus, malaria, schistosomiasis, and trypanosomiasis.

BRIEF DESCRIPTION OF THE FIGURES

FIG. 3a-b is set of graphs showing the binding of humanized anti-PD-L1 antibodies to PD-L1 over a range of antibody concentrations as measured by ELISA. Binding of control hIgG4 and humanized antibodies hu5G11-hIgG1 and hu5G11-hIgG4 is shown in FIG. 3a. Binding of control hIgG4 and humanized antibodies hu13C5-hIgG1 and hu13C5-hIgG4 is shown in FIG. 3b.

FIGS. 7a and 7b show the binding of the hybridoma anti-PD-L1 antibodies to PD-L1 over a range of antibody concentrations as measured by FACS. Binding (as measured by the mean fluorescence intensity) of hybridoma antibodies 4A8, 15F1, 4D1, 13C5, 8H4, and 8H3 as compared to control antibody mIgG1 is shown in FIG. 7a. Binding (as measured by the mean fluorescence intensity) of hybridoma antibodies 5G11, 8C6, 5G9, or 7B4 as compared to control antibody mIgG1 is shown in FIG. 7b.

DETAILED DESCRIPTION

Figure 1:
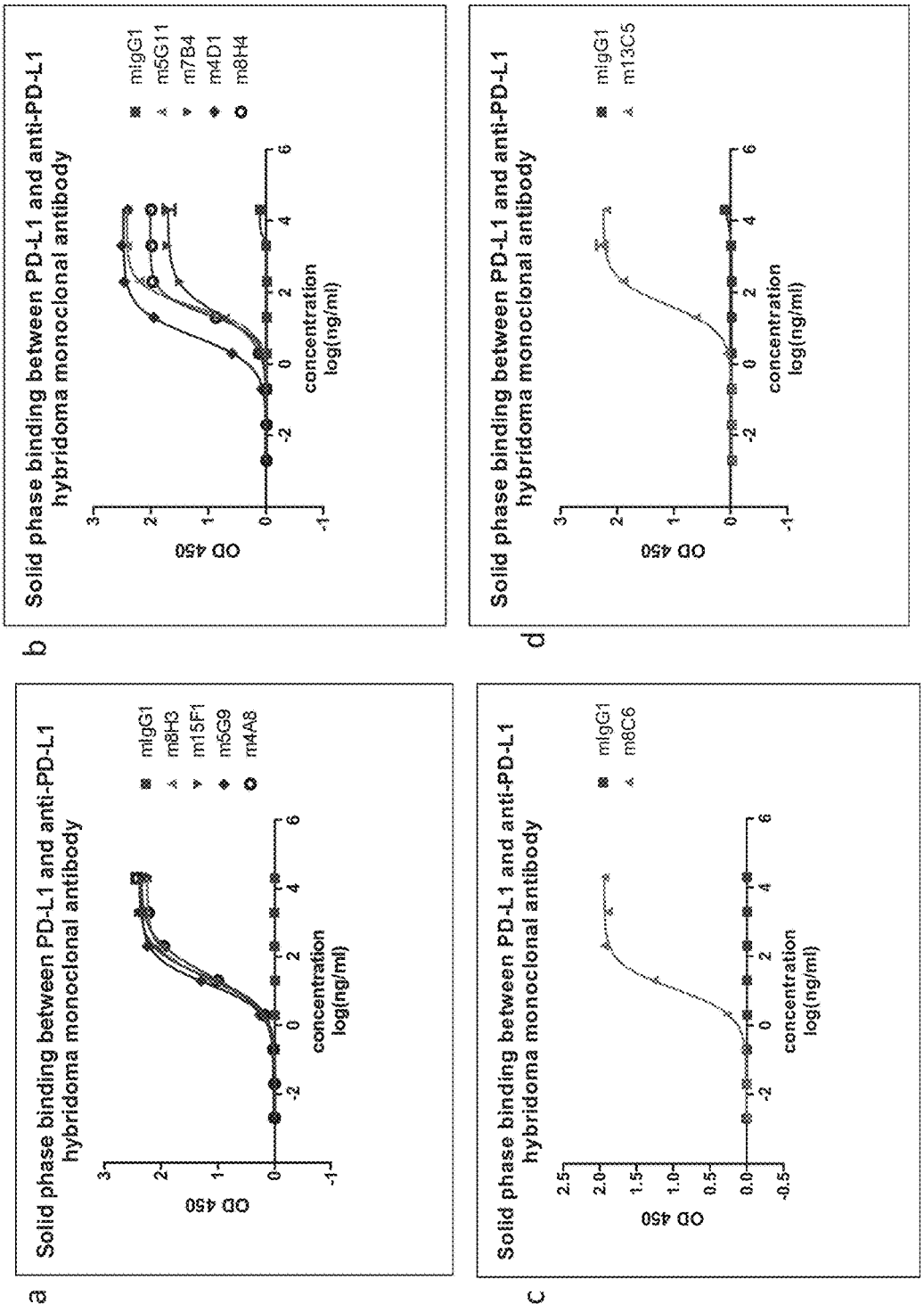
FIG. 1a-d is set of graphs showing the binding of the murine hybridoma anti-PD-L1 antibodies to PD-L1 over a range of antibody concentrations as measured by ELISA. Binding of hybridoma antibodies 8H3-mIgG (m8H3), 15F1-mIgG (m15F1), 5G9-mIgG (m5G9), and 4A8-mIgG (m4A8) is shown in FIG. 1a. Binding of hybridoma antibodies 5G11-mIgG (m5G11), 7B4-mIgG (m7B4), 4D1-mIgG (m4D1), and 8H4-mIgG (m8H4) is shown in FIG. 1b. Binding of hybridoma antibody 8C6-mIgG (m8C6) is shown in FIG. 1c. Binding of hybridoma antibody 13C5-mIgG (m13C5) is shown in FIG. 1d. In each of FIGS. 1a-1d, binding of mIgG1 is shown as a negative control.

PD1/PDL1 interactions inhibit T cell receptor signaling by recruiting the SHP1 and SHP2 phosphatases, which interfere with TCR signaling (Chemnitz et al. (2004) J. Immunol. 17:945-954). PD-L1 can not only promote tumor progression through inhibition of PD1-expressing immune effectors, but also modulate cell-mediated immunity in some infectious diseases (Mueller et al. (2010) J. Clin. Invest. 120:2508-2515). Furthermore, allogeneic effector T cell responses are susceptible to PD-1 pathway modulation in graft rejection (Lee et al. (2003) J. Immunol. 171:6929-6935). Therefore, the interaction of PD-1 with PD-L1 exerts a vital and diverse range of immunoregulatory roles in T cell activation, tolerance, and immune-mediated tissue damage. However, the interaction can be reversed by blocking the local binding of PD-1 with PD-L1 (Iwai et al. (2002) Proc. Nat'l. Acad Sci. USA 99: 12293-7; Brown et al. (2003) J. Immunol. 170:1257-66).

PD-1 has been found to have a correlation with cancer growth and development due to its role in protecting tumor cells from efficient immune destruction. Its ligand, PD-L1, has been revealed to have significant expression on a number of mouse and human tumors, which is postulated to mediate immune evasion (Iwai, Y. et al., Proc. Natl. Acad. Sci. USA. 99: 12293-12297 (2002); Strome S. E. et al., Cancer Res., 63:6501-6505 (2003); Dong et al. (2002) Nat. Med. 8:787-9). In humans, expression of PD-1 (on tumor infiltrating lymphocytes) and/or PD-L1 (on tumor cells) has been found in a number of primary tumor biopsies as assessed by immunohistochemistry. Such tissues include cancers of the lung, liver, ovary, cervix, skin, colon, glioma, bladder, breast, kidney, esophagus, stomach, oral squamous cell, urothelial cell, and pancreas as well as tumors of the head and neck (Brown J. A. et al., J. Immunol. 170: 1257-1266 (2003); Dong H. et al., Nat. Med. 8: 793-800 (2002); Wintterle et al., Cancer Res. 63:7462-7467 (2003); Strome S. E. et al., Cancer Res., 63: 6501-6505 (2003); Thompson R. H. et al., Cancer Res. 66: 3381-5 (2006); Thompson et al., Clin. Cancer Res. 13: 1757-61 (2007); Nomi T. et al., Clin. Cancer Res. 13: 2151-7. (2007)). More strikingly, PD-1 ligand expression on tumor cells has been correlated to poor prognosis of cancer patients across multiple tumor types (reviewed in OkaZaki and Honjo, Int. Immunol. 19: 813-824 (2007)).

While the interaction between PD-1 and PD-L1 results in a decrease in tumor infiltrating lymphocytes, a decrease in T-cell receptor mediated proliferation, and immune evasion by the cancerous cells (Dong et al. (2003) J. Mol. Med. 81:281-7; Blank et al. (2005) Cancer Immunol. Immunother. 54: 3 07-3 14; Konishi et al. (2004) Clin. Cancer Res. 10:5094-100), blockade of the PD-1/PD-L1 interaction was accordingly shown to enhance tumor-specific T-cell immunity and be helpful in clearance of tumor cells by the immune system. In a murine model of aggressive pancreatic cancer, for example, Nomi T., et al. (Clin. Cancer Res. 13: 2151-2157, 2007) demonstrated the therapeutic efficacy of PD-1/PD-L1 blockade. Administration of either PD-1 or PD-L1 directed antibody significantly inhibited tumor growth. Antibody blockade effectively promoted tumor reactive CD8+ T cell infiltration into the tumor resulting in the up-regulation of anti-tumor effectors including IFN-γ, granzyme B and perforin. Additionally, the authors showed that PDL1/PD-1 blockade can be effectively combined with chemotherapy to yield a synergistic effect. In another study, using a model of squamous cell carcinoma in mice, antibody blockade of PD-1 or PD-L1 significantly inhibited tumor growth (Tsushima F. et al., Oral Oncol. 42:268-274 (2006)).

Furthermore, transfection of a murine mastocytoma line with PD-L1 led to decreased lysis of the tumor cells when co-cultured with a tumor-specific CTL clone. Lysis was restored when anti-PD-L1 mAb was added (Iwai Y. et al., Proc. Natl. Acad. Sci. USA. 99: 12293-12297 (2002)). In vivo, blocking the PD1/PD-L1 interaction was shown to increase the efficacy of adoptive T cell transfer therapy in a mouse tumor model (Strome S. E. et al., Cancer Res. 63:6501-6505 (2003)). Further evidence for the role of PD-1 in cancer treatment comes from experiments performed with PD-1 knockout mice. PD-L1 expressing myeloma cells grew only in Wild-type animals (resulting in tumor growth and associated animal death), but not in PD-1 deficient mice (Iwai Y., et al., Proc. Natl. Acad. Sci. USA. 99: 12293-12297 (2002)). In human studies, R. M. Wong et al. (Int. Immunol. 19:1223-1234 (2007)) showed that PD-1 blockade using a fully human anti-PD-1 antibody augmented the absolute numbers of tumor-specific CD8+ T cells (CTLs) in ex vivo stimulation assays using vaccine antigens and cells from vaccinated individuals. In a similar study, antibody blockade of PD-L1 resulted in enhanced cytolytic activity of tumor-associated antigen-specific cytotoxic T cells and increased cytokine production by tumor specific TH cells (Blank C. et al., Int. J. Cancer 119: 317-327 (2006)). The same authors showed that PD-L1 blockade augments tumor-specific T cell responses in vitro when used in combination with anti-CTLA-4 blockade. Overall, the PD-1/PD-L1 pathway is a target for the development of antibody therapeutics for cancer treatment. Anti-PD-L1 antibodies may also be useful in chronic viral infection. Memory CD8+ T cells generated after an acute viral infection are highly functional and constitute an important component of protective immunity. In contrast, chronic infections are often characterized by varying degrees of functional impairment (exhaustion) of virus-specific T-cell responses, and this defect is a principal reason for the inability of the host to eliminate the persisting pathogen. Although functional effector T cells are initially generated during the early stages of infection, they gradually lose function during the course of a chronic infection. Barber et al. (Barber et al., Nature 439: 682-687 (2006)) showed that mice infected with a laboratory strain of LCMV developed chronic infection resulting in high levels of virus in the blood and other tissues. These mice initially developed a robust T cell response, but eventually succumbed to the infection upon T cell exhaustion. The authors found that the decline in number and function of the effector T cells in chronically infected mice could be reversed by injecting an antibody that blocked the interaction between PD-1 and PD-L1.

In one aspect, the present invention provides antibodies or antigen binding fragments thereof that bind to programmed death ligand 1 (PD-L1). In one embodiment, the antibodies or fragments thereof bind to human PD-L1. In another embodiment, the antibodies or fragments thereof bind to human and to cynomolgus PD-L1. In another embodiment, the antibodies or fragments thereof block the interaction of PD-L1 with its receptor PD-1 on T cells. In one aspect, the present invention provides methods of making and using the anti-PD-L1 antibodies or fragments thereof, and compositions comprising anti-PD-L1 antibodies or fragments thereof, including pharmaceutical compositions.

As used herein, the term "antibody" refers to a binding protein having at least one antigen binding domain. The antibodies and fragments thereof of the present invention may be whole antibodies or any fragment thereof. Thus, the antibodies and fragments of the invention include monoclonal antibodies or fragments thereof and antibody variants or fragments thereof, as well as immunoconjugates. Examples of antibody fragments include Fab fragments, Fab' fragments, F(ab)' fragments, Fv fragments, isolated CDR regions, single chain Fv molecules (scFv), and other antibody fragments known in the art. Antibodies and fragments thereof may also include recombinant polypeptides, fusion proteins, and bi-specific antibodies. The anti-PD-L1 antibodies and fragments thereof disclosed herein may be of an IgG1, IgG2, IgG3, or IgG4 isotype. The term "isotype" refers to the antibody class encoded by the heavy chain constant region genes. In one embodiment, the anti-PD-L1 antibodies and fragments thereof disclosed herein are of an IgG1 or an IgG4 isotype. The PD-L1 antibodies and fragments thereof of the present invention may be derived from any species including, but not limited to, mouse, rat, rabbit, primate, llama, and human. The PD-L1 antibodies and fragments thereof may be chimeric, humanized, or fully human antibodies. In one embodiment, the anti-PD-L1 antibodies are antibodies produced by a hybridoma cell line derived from a mouse. Thus, in one embodiment, the anti-PD-L1 antibodies are murine antibodies. In another embodiment, the anti-PD-L1 antibodies are chimeric antibodies. In a further embodiment, the chimeric antibodies are mouse-human chimeric antibodies. In another embodiment, the antibodies are humanized antibodies. In a further embodiment, the antibodies are derived from murine antibodies and are humanized.

A "chimeric antibody" is an antibody having at least a portion of the heavy chain variable region and at least a portion of the light chain variable region derived from one species; and at least a portion of a constant region derived from another species. For example, in one embodiment, a chimeric antibody may comprise murine variable regions and a human constant region.

A "humanized antibody" is an antibody containing complementarity determining regions (CDRs) that are derived from a non-human antibody; and framework regions as well as constant regions that are derived from a human antibody. For example, the anti-PD-L1 antibodies provided herein may comprise CDRs derived from one or more murine antibodies and human framework and constant regions. Thus, in one embodiment, the humanized antibody provided herein binds to the same epitope on PD-L1 as the murine antibody from which the antibody's CDRs are derived. Exemplary humanized antibodies are provided herein. Additional anti-PD-L1 antibodies comprising the heavy and light chain CDRs provided herein, or variants thereof, may be generated using any human framework sequence, and are also encompassed in the present invention. In one embodiment, framework sequences suitable for use in the present invention include those framework sequences that are structurally similar to the framework sequences provided herein. Further modifications in the framework regions may be made to improve the properties of the antibodies provided herein. Such further framework modifications may include chemical modifications; point mutations to reduce immunogenicity or remove T cell epitopes; or back mutation to the residue in the original germline sequence. In some embodiments, such modifications include those corresponding to the mutations exemplified herein, including backmutations to the germline sequence. For example, in one embodiment, one or more amino acids in the human framework regions of the VH and/or VL of the humanized antibodies provided herein are back mutated to the corresponding amino acid in the parent murine antibody. As an example, as for VH and VL of humanized 5G11 and humanized 13C5, several sites of framework amino acid of the aforementioned template human antibody were back mutated to the corresponding amino acid sequences in mouse 5G11 and 13C5 antibodies. In one embodiment, the amino acid at positions 53 and/or 60 and/or 67 of the light chain variable region is back mutated to the corresponding amino acid found at that position in the mouse 5G11 or 13C5 light chain variable region. In another embodiment, the amino acid at positions 24 and/or 28 and/or 30 and/or 49 and/or 73 and/or 83 and/or 94 of the heavy chain variable region is back mutated to the corresponding amino acid found at that position in the mouse 5G11 or 13C5 heavy chain variable region. In one embodiment, the humanized 5G11 antibody comprises a light chain variable region wherein the amino acid at position 60 is mutated from Ser (S) to Asp (D) and the amino acid at position 67 is mutated from Ser (S) to Tyr (Y); and a heavy chain variable region wherein the amino acid at position 24 is mutated from Phe (F) to Val (V), the amino acid at position 49 is mutated from Ala (A) to Gly (G), the amino acid at position 73 is mutated from Thr (T) to Asn (N), and the amino acid at position 83 is mutated from Thr (T) to Asn (N). In one embodiment, the humanized 13C5 antibody comprises a light chain variable region wherein the amino acid at position 53 is mutated from Tyr (Y) to Lys (K); and a heavy chain variable region wherein the amino acid at position 28 is mutated from Thr (T) to Ile (I), the amino acid at position 30 is mutated from Ser (S) to Arg (R), the amino acid at position 49 is mutated from Ser (S) to Ala (A), and the amino acid at position 94 is mutated from Tyr (Y) to Asp (D). Additional or alternate back mutations may be made in the framework regions of the humanized antibodies provided herein in order to improve the properties of the antibodies. The present invention also encompasses humanized antibodies that bind to PD-L1 and comprise framework modifications corresponding to the exemplary modifications described herein with respect to any suitable framework sequence, as well as other framework modifications that otherwise improve the properties of the antibodies.

As used herein, the term "derived" when used to refer to a molecule or polypeptide relative to a reference antibody or other binding protein, means a molecule or polypeptide that is capable of binding with specificity to the same epitope as the reference antibody or other binding protein.

The antibodies and antigen-binding fragments thereof disclosed herein are specific for PD-L1. In one embodiment, the antibodies and fragments thereof are specific for human PD-L1. In one embodiment, the antibodies and fragments provided herein bind to human or primate PD-L1 but not to PD-L1 from any other mammal. In a further embodiment, the antibodies and fragments thereof do not bind to mouse PD-L1. The terms "human PD-L1," "hPD-L1", and "huPD-L1" and the like are used interchangeably herein and refer to human PD-L1 and variants or isoforms of human PD-L1. By "specific for" is meant that the antibodies and fragments thereof bind PD-L1 with greater affinity than any other target. As used herein, the term "EC50" refers to the effective concentration, 50% maximal response of the antibody. As used herein, the term "IC50" refers to the inhibitory concentration, 50% maximal response of the antibody. Both EC50 and IC50 may be measured by ELISA or FACS analysis, or any other method known in the art.

In one embodiment, the anti-PD1 antibodies and fragments or variants thereof have a binding affinity (KD) for PD-L1 in the range of about 0.001 nM to about 100 nM, about 0.002 nM to about 50 nM, about 0.005 nM to about 5 nM, about 0.01 nM to about 1 nM, or about 0.05 nM to about 0.1 nM. In one embodiment, the antibodies and fragments thereof have a binding affinity (KD) for PD-L1 of about 50 nM or less, about 25 nM or less, about 20 nM or less, about 15 nM or less, about 10 nM or less, about 8 nM or less, about 6 nM or less, about 5 nM or less, about 4 nM or less, about 3 nM or less, about 2 nM or less, about 1 nM or less, about 0.9 nM or less, about 0.8 nM or less, about 0.7 nM or less, about 0.6 nM or less, about 0.5 nM or less, about 0.4 nM or less, about 0.3 nM or less, about 0.2 nM or less, about 0.1 nM or less, about 0.09 nM or less, about 0.08 nM or less, about 0.07 nM or less, about 0.06 nM or less, about 0.05 nM or less, about 0.04 nM or less, about 0.03 nM or less, about 0.02 nM or less, about 0.01 nM or less, about 0.009 nM or less, about 0.008 nM or less, about 0.007 nM or less, about 0.006 nM or less, about 0.005 nM or less, about 0.004 nM or less, about 0.003 nM or less, about 0.002 nM or less, or about 0.001 nM or less. In one embodiment, the antibodies and fragments thereof have a binding affinity (KD) for PD-L1 of about 10 nM, about 9 nM, about 8 nM, about 7 nM, about 6 nM, about 5 nM, about 4 nM, about 3 nM, about 2 nM, about 1 nM, about 0.9 nM, about 0.8 nM, about 0.7 nM, about 0.6 nM, about 0.5 nM, about 0.4 nM, about 0.3 nM, about 0.2 nM, about 0.1 nM, about 0.09 nM, about 0.08 nM, about 0.07 nM, about 0.06 nM, about 0.05 nM, about 0.04 nM, about 0.03 nM, about 0.02 nM, about 0.01 nM, about 0.009 nM, about 0.008 nM, about 0.007 nM, about 0.006 nM, about 0.005 nM, about 0.004 nM, about 0.003 nM, about 0.002 nM, or about 0.001 nM.

In one embodiment, the antibodies and fragments provided herein comprise a light chain and a heavy chain, each of which comprises three CDR regions. Exemplary heavy chain CDR sequences (HCDR1, HCDR2, and HCDR3) for PD-L1 antibodies of the invention are provided below in Table 1. Exemplary light chain CDR sequences (LCDR1, LCDR2, and LCDR3) for PD-L1 antibodies of the invention are provided below in Table 2. Exemplary variable regions and full length heavy and light chain sequences for PD-L1 antibodies of the invention are provided below in Table 3.

TABLE 1

Heavy Chain CDR Sequences

| Name | HCDR | SEQ ID NO | Sequence |
|---|---|---|---|
| 13C5 | 1 | 81 | SYGMS |
|  | 2 | 82 | SISSGGSTYYPDSVKG |
|  | 3 | 83 | GYDSGFAY |
| 5G9 | 1 | 87 | SYGMS |
|  | 2 | 88 | SISSGGTTYYPDSVKG |
|  | 3 | 89 | GYDSGFAY |
| 5G11 | 1 | 93 | TYGVH |
|  | 2 | 94 | VIWRGVTTDYNAAFMS |
|  | 3 | 95 | LGFYAMDY |
| 8C6 | 1 | 99 | SYGVH |
|  | 2 | 100 | VIWSGGVTDYNAAFIS |
|  | 3 | 101 | LGFYAMDY |
| 7B4 | 1 | 105 | TYWMH |
|  | 2 | 106 | QINPDSTTINYAPSLKD |
|  | 3 | 107 | PGDYGYDFDC |
| 4D1 | 1 | 111 | SGYWN |
|  | 2 | 112 | YISYSGSTYYNPSLKS |
|  | 3 | 113 | SLLWFSTGFAY |
| 4A8 | 1 | 117 | SYGVH |
|  | 2 | 118 | VIWSGGITDYNAAFKS |
|  | 3 | 119 | LGFYAMDY |
| 8H4 | 1 | 123 | SYGMS |
|  | 2 | 124 | SISSGGTTYYLGSVQG |
|  | 3 | 125 | GYDAGFAY |
| 8H3 | 1 | 129 | SGYWT |
|  | 2 | 130 | YISYTGSTYYNPSLKS |
|  | 3 | 131 | QRDWLGFAY |
| 15F1 | 1 | 135 | SYGMS |
|  | 2 | 136 | SISSGGSIYYPDSVKG |
|  | 3 | 137 | GYDAGFAF |

TABLE 2

Light chain CDR Sequences

| Name | LCDR | SEQ ID NO | Sequence |
|---|---|---|---|
| 13C5 | 1 | 84 | ASQSVSTSSSSFMH |
|  | 2 | 85 | YASNLES |
|  | 3 | 86 | QHSWEIPYT |
| 5G9 | 1 | 90 | RASQSVSTSSSSYMH |
|  | 2 | 91 | YASNLES |
|  | 3 | 92 | QHSWEIPYT |
| 5G11 | 1 | 96 | KASQSVSNDVA |
|  | 2 | 97 | YAANRYT |
|  | 3 | 98 | QQDYTSPYT |
| 8C6 | 1 | 102 | KASQSVSNDVG |
|  | 2 | 103 | YASNRYS |
|  | 3 | 104 | QQDYTSPYT |
| 7B4 | 1 | 108 | RSSQIIVHSNANTYLE |
|  | 2 | 109 | KVSNRFS |
|  | 3 | 110 | FQGSHVPYT |
| 4D1 | 1 | 114 | SASSSVSSSYLY |
|  | 2 | 115 | NTSNLAS |
|  | 3 | 116 | HQWRSYPPT |
| 4A8 | 1 | 120 | SANSSVSYMH |
|  | 2 | 121 | DTSKLAS |
|  | 3 | 122 | QQWSSNPWT |
| 8H4 | 1 | 126 | RASQSVSTSYSYMH |
|  | 2 | 127 | YASNLES |
|  | 3 | 128 | QNSWEIPYT |
| 8H3 | 1 | 132 | KSSQSLLYSSNQKNSLA |
|  | 2 | 133 | WASNRES |
|  | 3 | 134 | QQYYSYPLT |
| 15F1 | 1 | 138 | RASQSVSTSYSYVH |
|  | 2 | 139 | YASNLES |
|  | 3 | 140 | QHSWEIPYT |

TABLE 3

Heavy chain and light chain variable region and full length heavy and light chain amino acid sequences

| Name | Region | SEQ ID NO | Sequence |
|---|---|---|---|
| 13C5 murine | Heavy chain variable | 2 | EVKLVESGGGLVKPGGSLKLSCAASGFIFRSYGMSWVRQTPEKRLEWVASISSGGSTYYPDSVKGRFTISRDNARNILYLQMSSLRSEDTAMYDCARGYDSGFAYWGQGTLVTVSE |
| 13C5 murine | Light chain variable | 4 | DIVLTQSPASLAVSLGQRATISCRASQSVSTSSSSFMHWYQQKPGQPPKLLIKYASNLESGVPARFSGSGSGTDFTLNIHPVEEEDTATYYCQHSWEIPYTFGGGTKLEIKR |
| 5G9 murine | Heavy chain variable | 6 | EVKLVESGGGLVKPGGSLKLSCAASGFTFRSYGMSWVRQTPEKRLEWVASISSGGTTYYPDSVKGRFIISRDNARNILYLQMSSLRSEDTAMYYCAKGYDSGFAYWGQGTLVIVSA |
| 5G9 murine | Light chain variable | 8 | DIVLTQSPPSLAVSLGQRATISCRASQSVSTSSSSYMHWYQQKPGQPPKLLIKYASNLESGVPARFSGSGSGTDFTLNIHPVEEEDTATYYCQHSWEIPYTFGGGTKLEIK |
| 5G11 murine | Heavy chain variable | 10 | QVQLKQSGPGLVQPSQSLSITCTVSGFSLTTYGVHWVRQSPGKGLEWLGVIWRGVTTDYNAAFMSRLTITKDNSKSQVFFKMNSLQANDTAIYYCARLGFYAMDYWGQGTSVTVSS |
| 5G11 murine | Light chain variable | 12 | SIVMTQTPKFLLVSAGDRVTITCKASQSVSNDVAWYQQKPGQSPKLLIYYAANRYTGVPDRFTGSGYGTDFTFTISIVQAEDLAVYFCQQDYTSPYTFGGGTKLEIK |

TABLE 3-continued

Heavy chain and light chain variable region and full length
heavy and light chain amino acid sequences

| Name | Region | SEQ ID NO | Sequence |
|---|---|---|---|
| 8C6 murine | Heavy chain variable | 14 | QVQLKQSGPGLVQPSQSLSITCTVSGFSLTSYGVHWVRQSPG KGLEWLGVIWSGGVTDYNAAFISRLSISKDNSKSQVFFKMNS LQANDTAIYYCARLGFYAMDYWGQGTSVTVSS |
| 8C6 murine | Light chain variable | 16 | SIVMTQTPKFLLVSAGDRVTITCKASQSVSNDVGWYQQKPG QSPKLLIYYASNRYSGVPDRFTGSGYGTDFTFTISTVQAEDLA VYFCQQDYTSPYTFGGGTKLEIK |
| 7B4 murine | Heavy chain variable | 18 | EVKLFESGGGLVQPGGSLKLSCVASGFDFSTYWMHWVRQAP GQGLEWIGQINPDSTTINYAPSLKDRFIISRDNAKNTLFLQMS KVRSEDTALYYCAKPGDYGYDFDCWGQGTTLTVSS |
| 7B4 murine | Light chain variable | 20 | DVLMTQTPLYLPVSLGDQASISCRSSQIIVHSNANTYLEWFLQ KPGQSPKLLIYKVSNRFSGVPDRFSGSGSGTDFTLKISRVEAE DLGVYYCFQGSHVPYTFGGGTKLEIK |
| 4D1 murine | Heavy chain variable | 22 | EVQLQESGPSLVKPSQTLSLTCSVTGDSITSGYWNWIRKFPGN KLEYMGYISYSGSTYYNPSLKSRISITRDTSKNQYYLQLNSVT TEDTATYYCARSLLWFSTGFAYWGQGTLVTVSA |
| 4D1 murine | Light chain variable | 24 | QIVLTQSPAIMSASPGEKVTLTCSASSSVSSSYLYWNQQKPGS SPKVWIYNTSNLASGVPARFSGSGSGTSYSLTISSMEAEDAAS YFCHQWRSYPPTLGAGTKLELK |
| 4A8 murine | Heavy chain variable | 26 | QVQLKQSGPGLVQPSQSLSITCTVSGFSLTSYGVHWVRQSPG KGLEWLGVIWSGGITDYNAAFKSRLSISKDNSKSQVFFKMNS LQANDTAIYFCARLGFYAMDYWGQGTSVTVSS |
| 4A8 murine | Light chain variable | 28 | QIVLTQSPAIMSASPGEKVTMTCSANSSVSYMHWYQQKSGTS PKRWIYDTSKLASGVPARFSGSGSGTSYSLTISSMGAEDAAT YYCQQWSSNPWTFGGGTKLEIK |
| 8H4 murine | Heavy chain variable | 30 | EVKLVESGGGLVKPGGSLKLSCAASGFTFRSYGMSWARQIPE KRLEWVASISSGGTTYYLGSVQGRFTISRDNARNILYLQMSSL RSEDTAMYYCARGYDAGFAYWGQGTLVSVSE |
| 8H4 murine | Light chain variable | 32 | DIVLTQSPASLAVSLGQRATISCRASQSVSTSSYSYMHWYQQ KPGQPPKLLIKYASNLESGVPARFSGSGSGTDFTLNIHPVEEE DTATYYCQNSWEIPYTFGGGTKLEIK |
| 8H3 murine | Heavy chain variable | 34 | EVQLQESGPSLVKPSQTLSLTCSVTGDSITSGYWTWIRKFPGN KLEYMGYISYTGSTYYNPSLKSRISISRDTSKSQYYLQLNSVT TEDTATYYCARQRDWLGFAYWGQGTLVTVSA |
| 8H3 murine | Light chain variable | 36 | DIVMTQTPSSLAVSLGEKVTMSCKSSQSLLYSSNQKNSLAWY QQKPGQSPKLLIYWASNRESGVPDRFTGSSSGTDFTLTISSVK AEDLAVYYCQQYYSYPLTFGAGTKLELK |
| 15F1 murine | Heavy chain variable | 38 | EEKLVESGGGLVKPGGSLKLSCAASGFSFSSYGMSWVRQTPE KRLEWVASISSGGSIYYPDSVKGRFTISRDNARNILYLQMSSL RSEDTAMYYCARGYDAGFAFWGQGTLVTASA |
| 15F1 murine | Light chain variable | 40 | DIVLTQSPASLAVSLGQRATISCRASQSVSTSSYSYVHWYQQ KPGQPPKLLIKYASNLESGVPARFSGSGSGTDFTLNIHPVEEE DTATYYCQHSWEIPYTFGGGTKLEIK |
| 5G11 humanized | Heavy chain variable | 42 | QITLKESGPTLVKPTQTLTLTCTVSGFSLSTYGVHWIRQPPGK ALEWLGVIWRGVTTDYNAAFMSRLTITKDNSKNQVVLTMN NMDPVDTATYYCARLGFYAMDYWGQGTLVTVSS |
| 5G11 humanized | Light chain variable | 44 | DIQMTQSPSSLSASVGDRVTITCKASQSVSNDVAWYQQKPGK APKLLIYYAANRYTGVPDRFSGSGYGTDFTFTISSLQPEDIAT YFCQQDYTSPYTFGQGTKLEIK |
| 13C5 humanized | Heavy chain variable | 46 | EVQLVESGGGLVKPGGSLRLSCAASGFIFRSYGMSWVRQAP GKGLEWVASISSGGSTYYPDSVKGRFTISRDNAKNSLYLQMN SLRAEDTAVYDCARGYDSGFAYWGQGTLVTVSS |
| 13C5 humanized | Light chain variable | 48 | DIVLTQSPASLAVSPGQRATITCRASQSVSTSSSSFMHWYQQK PGQPPKLLIKYASNLESGVPARFSGSGSGTDFTLTINPVEAND TANYYCQHSWEIPYTFGQGTKLEIK |

TABLE 3-continued

Heavy chain and light chain variable region and full length heavy and light chain amino acid sequences

| Name | Region | SEQ ID NO | Sequence |
|---|---|---|---|
| Chimeric 8C6-IgG4 (F234A/ L235A) | Full length heavy chain (IgG4) | 50 | QVQLKQSGPGLVQPSQSLSITCTVSGFSLTSYGVHWVRQSPG KGLEWLGVIWSGGVTDYNAAFISRLSISKDNSKSQVFFKMNS LQANDTAIYYCARLGFYAMDYWGQGTSVTVSSASTKGPSVF PLAPCSRSTSESTAALGCLVKDYFPEPVTVSWNSGALTSGVH TFPAVLQSSGLYSLSSVVTVPSSSLGTKTYTCNVDHKPSNTKV DKRVESKYGPPCPPCPAPEAAGGPSVFLFPPKPKDTLMISRTP EVTCVVVDVSQEDPEVQFNWYVDGVEVHNAKTKPREEQFN STYRVVSVLTVLHQDWLNGKEYKCKVSNKGLPSSIEKTISKA KGQPREPQVYTLPPSQEEMTKNQVSLTCLVKGFYPSDIAVEW ESNGQPENNYKTTPPVLDSDGSFFLYSRLTVDKSRWQEGNVF SCSVMHEALHNHYTQKSLSLSLG |
| Chimeric 8C6 | Full length light chain | 52 | SIVMTQTPKFLLVSAGDRVTITCKASQSVSNDVGWYQQKPG QSPKLLIYYASNRYSGVPDRFTGSGYGTDFTFTISTVQAEDLA VYFCQQDYTSPYTFGGGTKLEIKRTVAAPSVFIFPPSDEQLKS GTASVVCLLNNFYPREAKVQWKVDNALQSGNSQESVTEQDS KDSTYSLSSTLTLSKADYEKHKVYACEVTHQGLSSPVTKSFN RGEC |
| Chimeric 8H4-IgG4 (F234A/ L235A) | Full length heavy chain (IgG4) | 54 | EVKLVESGGGLVKPGGSLKLSCAASGFTFRSYGMSWARQIPE KRLEWVASISSGGTTYYLGSVQGRFTISRDNARNILYLQMSSL RSEDTAMYYCARGYDAGFAYWGQGTLVSVSSASTKGPSVFP LAPCSRSTSESTAALGCLVKDYFPEPVTVSWNSGALTSGVHT FPAVLQSSGLYSLSSVVTVPSSSLGTKTYTCNVDHKPSNTKV DKRVESKYGPPCPPCPAPEAAGGPSVFLFPPKPKDTLMISRTP EVTCVVVDVSQEDPEVQFNWYVDGVEVHNAKTKPREEQFN STYRVVSVLTVLHQDWLNGKEYKCKVSNKGLPSSIEKTISKA KGQPREPQVYTLPPSQEEMTKNQVSLTCLVKGFYPSDIAVEW ESNGQPENNYKTTPPVLDSDGSFFLYSRLTVDKSRWQEGNVF SCSVMHEALHNHYTQKSLSLSLG |
| Chimeric 8H4 | Full length light chain | 56 | DIVLTQSPASLAVSLGQRATISCRASQSVSTSSYSYMHWYQQ KPGQPPKLLIKYASNLESGVPARFSGSGSGTDFTLNIHPVEEE DTATYYCQNSWEIPYTFGGGTKLEIKRTVAAPSVFIFPPSDEQ LKSGTASVVCLLNNFYPREAKVQWKVDNALQSGNSQESVTE QDSKDSTYSLSSTLTLSKADYEKHKVYACEVTHQGLSSPVTK SFNRGEC |
| Chimeric 5G11-IgG1 (D265A) | Full length heavy chain (IgG1) | 58 | QVQLKQSGPGLVQPSQSLSITCTVSGFSLTTYGVHWVRQSPG KGLEWLGVIWRGVTTDYNAAFMSRLTITKDNSKSQVFFKMN SLQANDTAIYYCARLGFYAMDYWGQGTSVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLGGPSVFLFPPKPKDTLMI SRTPEVTCVVVAVSHEDPEVKFNWYVDGVEVHNAKTKPREE QYASTYRVVSVLTVLHQDWLNGKEYKCKVSNKALPAPIEKT ISKAKGQPREPQVYTLPPSRDELTKNQVSLTCLVKGFYPSDIA VEWESNGQPENNYKTTPPVLDSDGSFFLYSKLTVDKSRWQQ GNVFSCSVMHEALHNHYTQKSLSLSPGK |
| Chimeric 5G11-IgG4 (F234A/ L235A) | Full length heavy chain (IgG4) | 60 | QVQLKQSGPGLVQPSQSLSITCTVSGFSLTTYGVHWVRQSPG KGLEWLGVIWRGVTTDYNAAFMSRLTITKDNSKSQVFFKMN SLQANDTAIYYCARLGFYAMDYWGQGTSVTVSSASTKGPSV FPLAPCSRSTSESTAALGCLVKDYFPEPVTVSWNSGALTSGV HTFPAVLQSSGLYSLSSVVTVPSSSLGTKTYTCNVDHKPSNTK VDKRVESKYGPPCPPCPAPEAAGGPSVFLFPPKPKDTLMISRT PEVTCVVVDVSQEDPEVQFNWYVDGVEVHNAKTKPREEQF NSTYRVVSVLTVLHQDWLNGKEYKCKVSNKGLPSSIEKTISK AKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLG |
| Chimeric 5G11 | Full length light chain | 62 | SIVMTQTPKFLLVSAGDRVTITCKASQSVSNDVAWYQQKPG QSPKLLIYYAANRYTGVPDRFTGSGYGTDFTFTISIVQAEDLA VYFCQQDYTSPYTFGGGTKLEIKRTVAAPSVFIFPPSDEQLKS GTASVVCLLNNFYPREAKVQWKVDNALQSGNSQESVTEQDS KDSTYSLSSTLTLSKADYEKHKVYACEVTHQGLSSPVTKSFN RGEC |
| Chimeric 13C5-IgG1 (D265A) | Full length heavy chain | 64 | EVKLVESGGGLVKPGGSLKLSCAASGFIFRSYGMSWVRQTPE KRLEWVASISSGGSTYYPDSVKGRFTISRDNARNILYLQMSSL RSEDTAMYDCARGYDSGFAYWGQGTLVTVSSASTKGPSVFP LAPSSKSTSGGTAALGCLVKDYFPEPVTVSWNSGALTSGVHT |

TABLE 3-continued

Heavy chain and light chain variable region and full length heavy and light chain amino acid sequences

| Name | Region | SEQ ID NO | Sequence |
|---|---|---|---|
| | (IgG1) | | FPAVLQSSGLYSLSSVVTVPSSSLGTQTYICNVNHKPSNTKVD KKVEPKSCDKTHTCPPCPAPELLGGPSVFLFPPKPKDTLMISR TPEVTCVVVAVSHEDPEVKFNWYVDGVEVHNAKTKPREEQ YASTYRVVSVLTVLHQDWLNGKEYKCKVSNKALPAPIEKTIS KAKGQPREPQVYTLPPSRDELTKNQVSLTCLVKGFYPSDIAV EWESNGQPENNYKTTPPVLDSDGSFFLYSKLTVDKSRWQQG NVFSCSVMHEALHNHYTQKSLSLSPGK |
| Chimeric 13C5-IgG4 (F234A/L235A) | Full length heavy chain (IgG4) | 66 | EVKLVESGGGLVKPGGSLKLSCAASGFIFRSYGMSWVRQTPE KRLEWVASISSGGSTYYPDSVKGRFTISRDNARNILYLQMSSL RSEDTAMYDCARGYDSGFAYWGQGTLVTVSSASTKGPSVFP LAPCSRSTSESTAALGCLVKDYFPEPVTVSWNSGALTSGVHT FPAVLQSSGLYSLSSVVTVPSSSLGTKTYTCNVDHKPSNTKV DKRVESKYGPPCPPCPAPEAAGGPSVFLFPPKPKDTLMISRTP EVTCVVVDVSQEDPEVQFNWYVDGVEVHNAKTKPREEQFN STYRVVSVLTVLHQDWLNGKEYKCKVSNKGLPSSIEKTISKA KGQPREPQVYTLPPSQEEMTKNQVSLTCLVKGFYPSDIAVEW ESNGQPENNYKTTPPVLDSDGSFFLYSRLTVDKSRWQEGNVF SCSVMHEALHNHYTQKSLSLSLG |
| Chimeric 13C5 | Full length light chain | 68 | DIVLTQSPASLAVSLGQRATISCRASQSVSTSSSSFMHWYQQK PGQPPKLLIKYASNLESGVPARFSGSGSGTDFTLNIHPVEEEDT ATYYCQHSWEIPYTFGGGTKLEIKRTRTVAAPSVFIFPPSDEQ LKSGTASVVCLLNNFYPREAKVQWKVDNALQSGNSQESVTE QDSKDSTYSLSSTLTLSKADYEKHKVYACEVTHQGLSSPVTK SFNRGEC |
| Humanized 5G11-IgG1 (D265A) | Full length heavy chain (IgG1) | 70 | QITLKESGPTLVKPTQTLTLTCTVSGFSLSTYGVHWIRQPPGK ALEWLGVIWRGVTTDYNAAFMSRLTITKDNSKNQVVLTMN NMDPVDTATYYCARLGFYAMDYWGQGTLVTVSSASTKGPS VFPLAPSSKSTSGGTAALGCLVKDYFPEPVTVSWNSGALTSG VHTFPAVLQSSGLYSLSSVVTVPSSSLGTQTYICNVNHKPSNT KVDKKVEPKSCDKTHTCPPCPAPELLGGPSVFLFPPKPKDTL MISRTPEVTCVVVAVSHEDPEVKFNWYVDGVEVHNAKTKPR EEQYNSTYRVVSVLTVLHQDWLNGKEYKCKVSNKALPAPIE KTISKAKGQPREPQVYTLPPSRDELTKNQVSLTCLVKGFYPSD IAVEWESNGQPENNYKTTPPVLDSDGSFFLYSKLTVDKSRWQ QGNVFSCSVMHEALHNHYTQKSLSLSPGK |
| Humanized 5G11-IgG4 (F234A/L235A) | Full length heavy chain (IgG4) | 72 | QITLKESGPTLVKPTQTLTLTCTVSGFSLSTYGVHWIRQPPGK ALEWLGVIWRGVTTDYNAAFMSRLTITKDNSKNQVVLTMN NMDPVDTATYYCARLGFYAMDYWGQGTLVTVSSASTKGPS VFPLAPCSRSTSESTAALGCLVKDYFPEPVTVSWNSGALTSG VHTFPAVLQSSGLYSLSSVVTVPSSSLGTKTYTCNVDHKPSNT KVDKRVESKYGPPCPPCPAPEAAGGPSVFLFPPKPKDTLMISR TPEVTCVVVDVSQEDPEVQFNWYVDGVEVHNAKTKPREEQF NSTYRVVSVLTVLHQDWLNGKEYKCKVSNKGLPSSIEKTISK AKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLG |
| Humanized 5G11 | Full length light chain | 74 | DIQMTQSPSSLSASVGDRVTITCKASQSVSNDVAWYQQKPGK APKLLIYYAANRYTGVPDRFSGSGYGTDFTFTISSLQPEDIAT YFCQQDYTSPYTFGQGTKLEIKRTVAAPSVFIFPPSDEQLKSG TASVVCLLNNFYPREAKVQWKVDNALQSGNSQESVTEQDSK DSTYSLSSTLTLSKADYEKHKVYACEVTHQGLSSPVTKSFNR GEC |
| Humanized 13C5-IgG1 (D265A) | Full length heavy chain (IgG1) | 76 | EVQLVESGGGLVKPGGSLRLSCAASGFIFRSYGMSWVRQAP GKGLEWVASISSGGSTYYPDSVKGRFTISRDNAKNSLYLQMN SLRAEDTAVYDCARGYDSGFAYWGQGTLVTVSSASTKGPSV FPLAPSSKSTSGGTAALGCLVKDYFPEPVTVSWNSGALTSGV HTFPAVLQSSGLYSLSSVVTVPSSSLGTQTYICNVNHKPSNTK VDKKVEPKSCDKTHTCPPCPAPELLGGPSVFLFPPKPKDTLMI SRTPEVTCVVVAVSHEDPEVKFNWYVDGVEVHNAKTKPREE QYNSTYRVVSVLTVLHQDWLNGKEYKCKVSNKALPAPIEKT ISKAKGQPREPQVYTLPPSRDELTKNQVSLTCLVKGFYPSDIA VEWESNGQPENNYKTTPPVLDSDGSFFLYSKLTVDKSRWQQ GNVFSCSVMHEALHNHYTQKSLSLSPGK |
| Humanized 13C5-IgG4 (F234A/ | Full length heavy | 78 | EVQLVESGGGLVKPGGSLRLSCAASGFIFRSYGMSWVRQAP GKGLEWVASISSGGSTYYPDSVKGRFTISRDNAKNSLYLQMN SLRAEDTAVYDCARGYDSGFAYWGQGTLVTVSSASTKGPSV |

TABLE 3-continued

Heavy chain and light chain variable region and full length heavy and light chain amino acid sequences

| Name | Region | SEQ ID NO | Sequence |
|---|---|---|---|
| L235A) | chain (IgG4) | | FPLAPCSRSTSESTAALGCLVKDYFPEPVTVSWNSGALTSGV HTFPAVLQSSGLYSLSSVVTVPSSSLGTKTYTCNVDHKPSNTK VDKRVESKYGPPCPPCPAPEAAGGPSVFLFPPKPKDTLMISRT PEVTCVVVDVSQEDPEVQFNWYVDGVEVHNAKTKPREEQF NSTYRVVSVLTVLHQDWLNGKEYKCKVSNKGLPSSIEKTISK AKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLG |
| Humanized 13C5 | Full length light chain | 80 | DIVLTQSPASLAVSPGQRATITCRASQSVSTSSSSFMHWYQQK PGQPPKLLIKYASNLESGVPARFSGSGSGTDFTLTINPVEAND TANYYCQHSWEIPYTFGQGTKLEIKRTVAAPSVFIFPPSDEQL KSGTASVVCLLNNFYPREAKVQWKVDNALQSGNSQESVTEQ DSKDSTYSLSSTLTLSKADYEKHKVYACEVTHQGLSSPVTKS FNRGEC |

In one embodiment, the invention provides anti-PD-L1 antibodies that comprise the light chain CDRs and heavy chain CDRs of antibodies 13C5, 5G9, 5G11, 8C6, 7B4, 4D1, 4A8, 8H4, 8H3, and/or 15F1. The person of skill in the art will understand that the heavy and light chain CDRs of the antibodies provided herein may be independently selected, or mixed and matched, to form an antibody or binding fragment thereof comprising any heavy chain CDR1, CDR2, and CDR3; and any light chain CDR1, CDR2, and CDR3 from the antibodies provided herein. Thus, the invention provides anti-PD-L1 antibodies that comprise a heavy chain CDR1 comprising an amino acid sequence selected from the group consisting of SEQ ID NOs: 81, 87, 93, 99, 105, 111, 117, 123, 129, and 135; a heavy chain CDR2 comprising an amino acid sequence selected from the group consisting of SEQ ID NOs: 82, 88, 94, 100, 106, 112, 118, 124, 130, and 136; a heavy chain CDR3 comprising an amino acid sequence selected from the group consisting of SEQ ID NOs: 83, 89, 95, 101, 107, 113, 119, 125, 131, and 137; a light chain CDR1 comprising an amino acid sequence selected from the group consisting of SEQ ID NOs: 84, 90, 96, 102, 108, 114, 120, 126, 132, and 138; a light chain CDR2 comprising an amino acid sequence selected from the group consisting of SEQ ID NOs: 85, 91, 97, 103, 109, 115, 121, 127, 133, and 139; and a light chain CDR3 comprising an amino acid sequence selected from the group consisting of SEQ ID NOs: 86, 92, 98, 104, 110, 116, 122, 128, 134, and 140. In one embodiment, the present invention provides anti-PD-L1 antibodies comprising heavy and light chain CDR regions comprising amino acid sequences having at least 75%, at least 80%, at least at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% homology to the corresponding light or heavy chain CDR1, CDR2, or CDR3 provided herein. In one embodiment, the present invention provides anti-PD-L1 antibodies comprising heavy and light chain CDR regions comprising amino acid sequences having 1, 2, 3, 4, 5, or 6 amino acid substitutions, deletions, or insertions relative to the corresponding light or heavy chain CDR1, CDR2, or CDR3 provided herein.

In one embodiment, the invention provides anti-PD-L1 antibodies that comprise a variable heavy chain of an antibody selected from the group consisting of 13C5, 5G9, 5G11, 8C6, 7B4, 4D1, 4A8, 8H4, 8H3, and/or 15F1 and a variable light chain of an antibody selected from the group consisting of 13C5, 5G9, 5G11, 8C6, 7B4, 4D1, 4A8, 8H4, 8H3, and/or 15F1. In one embodiment, the antibodies and fragments provided herein comprise a heavy chain variable region comprising an amino acid sequence that is at least 75%, at least 80%, at least at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% homology to a heavy chain variable region selected from the group consisting of SEQ ID NOs: 2, 6, 10, 14, 18, 22, 26, 30, 34, 38, 42, and 46. In one embodiment, the antibodies and fragments provided herein comprise a heavy chain variable region comprising an amino acid sequence according to SEQ ID NO: 2, 6, 10, 14, 18, 22, 26, 30, 34, 38, 42, 46, or a variant thereof, wherein the variant comprises 1, 2, 3, 4, 5, 6, 7, 8, 9, or 10 amino acid substitutions or deletions, or a combination thereof. In a further embodiment, the amino acid substitutions are conservative substitutions.

In one embodiment, the antibodies and fragments provided herein comprise a light chain variable region comprising an amino acid sequence that is at least 75%, at least 80%, at least at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% homology to a light chain variable region selected from the group consisting of SEQ ID NOs: 4, 8, 12, 16, 20, 24, 28, 32, 36, 40, 44, or 48. In one embodiment, the antibodies and fragments provided herein comprise a light chain variable region comprising an amino acid sequence according to SEQ ID NO: 4, 8, 12, 16, 20, 24, 28, 32, 36, 40, 44, 48, or a variant thereof, wherein the variant comprises 1, 2, 3, 4, 5, 6, 7, 8, 9, 10, or more amino acid substitutions, insertions, or deletions, or a combination thereof. In a further embodiment, the amino acid substitutions are conservative substitutions.

The anti-PD-L1 antibodies disclosed herein having one or more amino acid substitution, insertion, deletion, or combination thereof in the CDR or variable light or heavy chain region retain the biological activity of the corresponding anti-PD-L1 antibody that does not have an amino acid substitution, insertion, or deletion. Thus, the variant anti- PD-L1 antibodies provided herein retain binding to PD-L1. Percent homology, as used herein, refers to the number of identical amino acid sequences shared by two reference sequences, divided by the total number of amino acid positions, multiplied by 100.

In some embodiments, the anti-PD-L1 antibodies provided herein comprise conservative amino acid substitutions. The person of skill in the art will recognize that a conservative amino acid substitution is a substitution of one amino acid with another amino acid that has a similar structural or chemical properties, such as, for example, a similar side chain. Exemplary conservative substitutions are described in the art, for example, in Watson et al., *Molecular Biology of the Gene*, The Bengamin/Cummings Publication Company, 4$^{th}$ Ed. (1987).

The skilled person will understand that the variable light and variable heavy chains may be independently selected, or mixed and matched, from the antibodies provided herein. Thus, the present invention provides anti-PD-L1 antibodies comprising a heavy chain variable region having at least 80% homology to an amino acid sequence selected from the group consisting of SEQ ID NOs: 2, 6, 10, 14, 18, 22, 26, 30, 34, 38, 42, and 46; and a light chain variable region having at least 80% homology to an amino acid sequence selected from the group consisting of SEQ ID NOs: 4, 8, 12, 16, 20, 24, 28, 32, 36, 40, 44, and 48.

In one embodiment, the present invention provides antibodies that bind to the same epitope as any one of the exemplary antibodies disclosed herein. Thus, in one embodiment, the present invention provides antibodies that compete for binding to PD-L1 with the exemplary antibodies provided herein.

The anti-PD-L1 antibodies and fragments thereof provided herein may further comprise Fc region modifications to alter effector functions. Fc modifications may be amino acid insertions, deletions, or substitutions, or may be chemical modifications. For example, Fc region modifications may be made to increase or decrease complement binding, to increase or decrease antibody-dependent cellular cytotoxicity, or to increase or decrease the half life of the antibody. Some Fc modifications increase or decrease the affinity of the antibody for an Fcγ receptor such as FcγRT, FcγRII, FcγRIII, or FcRn. Various Fc modifications have been described in the art, for example, in Shields et al., *J Biol. Chem* 276; 6591 (2001); Tai et al. *Blood* 119; 2074 (2012); Spiekermann et al. *J Exp. Med* 196; 303 (2002); Moore et al. *mAbs* 2:2; 181 (2010); Medzihradsky *Methods in Molecular Biology* 446; 293 (2008); Mannan et al. *Drug Metabolism and Disposition* 35; 86 (2007); and Idusogie et al. *J Immunol* 164; 4178 (2000). In some embodiments, Fc region glycosylation patters are altered. In other embodiments, the Fc region is modified by pegylation (e.g., by reacting the antibody or fragment thereof with polyethylene glycol (PEG).

In one embodiment, the antibodies or fragments thereof provided herein are immunoconjugates comprising an anti-PD-L1 antibody or fragment thereof and further comprising an agent selected from the group including an additional therapeutic agent, a cytotoxic agent, an immunoadhesion molecule, and an imaging agent. In some embodiments, the imaging agent is selected from the group consisting of a radiolabel, an enzyme, a fluorescent label, a luminescent label, a bioluminescent label, a magnetic label, and biotin. In some embodiments, the imaging agent is a radiolabel selected from the group consisting of: $^{3}$H, $^{14}$C, $^{35}$S, $^{62}$Cu, $^{64}$Cu, $^{89}$Zr, $^{90}$Y, $^{99}$Tc, $^{111}$In, $^{125}$I, $^{131}$I, $^{177}$Lu, $^{166}$Ho, and $^{153}$Sm. In some embodiments, the therapeutic agent or cytotoxic agent is selected from the group including a chemotherapeutic agent, an immunosuppressive agent, an immuno-stimulatory agent, an anti-metabolite, an alkylating agent, an antibiotic, a growth factor, a cytokine, an anti-angiogenic agent, an anti-mitotic agent, an anthracycline, a toxin, and an apoptotic agent. In some embodiments, the binding protein is conjugated directly to the agent. In other embodiments, the binding protein is conjugated to the agent via a linker. Suitable linkers include, but are not limited to, amino acid and polypeptide linkers disclosed herein. Linkers may be cleavable or non-cleavable.

In one embodiment, the present invention provides bispecific or multispecific antibodies specific for PD-L1 and at least one other antigen or epitope. The anti-PD-L1 antibodies and fragments thereof provided herein may be tested for binding to PD-L1 using the binding assays provided herein, or any other binding assay known in the art.

Unless otherwise stated, the practice of the present invention employs conventional molecular biology, cell biology, biochemistry, and immunology techniques that are well known in the art and described, for example, in Methods in Molecular Biology, Humana Press; Molecular Cloning: A Laboratory Manual, second edition (Sambrook et al., 1989), Current Protocols in Immunology (J. E. Coliganet al., eds., 1991); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Phage display: a laboratory manual (C. Barbas III et al, Cold Spring Harbor Laboratory Press, 2001); and Using antibodies: a laboratory manual (E. Harlow and D. Lane (Cold Spring Harbor Laboratory Press, 1999).

In one aspect the present invention provides methods for treating a subject for a disease or condition responsive to enhancing, stimulating, or eliciting an immune response. As used herein, the terms "treatment" or "treating" refers to both therapeutic treatment and prophylactic or preventive measures. Subjects in need of treatment include those subjects that already have the disease or condition, as well as those that may develop the disease or condition and in whom the object is to prevent, delay, or diminish the disease or condition. As used herein, the term "subject" denotes a mammal, such as a rodent, a feline, a canine, and a primate. Preferably, a subject according to the invention is a human.

The term "therapeutically effective amount," as used herein, refers to the amount of a compound or composition that is necessary to provide a therapeutic and/or preventative benefit to the subject.

In one aspect, the antibodies and antigen binding fragments thereof are useful in the treatment of solid or non-solid tumors. Thus, in one aspect, the present invention provides methods for treatment of cancer. "Cancer" as used herein refers to the physiological condition in mammals that is typically characterized by unregulated cell growth. Examples of cancer include but are not limited to carcinoma, lymphoma, blastoma, sarcoma (including liposarcoma, osteogenic sarcoma, angiosarcoma, endotheliosarcoma, leiomyosarcoma, chordoma, lymphangiosarcoma, lymphangioendotheliosarcoma, rhabdomyosarcoma, fibrosarcoma, myxosarcoma, chondrosarcoma), neuroendocrine tumors, mesothelioma, synovioma, schwanoma, meningioma, adenocarcinoma, melanoma, and leukemia or lymphoid malignancies. More particular examples of such cancers include squamous cell cancer (e.g. epithelial squamous cell cancer), Hodgkin's lymphoma; non-Hodgkin's lymphomas (Burkitt's lymphoma, small lymphocytic lymphoma/chronic lymphocytic leukemia, mycosis fungoides, mantle cell lymphoma, follicular lymphoma, diffuse large B-cell lymphoma, marginal zone lymphoma, hairy cell leukemia and lymphoplamacytic leukemia), tumors of lymphocyte precursor cells, including B-cell acute lymphoblastic leukemia/lymphoma, and T-cell acute lymphoblastic leukemia/lymphoma, thymoma, tumors of the mature T and NK cells, including peripheral T-cell leukemias, adult T-cell leukemia/T-cell lymphomas and large granular lymphocytic leukemia, Langerhans cell histocytosis, myeloid neoplasias such as acute myelogenous leukemias, including AML with maturation, AML, without differentiation, acute promyelocytic leukemia, acute myelomonocytic leukemia, and acute monocytic leukemias, myelodysplastic syndromes, and chronic myeloproliferative disorders, including chronic myelogenous leukemia, B-cell acute lymphoblastic leukemia/lymphoma, T-cell acute lymphoblastic leukemia/lymphoma, lung cancer including small-cell lung cancer, non-small cell lung cancer, adenocarcinoma of the lung and squamous carcinoma of the lung, small cell lung carcinoma, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophageal cancer, tumors of the biliary tract, Ewing's tumor, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, testicular tumor, lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenstrom's macroglobulinemia, myelodysplastic disease, heavy chain disease, neuroendocrine tumors, Schwanoma, and other carcinomas, as well as head and neck cancer.

In one embodiment, the antibodies and fragments thereof provided herein are useful in the treatment of diseases caused by infectious agents. Infectious agents include, but are not limited to, bacterial, mycological, parasitic, and viral agents. Examples of such infectious agents include the following: *staphylococcus*, methicillin-resistant *staphylococcus aureus, Escherichia coli*, streptococcaceae, neisseriaaceae, cocci, enterobacteriaceae, *enterococcus*, vancomycin-resistant *enterococcus, cryptococcus*, histoplasmosis, *aspergillus*, pseudomonadaceae, vibrionaceae, *campylobacter*, pasteurellaceae, *bordetella, francisella, brucella*, legionellaceae, bacteroidaceae, gram-negativebacilli, *clostridium, corynebacterium, propionibacterium*, gram-positive *bacilli*, anthrax, *actinomyces, nocardia, mycobacterium, treponema, borrelia, leptospira, mycoplasma, ureaplasma, rickettsia*, chlamydiae, *candida*, systemic mycoses, opportunistic mycoses, protozoa, nematodes, trematodes, cestodes, adenoviruses, herpesviruses (including, for example, herpes simplex virus and Epstein Barr virus, and herpes zoster virus), poxviruses, papovaviruses, hepatitis viruses, (including, for example, hepatitis B virus and hepatitis C virus), papilloma viruses, orthomyxoviruses (including, for example, influenza A, influenza B, and influenza C), paramyxoviruses, coronaviruses, picornaviruses, reoviruses, togaviruses, flaviviruses, bunyaviridae, rhabdoviruses, rotavirus, respiratory syncitial virus, human immunodeficiency virus and retroviruses. Exemplary infectious diseases include but are not limited to candidiasis, candidemia, aspergillosis, streptococcal pneumonia, streptococcal skin and oropharyngeal conditions, gram negative sepsis, tuberculosis, mononucleosis, influenza, respiratory illness caused by Respiratory Syncytial Virus, malaria, schistosomiasis, and trypanosomiasis.

In one embodiment, the antibodies and fragments thereof provided herein are useful in the treatment of diseases mediated by T-helper type 2 (Th2) T cells, such as, for example, asthma, allergy, or graft versus host disease.

In one embodiment, the antibodies and fragments thereof provided herein are useful in for the stimulation of an immune response in a subject in need thereof. For example, in one embodiment, the anti-PD-L1 antibodies and fragments thereof may be administered in conjunction with an antigen of interest for the purpose of eliciting an immune response to said antigen. An antigen of interest may be an antigen associated with a pathogen such as a virus or bacterium. Thus, in one embodiment, the present invention provides a vaccine comprising an anti-PD-L1 antibody and an antigen, wherein the vaccine elicits an antigen-specific immune response.

In one embodiment, the anti-PD-L1 antibodies provided herein modulate regulatory T cell function. CD4+ CD25+ regulatory T cells are lymphocytes that suppress or reduce the effects of effector T cell functions. The terms "regulatory T cell" and "Treg" are used interchangeably herein. In one embodiment, the anti-PD-L1 antibodies provided herein prevent or reverse the inhibitory effects of regulatory T cells on effector T cell cytokine production. For example, in one embodiment, the anti-PD-L1 antibodies provided herein restore the capacity for IFNγ production to effector T cells in contact with regulatory T cells.

In one embodiment, the antibodies and fragments thereof disclosed herein may be administered to the subject by at least one route selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intratympanic, intrauterine, intravesical, intravitreal, bolus, subconjunctival, vaginal, rectal, buccal, sublingual, intranasal, intratumoral, and transdermal.

In one embodiment, the antibodies and fragments thereof disclosed herein may be administered to a subject in need thereof in combination with one or more additional therapeutic agent. In one embodiment, the antibodies and fragments thereof may be administered to a subject before, during, and/or after administration to the subject of the additional therapeutic agent. In one embodiment, the additional therapeutic agent is a chemotherapeutic agent, radiotherapeutic agent, cytokine, antibody or fragment thereof, or any other additional therapeutic that is indicated for the disease to be treated. In one embodiment, the anti-PD-L1 antibody and the additional therapeutic agent exhibit therapeutic synergy when administered together, whether concurrently or sequentially. In one embodiment, the anti-PD-L1 antibody and the additional therapeutic agent are administered in separate formulations. In another embodiment, the anti-PD-L1 antibody and the additional therapeutic agent are administered in the same formulation. In one embodiment, the anti-PD-L1 antibodies and fragments provided herein enhance the immune modulating effect of the one or more additional therapeutic agent. In another embodiment, the one or more additional therapeutic agent enhances the effect of the anti-PD-L1 antibody or fragment thereof.

The present invention provides isolated antibodies and antigen binding fragments thereof, and nucleic acids encoding such antibodies and fragments, as well as compositions comprising such isolated antibodies, fragments, and nucleic acids. The term "isolated" refers to a compound of interest (e.g., an antibody or nucleic acid) that has been separated from its natural environment. The present invention further provides pharmaceutical compositions comprising the isolated antibodies or fragments thereof, or nucleic acids encoding such antibodies or fragments, and further comprising one or more pharmaceutically acceptable carrier. Pharmaceutically acceptable carriers include, for example, excipients, diluents, encapsulating materials, fillers, buffers, or other agents.

The use of the singular includes the plural unless specifically stated otherwise. The word "a" or "an" means "at least one" unless specifically stated otherwise. The use of "or" means "and/or" unless stated otherwise. The meaning of the phrase "at least one" is equivalent to the meaning of the phrase "one or more." Furthermore, the use of the term "including," as well as other forms, such as "includes" and "included," is not limiting. Also, terms such as "element" or "component" encompass both elements or components comprising one unit and elements or components comprising more than one unit unless specifically stated otherwise.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of non-critical parameters that could be changed or modified to yield essentially similar results.

EXAMPLES

Example 1: Generation of hPD-L1 Monoclonal Antibody

Immunization of Mice with hPD-L1-HisTag and hPD-L1-mFc

To generate antibodies against the human PD-L1, cDNAs encoding the open reading frame of the extracellular domain of hPD-L1 fused with a histidine tag (hPD-L1-HisTag, SEQ ID NOs:143 and 144), mouse Fc (hPD-L1-mFc, SEQ ID NOs:145 and 146), and human Fc tag (hPD-L1-hFc, SEQ ID NO:147 and 148) were obtained by PCR and subcloned into expression vector pcDNA3.1 (Invitrogen CAT#:V-790), respectively. After transient expression in freestyle 293 cells, hPD-L1-HisTag was purified with NTA column (GE healthcare), hPD-L1-mFc and hPD-L1-hFc were purified with Protein G column (GE healthcare).

BALB/cJ mice were immunized subcutaneously every 2 weeks for 6 weeks with recombinant hPD-L1-HisTag protein (100 µg/mouse) or hPD-L1-mFc emulsified with an equal volume of Freund's complete/incomplete adjuvant. Three days before fusion, mice were boosted by intravenous injection of the antigen without adjuvant. Spleen cells ($1\times10^8$) from immunized mouse were fused with SP2/0 myeloma cells ($1.5\times10^7$) with PEG Hybri-Max (Sigma Inc., CAT#:7181). After fusion, the cells were distributed into 96-well plates at 0.1 ml per well and incubated at 37° C., 5% $CO_2$ incubator. On day 1, cells were fed by adding an additional 0.1 ml per well with media containing serum and HAT plus 2× methotrexate. On day 3 and day 7, 0.1 ml of media from each well was replaced with 0.1 ml of fresh HT media. The screening typically occurred between days 9-14, and culture supernatant was tested for antibody reacting with hPD-L1-hFc by ELISA.

To clone the selected hybridoma cell, limiting dilution was carried out four times. The hybridoma cells were cultured in Dulbecco's Modified Eagle's medium (GIBCO; Invitrogen Corporation, Carlsbad, Calif.) containing 10% fetal calf serum, 1% penicillin/streptomycin, 2% L-glutamine, and 1% adjusted $NaHCO_3$ solution. The selected hybridoma cells were then adapted in serum free culture medium and the antibody was purified from the supernatant using Protein-G column (GE healthcare). After washing with PBS, bound antibodies were eluted using 0.1 M Glycine pH3.0, followed by pH neutralization using 2.0 M Tris. Ultra-15 centrifugal concentrators (Amicon) were used for buffer exchanging and antibody concentrating.

Example 2: Anti-PD-L1 Antibodies cDNA Sequences Cloning and Humanization Cloning of Immunoglobulin cDNAs Total RNA isolated from the hybridoma cell line producing hPD-L1 antibody by RNeasy Mini Kit (Qiagen, CAT#: 74104) was used as the template to synthesize first-strand cDNA with SuperScript® II Reverse Transcriptase (Life Technology, CAT#:18064-14) according to the manufacturer's instructions. The cDNA product was then subjected to PCR in a 50 µl volume reaction mixture using degenerate mouse IgG primers (Kettleborough Calif., et al, European Journal of Immunology 23: 206-211 (1993), Strebe N, et al, Antibody Engineering 1:3-14 (2010)). The reaction was carried out in a S1000™ Thermal Cycler (Bio-Rad, CAT#: 184-2000) with 30 cycles of: 94° C., 1.5 minutes for denaturation; 50° C., 1 minutes for annealing; and 72° C., 1 minute for synthesis. At the end of the 30th cycle, the reaction mixture was incubated another 7 minutes at 72° C. for extension.

The PCR mixture was subjected to electrophoresis in a 1% agarose/Tris-Borate gel containing 0.5 µg/ml ethidium bromide. DNA fragments having the expected sizes (approximately 450 bp for the heavy chain and the light chain) were excised from the gel and purified. 3 µl of purified PCR product were cloned into the pMD-18T vector (Takara, CAT#:D101A) and transformed into One Shot® TOP10 chemically competent *E. coli* (Invitrogen, CAT#:C4040-03). Clones were screened by colony PCR using universal M13 forward and reverse primers, and 10 positive clones from each reaction were chosen for DNA sequencing in both directions using M13 forward and M13 reverse primers.

The heavy and light variable region sequences of antibodies m4A8 (SEQ ID NOs: 25-28), m4D1 (SEQ ID NOs: 21-24), m5G9 (SEQ ID NOs: 5-8), m5G11 (SEQ ID NOs: 9-12), m8C6 (SEQ ID NOs: 13-16), m8H3 (SEQ ID NOs: 33-36), m8H4 (SEQ ID NOs: 29-32), m7B4 (SEQ ID NOs: 17-20), m13C5 (SEQ ID NOs: 1-4) and m15F1 (SEQ ID NOs: 37-40) were amplified from the corresponding hybridoma clones. These antibodies showed desired functions, such as blocking PD-L1 binding to PD-1, and enhanced T cell activation and cytokine release.

Construction and Expression of Chimeric 5G11 and 13C5 Antibody

8C6, 8H4, 5G11 and 13C5 chimeric light chains (SEQ ID NOs: 52, 56, 62, and 68, respectively) were constructed by linking the PCR-cloned cDNAs of mouse VL regions to human kappa chain constant region, respectively. 8C6, 8H4, 5G11 and 13C5 chimeric heavy chains (SEQ ID NOs: 50 (8C6-IgG4), 54 (8H4-IgG4), 58 (5G11-IgG1), 60 (5G11-IgG4), 64 (13C5-IgG1), and 66 (13C5-IgG4)) were constructed by linking the PCR-cloned cDNAs of mouse VH regions to human IgG1 and IgG4 constant regions. The 5'ends of the mouse cDNA sequences were modified using PCR primers designed to add a leader sequence to both light chain and heavy chain.

Freestyle 293 cells (200 mL at $10^6$/mL) were transfected with 100 μg of each of the chimeric heavy and light chain expression plasmids and cultured for 6 days. The chimeric antibody in the supernatant was then purified with Protein-G column (GE healthcare). Binding of the chimeric antibody with PD-L1 was measured by ELISA and Biacore, and was shown to bind to PD-L1 with comparable affinity to that of the murine parent antibody.

Antibody Humanization Design

5G11 and 13C5 antibodies were humanized using CDR grafting approach (see, for example, U.S. Pat. No. 5,225,539). The light chain and heavy chain variable chain sequences of the murine antibody 5G11 and 13C5 were compared to those available in the Research Collaboratory for Structural Bioinformatics (RCSB) protein databank (http://www.ncbi.nlm.nih.gov/igblast/igblast.cgi). The model of 5G11 and 13C5 were generated respectively based on the VH and VL structure with the highest sequence homology.

The template human antibodies to be grafted with the complementary determining regions (CDRs) in the VH and VL of mouse 5G11 and 13C5 antibody were selected from human antibody germlines having high sequence homology with mouse 5G11 and 13C5 antibody by searching the international immunogenetics information system website (http://www.imgt.org/3Dstructure-DB/cgi/DomainGapAlign.cgi). For 5G11, the template human VH selected was a combination of IGHV2-5*10 and IGHJ4*01, and template human VL selected was a combination of IGKV1-33*01 and IGKJ2*01. For 13C5, the template human VH selected was a combination of IGHV3-21*04 and IGHJ4*01, and template human VL selected was a combination of IGKV7-3*01 and IGKJ2*01.

CDR amino acid sequences of the aforementioned template human antibodies were substituted by the CDRs of hybridoma (mouse) 5G11 (SEQ ID NOs 93-98) and 13C5 (SEQ ID NOs 81-86) antibodies. The frameworks of the above-mentioned template human antibody VH and VL were grafted with the necessary amino acid sequences from VH and VL of mouse 5G11 and 13C5 antibody to give a functional humanized antibody. As for VH and VL of 5G11 and 13C5, several sites of framework amino acid of the aforementioned template human antibody were backmutated to the corresponding amino acid sequences in mouse 5G11 and 13C5 antibody. For the light chain variable region of humanized 5G11 antibody, the amino acid at position 60 is mutated from Ser (S) to Asp (D), and the amino acid at position 67 is mutated from Ser (S) to Tyr (Y); and for the heavy chain variable region of humanized 5G11 antibody, the amino acid at position 24 is mutated from Phe (F) to Val (V), the amino acid at position 49 is mutated from Ala (A) to Gly (G), the amino acid at position 73 is mutated from Thr (T) to Asn (N), and the amino acid at position 83 is mutated from Thr (T) to Asn (N). For the light chain variable region of humanized 13C5, the amino acid at position 53 is mutated from Tyr (Y) to Lys (K); and for the heavy chain variable region of humanized 13C5, the amino acid at position 28 is mutated from Thr (T) to Ile (I), the amino acid at position 30 is mutated from Ser (S) to Arg (R), the amino acid at position 49 is mutated from Ser (S) to Ala (A), and the amino acid at position 94 is mutated from Tyr (Y) to Asp (D). The amino acid sequences of VH and VL of humanized 5G11 are provided as SEQ ID NOs:42 and 44, respectively; DNA sequences encoding the VH and VL of humanized 5G11 are provided as SEQ ID NOs: 41 and 43, respectively. The amino acid sequences of VH and VL of humanized 13C5 are provided as SEQ ID NOs: 46 and 48, respectively); DNA sequences encoding the VH and VL of humanized 13C5 are provided as SEQ ID NOs: 45 and 47, respectively.

The amino acid sequences of the full light chain for humanized antibodies 5G11 and 13C5 are provided as SEQ ID NOs: 74 and 80, respectively. The DNA sequences encoding the full length humanized 5G11 and 13C5 are provided as SEQ ID NOs: 73 and 79, respectively. IgG1 and IgG4 versions of the humanized 5G11 and 13C5 antibodies were produced. The IgG1 constant region carries D265A mutation (Clynes R, et al, Nature Medicine 6: 443-446 (2000)), while IgG4 constant region has F234A and L235A double mutation (Xu D, et al, Cellular Immunology 200: 16-26 (2000)). The DNA and amino acid sequences for the full length IgG1 heavy chain of humanized antibody 5G11-hIgG1 are provided as SEQ ID NOs: 69 and 70, respectively. The DNA and amino acid sequences for the full length IgG4 heavy chain of humanized antibody 5G11-hIgG4 are provided as SEQ ID NOs: 71 and 72, respectively. The DNA and amino acid sequences for the full length IgG1 heavy chain of humanized antibody 13C5-hIgG1 are provided as SEQ ID NOs: 75 and 76, respectively. The DNA and amino acid sequences for the full length IgG4 heavy chain of humanized antibody 13C5-hIgG4 are provided as SEQ ID NOs: 77 and 78, respectively.

Construction and Expression of Humanized 5G11 and 13C5 Antibody

DNA encoding humanized 5G11 and 13C5 antibody light chain and heavy chain was synthesized and cloned to the expression vector pcDNA3.1 (Invitrogen, CAT: #V-790). Freestyle 293 cells (200 mL at $10^6$/mL) were transfected with 100 μg of each of the humanized heavy and light chain expression plasmids and cultured for 6 days. The humanized antibody in the supernatant was then purified with Protein-G column (GE healthcare).

The binding kinetics between PD-L1 and PD-L1 antibodies were measured by Biacore analysis, which was performed at 25° C. on a Biacore3000 instrument and recorded with a data collection rate of 1 Hz. Polyclonal rabbit anti-mouse IgG (GE, BR-1008-38) was diluted with 10 mM pH 5.0 sodium acetate and immobilized onto reference and experiment flow cells of a CM5 biosensor chip to around 15000 RU using an amine coupling kit (GE, BR10050). In the beginning of each cycle, diluted test antibody (1.5 μg/mL) was injected over experiment flow cell for 1 minute to be captured. PD-L1 analyte series were prepared by diluting the stocks with running buffer to 100 nM followed by 2× serial dilution in the same buffer down to 0.78 nM. Analytes were injected in series over the reference and experiment flow cells for 3 minutes at a flow rate of 30 μL/minute. Running buffer (PBS with 0.05% P20) was allowed to flow over for 10 minutes at a flow rate of 30 μL/minute. At the end of each cycle, the biosensor surface was regenerated with 3 minutes injection of 10 mM pH1.7

Glycine-HCl buffer at a flow rate of 10 μL/minute. For each analyte sample injection (i.e. each cycle), binding responses obtained from the experimental biosensor surface were double referenced by subtracting simultaneously recorded responses from the reference surface followed by additional subtraction of responses from a single referenced running buffer sample. The association and dissociation rate constants (ka and kd) were determined simultaneously by fitting double-referenced sensorgrams of the entire titration series to Langmuir model (1:1) using Biaevaluation 4.0 software. The dissociation constant, KD, was calculated from the determined rate constants by the relation KD=kd/ka. The binding affinity of anti-PD-L1 antibodies with human PD-L1 and cynomolgus PD-L1 (cyno-PD-L1) are summarized in Table 4.

TABLE 4

PD-L1 binding affinity of anti-PD-L1 antibodies

| Selected Antibody | Antigen | KD (M) |
|---|---|---|
| m4A8 | Human PD-L1 | 2.33E−9 |
| m4D1 | Human PD-L1 | 4.39E−9 |
| m5G9 | Human PD-L1 | 4.78E−9 |
| m5G11 | Human PD-L1 | 1.90E−10 |
| m7B4 | Human PD-L1 | 6.01E−9 |
| m8H3 | Human PD-L1 | 6.60E−9 |
| m8H4 | Human PD-L1 | 4.56E−9 |
| m8C6 | Human PD-L1 | 1.53E−9 |
| m13C5 | Human PD-L1 | 1.35E−9 |
| m15F1 | Human PD-L1 | 3.59E−9 |
| ch5G11 | Human PD-L1 | 2.86E−10 |
| ch13C5 | Human PD-L1 | 2.28E−09 |
| hu5G11 | Human PD-L1 | 2.25E−10 |
| hu13C5 | Human PD-L1 | 1.74E−09 |
| hu5G11 | Cyno-PD-L1 | 2.75E−10 |
| hu13C5 | Cyno-PD-L1 | 2.43E−09 |

Example 3: ELISA Based Binding Analysis of Anti-PD-L1 Antibodies

Figure 2:
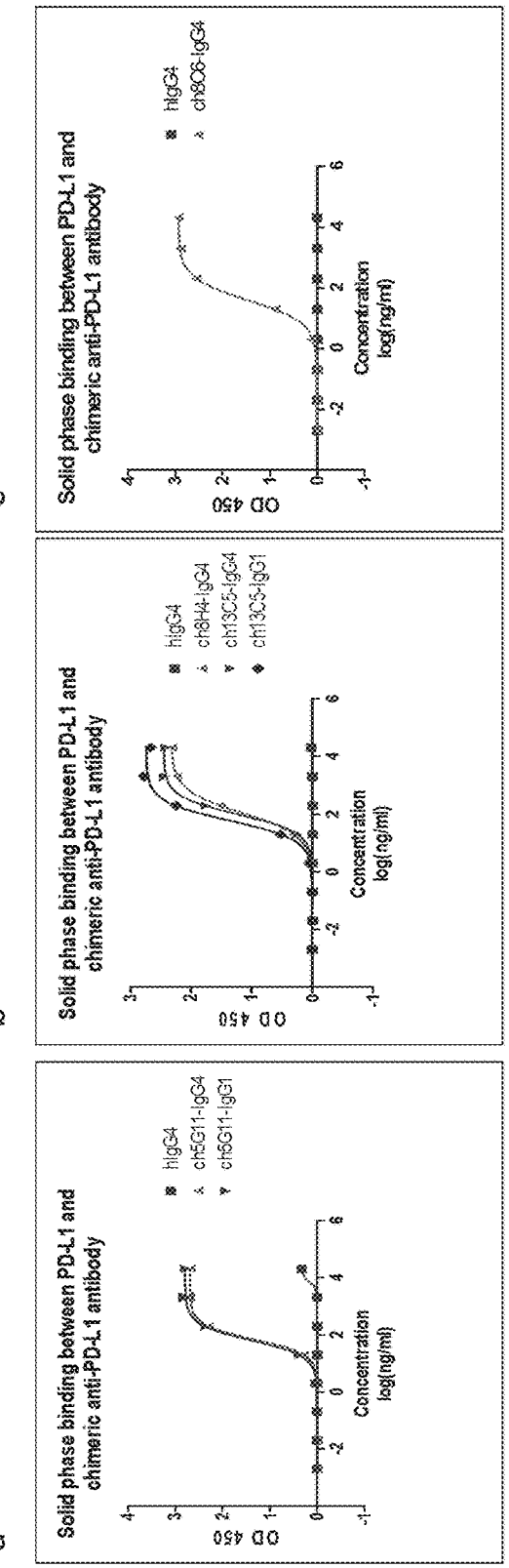
FIG. 2a-c is set of graphs showing the binding of chimeric anti-PD-L1 antibodies to PD-L1 over a range of concentrations as measured by ELISA. Binding of chimeric antibodies ch5G11-hIgG4 and ch5G11-hIgG1 is shown in FIG. 2a. Binding of chimeric antibodies ch13C5-hIgG4, ch13C5-hIgG1, and ch8H4-hIgG4 is shown in FIG. 2b. Binding of chimeric antibody ch8C6-hIgG4 is shown in FIG. 2c. In each of FIGS. 2a-2c, binding of hIgG4 is shown as a negative control.

ELISA binding analyses were conducted based on human PD-L1-mFc (for chimeric and humanized antibody detection) and PD-L1-hFc protein (for hybridoma antibody detection). 96-well plates (Costar, Cat No: 9018) were coated with 100 μL of 2 μg/ml PD-L1-mFc (Crownbio) in coating buffer PBS (Hyclone, Cat No: SH30256.01B) overnight at 4° C. The wells were aspirated and non-specific binding sites were blocked by adding 200 μL of blocking buffer (PBS with 1% (w/v) of bovine serum albumin (BSA, Roche, Cat No:738328)) and incubating for 1 hour at 37° C. After the plates were washed three times with wash buffer (PBS with 0.05% (v/v) Tween20 (Sigma, Cat No:P1379)), 100 μL/well of 1:10 serial dilutions of hybridoma (FIG. 1), chimeric (FIG. 2), or humanized (FIG. 3) anti-PD-L1 antibodies in blocking buffer (starting from 20 μg/mL) were added and incubated at room temperature for 1 hour. The plates were washed and incubated with 100 μL/well of Goat anti-Mouse IgG (H+L) (Thermo, Cat No: 31432) in blocking buffer for 60 min. After the plates were washed, 100 μL/well of substrate solution TMB (eBioscience, Cat No: 00-4201-56) were added and the plates were incubated for 2 min at room temperature. 100 μL/well of stop solution (2N $H_2SO_4$) was added to stop the reaction. The colorimetric signals were developed and read at 450 nm using an Auto Plate Spectra-Max Plus (Supplier: Moleculer Devices; Model: MNR0643; Software: SoftMax Pro v5.4). Data were analyzed using GraphPad Prism 5 and EC50 was calculated (FIGS. 1-3; Tables 5-7). These data demonstrated that anti-PD-L1 antibodies (hybridoma, chimeric, and humanized) bind PD-L1, as measured by ELISA.

TABLE 5

ELISA based binding EC50 of anti-PD-L1 hybridoma monoclonal antibody with PD-L1

| hybridoma Ab | m5G11 | m7B4 | m4D1 | m8H4 | m13C5 |
|---|---|---|---|---|---|
| EC50 ng/ml | 45.9 | 31.42 | 7.14 | 29.04 | 65.1 |
| hybridoma Ab | m8C6 | m5G9 | m4A8 | m8H3 | m15F1 |
| EC50 ng/ml | 18.2 | 31.2 | 57.6 | 48.7 | 48.7 |

TABLE 6

ELISA based binding EC50 of anti-PD-L1 chimeric antibody with PD-L1

| | Chimeric Ab | | | | | |
|---|---|---|---|---|---|---|
| | ch5G11 hIgG1 | ch5G11 hIgG4 | ch8C6 hIgG4 | ch8H4- hIgG4 | ch13C5 hIgG1 | ch13C5 hIgG4 |
| EC50 ng/ml | 82.1 | 90 | 76 | 133.6 | 72.1 | 118 |

TABLE 7

ELISA based binding EC50 of humanized anti-PD-L1 antibody with PD-L1

| Humanized Ab | hu13C5- hIgG1 | hu13C5- hIgG4 | hu5G11- hIgG1 | hu5G11- hIgG4 |
|---|---|---|---|---|
| EC50 (ng/ml) | 85.6 | 126.82 | 49.5 | 69.9 |

Figure 4:
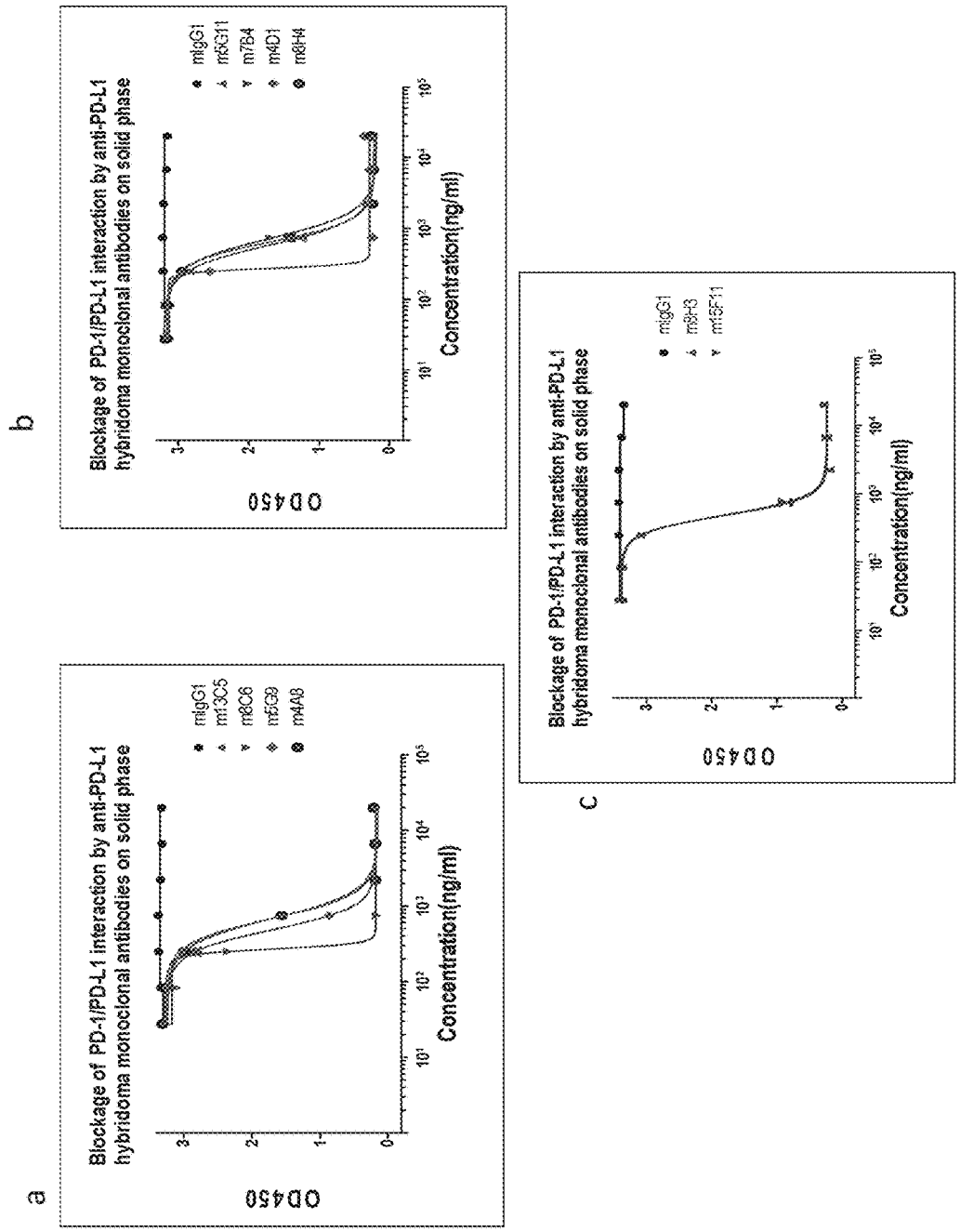
FIG. 4a-c is a set of graphs showing the blockage of the PD-1/PD-L1 interaction by hybridoma anti-PD-L1 antibodies over a range of antibody concentrations as measured by ELISA. Blockage of PD-1/PD-L1 binding by hybridoma antibodies 13C5-mIgG (m13C5), 8C6-mIgG (m8C6), 5G9-mIgG (m5G9), and 4A8-mIgG (m4A8) as compared to control mIgG1 is shown in FIG. 4a. Blockage of PD-1/PD-L1 binding by hybridoma antibodies 5G11-mIgG (m5G11), 7B4-mIgG (m7B4), 4D1-mIgG (m4D1), and 8H4-mIgG (m8H4) as compared to control mIgG1 is shown in FIG. 4b. Blockage of PD-1/PD-L1 binding by hybridoma antibodies 8H3-mIgG (m8H3) and 15F1-mIgG (m15F1) as compared to control mIgG1 is shown in FIG. 4c.
Figure 5:
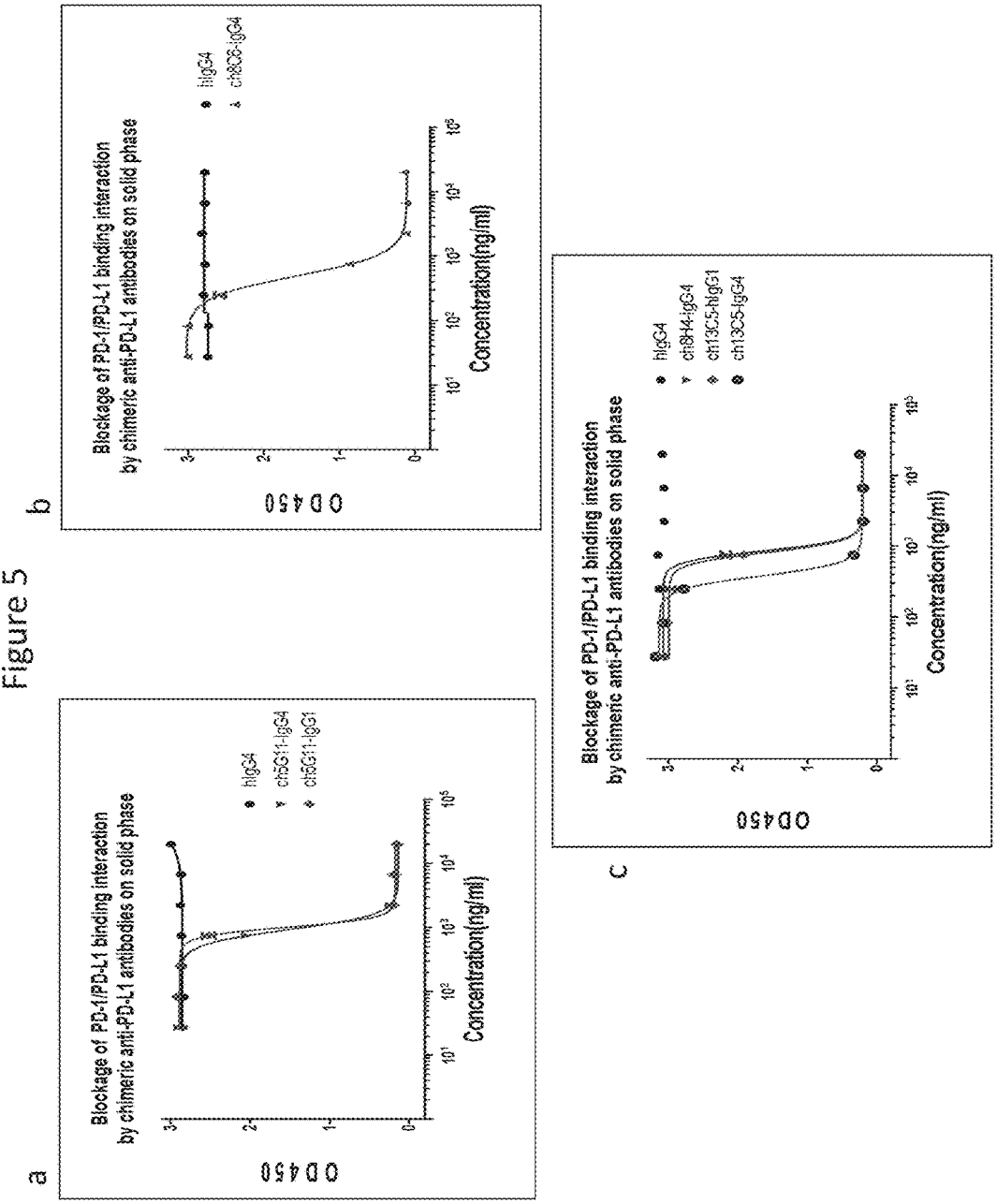
FIG. 5a-c is a set of graphs showing the blockage of the PD-1/PD-L1 interaction by chimeric anti-PD-L1 antibodies over a range of antibody concentrations as measured by ELISA. Blockage of PD-1/PD-L1 binding by chimeric antibodies ch5G11 hIgG4 and ch5G11 hIgG1 as compared to control hIgG4 is shown in FIG. 5a. Blockage of PD-1/PD-L1 binding by chimeric antibody ch8C6-hIgG4 as compared to control hIgG4 is shown in FIG. 5b. Blockage of PD-1/PD-L1 binding by chimeric antibodies ch8H4-hIgG4, ch13C5-hIgG1, and ch13C5-hIgG4 as compared to control hIgG4 is shown in FIG. 5c.
Figure 6:
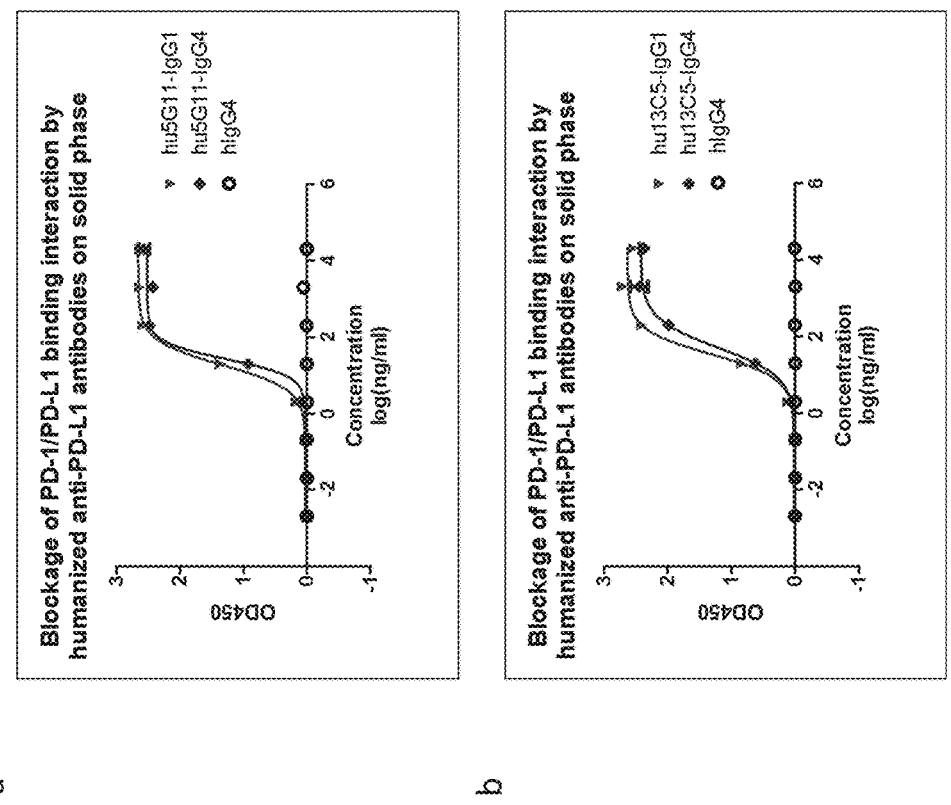
FIG. 6a-b is a set of graphs showing the blockage of the PD-1/PD-L1 interaction by humanized anti-PD-L1 antibodies over a range of antibody concentrations as measured by ELISA. Blockage of PD-1/PD-L1 binding by control hIgG4 and humanized antibodies 5G11-hIgG1 and 5G11-hIgG4 is shown in FIG. 6a. Blockage of PD-1/PD-L1 binding by control hIgG4 and humanized antibodies 13C5-hIgG1 and 13C5-hIgG4 is shown in FIG. 6b.

ELISA based ligand blockage analyses were conducted via blocking biotinylated human PD-L1-mFc's binding to human PD-1-hFc. PD-1-hFc antigen (Crownbio) was suspended in PBS buffer (2 ug/ml, 100 ul/well) and coated on the 96 well plate (Costar, Cat No: 9018) 4° C. overnight. The wells were aspirated and non-specific binding sites were blocked by adding 200 μL of blocking buffer (PBS with 1% (w/v) of bovine serum albumin (BSA, Roche, Cat No:738328)) and incubating for 1 hour at 37° C. After the plate was washed three times with wash buffer (PBS with 0.05% (v/v) Tween20 (Sigma, Cat No:P1379)), 100 μL/well of 1:3 serial dilutions of hybridoma (FIG. 4), chimeric (FIG. 5), or humanized (FIG. 6) anti-PD-L1 antibodies in blocking buffer (starting from 20 μg/mL) were added and incubated at 37° C. for 1 hour. 100 μl PDL-1-mFc-biotin (0.1 μg/ml) was then added to each well and incubated at 37° C. for 2 h. After the plate was washed 3 times, secondary antibody (Avidin HRP eBioscience cat No.: E07418-1632, 1:500, 100 μl/well) was added and incubated at 37° C. for 0.5 hour. After the plate was washed, 100 μL/well of substrate solution TMB (eBioscience, Cat No: 00-4201-56) was added and the plate was incubated for 3 min at room temperature. 100 μL/well of stop solution (2N $H_2SO_4$) was added to stop the reaction. The colorimetric signals were developed and read at 450 nm using an Auto Plate SpectraMax Plus (Supplier: Moleculer Devices; Model: MNR0643; Software: SoftMax Pro v5.4). Data were analyzed using GraphPad Prism 5 and IC50 was calculated (FIGS. 4-6; Tables 8-10). These data demonstrated that anti-PD-L1 antibodies (hybridoma, chimeric, and humanized) can block PD-1's binding with PD-L1 on the cell surface, as measured by ELISA.

TABLE 8

IC50 of anti-PD-L1 hybridoma monoclonal antibody inhibiting
PD-1 binding with PD-L1 on solid surface

| | Hybridoma Ab | | | | | | | | | |
|---|---|---|---|---|---|---|---|---|---|---|
| | m5G11 | m7B4 | m4D1 | m8H4 | m13C5 | m8C6 | m5G9 | m4A8 | m8H3 | m15F1 |
| IC50 (ng/ml) | 710.2 | 892.0 | 332.2 | 787.8 | 871.7 | 343.7 | 613.2 | 867.8 | 647.4 | 655.3 |

TABLE 9

IC50 of anti-PD-L1 chimeric antibody inhibiting
PD-1 binding with PD-L1 on solid surface

| | Chimeric Ab | | | | | |
|---|---|---|---|---|---|---|
| | ch5G11-hIgG1 | ch5G11-hIgG4 | ch8C6-hIgG4 | ch8H4-hIgG4 | ch13C5-hIgG1 | ch13C5-hIgG4 |
| IC50 (ng/mL) | 1006 | 926.1 | 476.6 | 848.1 | 805.2 | 375.3 |

TABLE 10

IC50 of humanized anti-PD-L1 antibody inhibiting PD-1 binding with
PD-L1 on solid surface

| Humanized Ab | hu5G11-hIgG1 | hu5G11-hIgG4 | hu13C5-hIgG1 | hu13C5-hIgG4 |
|---|---|---|---|---|
| IC50 (ng/ml) | 793.6 | 822.5 | 1202.6 | 1192.4 |

Example 4: Cell-Based Binding Analysis of Anti-PD-L1 Antibodies

Figure 8:
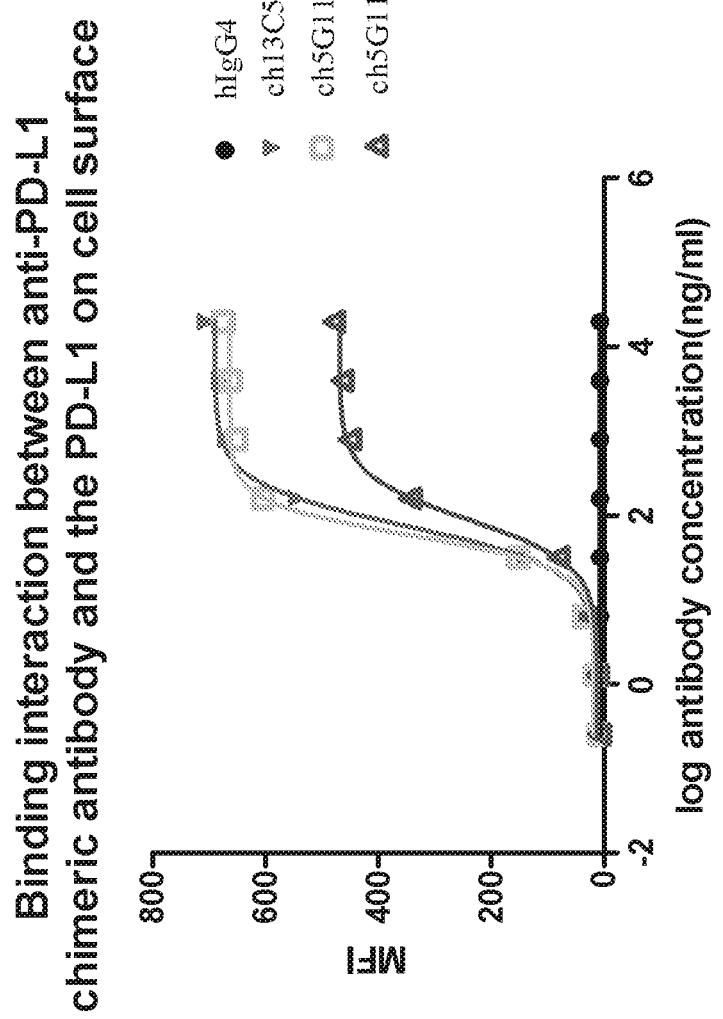
FIG. 8 shows the binding of the chimeric anti-PD-L1 antibodies to PD-L1 over a range of antibody concentrations as measured by FACS. Binding of control antibody hIgG4, and chimeric antibodies ch13C5-hIgG1, ch5G11-hIgG1, and ch5G11-hIgG4 are shown.
Figure 9:
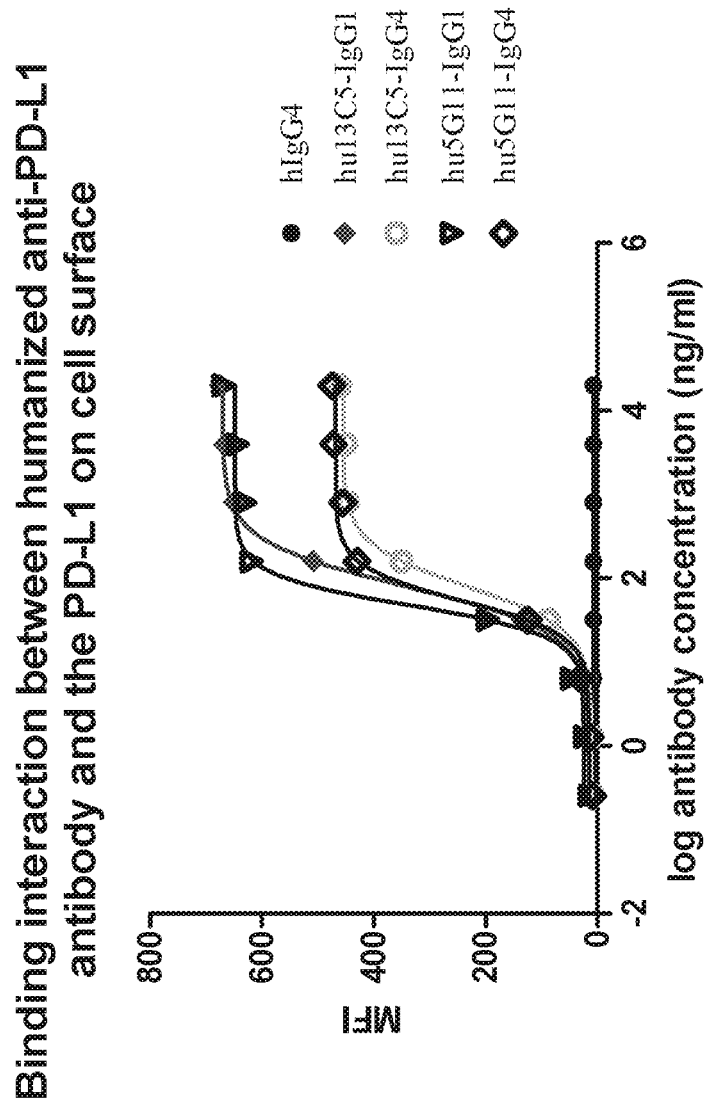
FIG. 9 shows the binding of humanized anti-PD-L1 antibodies to PD-L1 over a range of antibody concentrations as measured by FACS. Binding of control antibody hIgG4 and humanized antibodies hu13C5-hIgG1, hu13C5-hIgG4, hu5G11-hIgG1, and hu5G11-hIgG4 are shown.

Cell binding analyses of anti-PD-L1 antibodies were performed based on binding to a 293T cell line stably expressing PD-L1 (PD-L1-293T). $2\times10^5$ 293T-PD-L1 cells were added into each well of 96-well culture plates and incubated with the indicated antibody (20 μg/ml with the dilution of 1:5) at 4° C. for 1 h. After the cells were washed three times with FACS buffer, the secondary antibody (PE Goat anti-mouse: 1:200; PE mouse anti-human: 1:10) was added to the cells at 100 μl/well, and incubated at 4° C. for 40 min. Cells were washed three times with FACS buffer and analyzed by FACS Array. Binding of hybridoma antibodies is shown in FIGS. 7a and 7b. Binding of chimeric antibodies is shown in FIG. 8. Binding of humanized antibodies is shown in FIG. 9. The calculated EC50 for hybridoma, chimeric, and humanized antibodies are shown below in Tables 11, 12, and 13, respectively. These data demonstrated that anti-PD-L1 antibodies (hybridoma, chimeric, and humanized) bind PD-L1, as measured by FACS analysis.

TABLE 11

EC50 of anti-PD-L1 hybridoma monoclonal antibody with the PD-L1 on cell surface

| Hybridoma Ab | m4D1 | m4A8 | m5G11 | m8H4 | m8H3 |
|---|---|---|---|---|---|
| EC50 ng/ml | 36.07 | 67.83 | 35.94 | 43.49 | 50.81 |
| Hybridoma Ab | m8C6 | m9G9 | m7B4 | m13C5 | m15F1 |
| EC50 ng/ml | 40.97 | 33.7 | 47.41 | 45.29 | 47.8 |

TABLE 12

EC50 of anti-PD-L1 chimeric antibody with the PD-L1 on cell surface

| Chimeric Ab | ch13C5 hIgG1 | ch5G11 hIgG1 | ch5G11 hIgG4 |
|---|---|---|---|
| EC50 ng/ml | 75.75 | 58.26 | 89.68 |

TABLE 13

EC50 of humanized anti-PD-L1 antibody with the PD-L1 on cell surface

| Humanized Ab | hu5G11-hIgG1 | hu5G11-hIgG4 | hu13C5-hIgG1 | hu13C5-hIgG4 |
|---|---|---|---|---|
| EC50 ng/ml | 47.93 | 54.33 | 80.01 | 80.39 |

Figure 10:
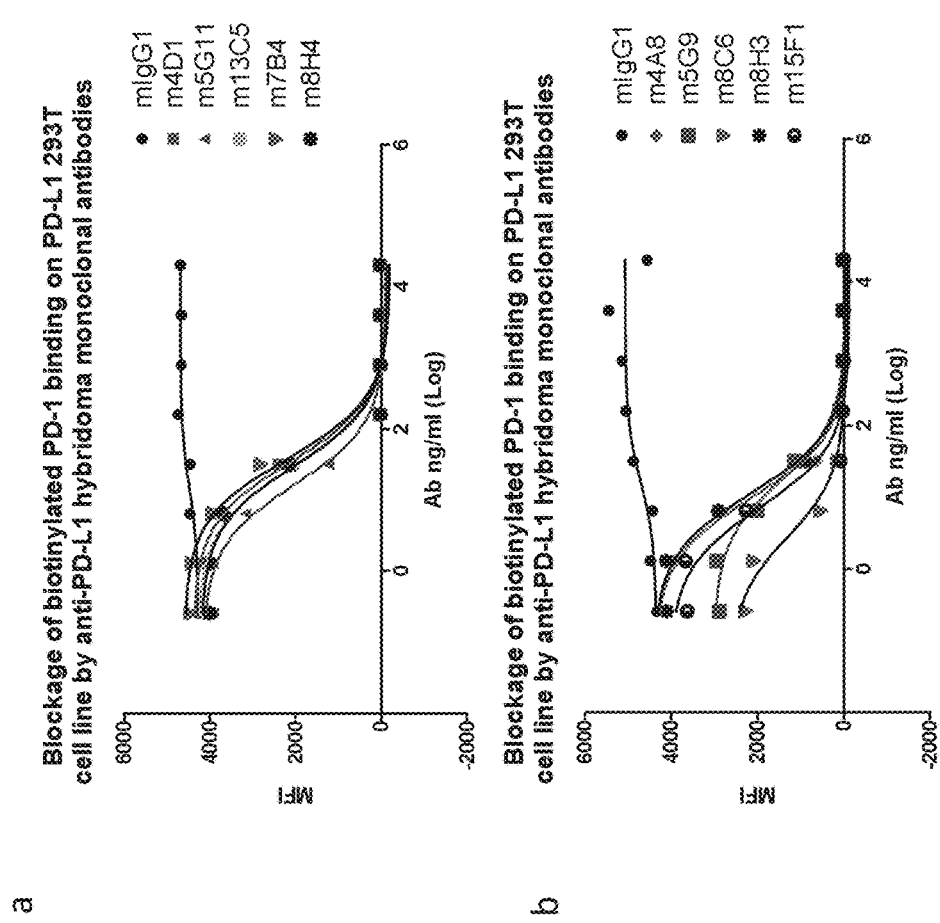
FIGS. 10a and 10b show the blockage of the PD-1/PD-L1 interaction by hybridoma anti-PD-L1 antibodies over a range of antibody concentrations as measured by FACS. Blockage of PD-1/PD-L1 binding by control antibody mIgG1 and hybridoma antibodies m4D1, m5G11, m13C5, m7B4, and m8H4 is shown in FIG. 10a. Blockage of PD-1/PD-L1 binding by control antibody mIgG1 and hybridoma antibodies m4A8, m5G9, m8C6, m8H3, and m15F1 is shown in FIG. 10b.
Figure 11:
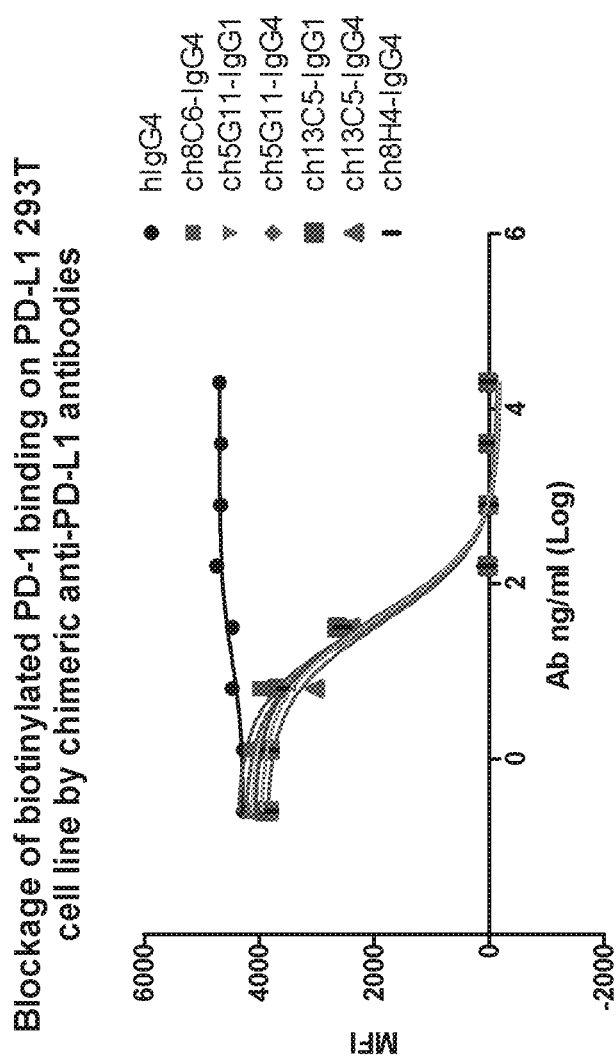
FIG. 11 shows the blockage of the PD-1/PD-L1 interaction over a range of concentrations of control antibody hIgG4 or chimeric anti-PD-L1 antibodies ch8C6-hIgG4, ch5G11-hIgG1, ch5G11-hIgG4, ch13C5-hIgG1, ch13C5-hIgG4, or ch8H4-hIgG4, as measured by FACS.
Figure 12:
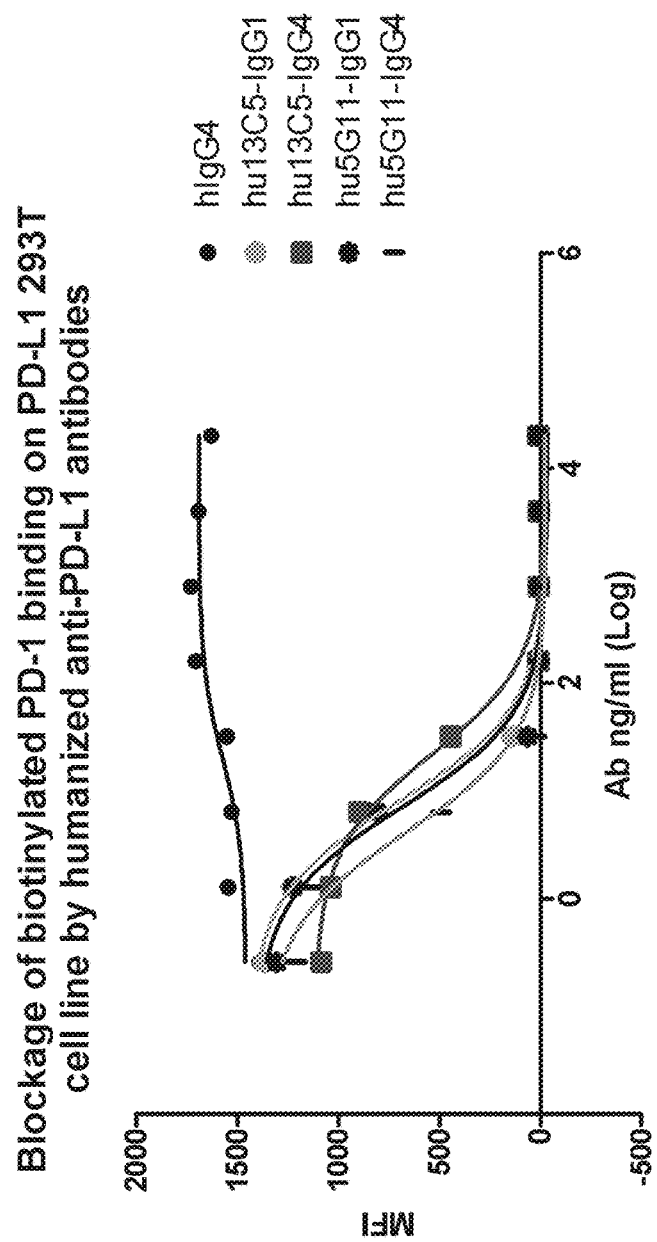
FIG. 12 shows the blockage of the PD-1/PD-L1 interaction over a range of concentrations of control antibody hIgG4 or humanized antibodies hu 13C5-hIgG1, hu13C5-hIgG4, hu5G11-hIgG1, or hu5G11-hIgG4, as measured by FACS.

The effect of anti-PD-L1 antibody on PD-1 binding to PD-L1 on the cell surface was also investigated. Briefly, PD-L1-293T cells were suspended in FACS buffer (PBS with 3% fetal calf serum). Various concentrations of the hybridoma (FIG. 10), chimeric (FIG. 11), or humanized (FIG. 12) anti-PD-L1 antibodies were added to the cell suspension and incubated at 4° C. for 60 minutes in 96 well plates. Biotin-labeled PD-L1 protein was then added to the wells and incubated at 4° C. for 60 minutes. The cells were washed 3 times with PBS and incubated with mouse anti-biotin PE (Biolegend, cat#409004). The cell-associated fluorescence was then detected by flow cytometry analysis using FACS array. The effects of anti-PD-L1 antibodies on PD-1 binding with PD-L1-293T were measured by the mean fluorescent intensity (MFI) of staining. Inhibition of PD-1 binding by anti-PD-L1 hybridoma antibodies is shown in FIGS. 10a and 10b. Inhibition of PD-1 binding by anti-PD-L1 chimeric antibodies is shown in FIG. 11. Inhibition of PD-1 binding by anti-PD-L1 humanized antibodies is shown in FIG. 12. The calculated IC50 for the hybridoma (Table 14), chimeric (Table 15), and humanized (Table 16) antibodies are shown in the tables below. These data demonstrated that anti-PD-L1 antibodies (hybridoma, chimeric, and humanized) can block PD-1's binding with PD-L1 on the cell surface, as measured by FACS analysis.

TABLE 14

IC50 of anti-PD-L1 hybridoma monoclonal antibody inhibiting
PD-1 binding with PD-L1 on cell surface

| | Hybridoma Ab | | | | | |
|---|---|---|---|---|---|---|
| | mIgG1 | m4D1 | m5G11 | m13C5 | m7B4 | m8H4 |
| IC50 ng/ml | NA | 27.3 | 16.3 | 28.9 | 38.1 | 30.6 |

| | Hybridoma Ab | | | | |
|---|---|---|---|---|---|
| | m4A8 | m5G9 | m8C6 | m8H3 | m15F1 |
| IC50 ng/ml | 29.1 | 49.1 | 8.2 | 33.6 | 21.1 |

TABLE 15

IC50 of anti-PD-L1 chimeric antibody inhibiting
PD-1 binding with PD-L1 on cell surface

| | Chimeric Ab | | | | | |
|---|---|---|---|---|---|---|
| | ch5G11-hIgG1 | ch5G11-hIgG4 | ch8C6-hIgG4 | ch8H4-hIgG4 | ch13C5-hIgG1 | ch13C5-hIgG4 |
| IC50 ng/ml | 40.36 | 33.18 | 34.91 | 42.02 | 42.71 | 35.78 |

TABLE 16

IC50 of humanized anti-PD-L1 antibody inhibiting PD-1 binding with
PD-L1 on cell surface

| Humanized Ab | hIgG4 | hu13C5-hIgG1 | hu13C5-hIgG4 | hu5G11-hIgG1 | hu5G11-hIgG4 |
|---|---|---|---|---|---|
| IC50 ng/ml | NA | 18.5 | 49.9 | 16.5 | 9.6 |

Example 5: Effect of Anti-PD-L1 Antibodies on T Cell Activation in a Mixed Lymphocyte Reaction A mixed lymphocyte reaction was employed to demonstrate the effect of murine (FIG. 13a, 13b), chimeric (FIG. 14a, 14b), or humanized (FIG. 15a, 15b) anti-PD-L1 antibodies in blocking the PD-L1/PD-1 pathway in lymphocyte effector cells. T cells in the assay were tested for IFN-γ and IL-2 secretion in the presence or absence of humanized anti-PD-L1 antibody.

Human CD4$^+$ T-cells were purified from human PBMC using a CD4$^+$ negative selection isolation kit (Mitenyi Biotech, cat #130-091-155). Immature dendritic cells (DC) were derived from monocytes isolated from human PBMC using the Mo-DC Generation Toolbox (Miltenyi, Cat#130-093-568). The cells were cultured with Mo-DC Differentiation Medium for 7 days, and were then induced to be mature DC with Mo-Dc Maturation medium for 2 days. To set up the MLR, for each reaction, $10^5$ purified T-cells and $10^4$ allogeneic mature DC cells were added in a total volume of 200 μl. The testing antibody was assayed at different concentrations as shown in FIGS. 13a, 13b, 14a, 14b, 15a, and 15b (i.e., 20 μg/mL, 2 μg/mL, 0.2 μg/mL, 0.02 μg/mL, and 0.002 μg/mL). Either no antibody or an isotype control antibody was used as a negative control. The cells were cultured for 5 days at 37° C. On day $6^{th}$, the levels of IFN-γ and IL-2 in the culture medium were measured using the IL-2 ELISA kit (eBioscience) and hIFN-γ ELISA kit (R&D, cat#DY285).

Figure 13A:
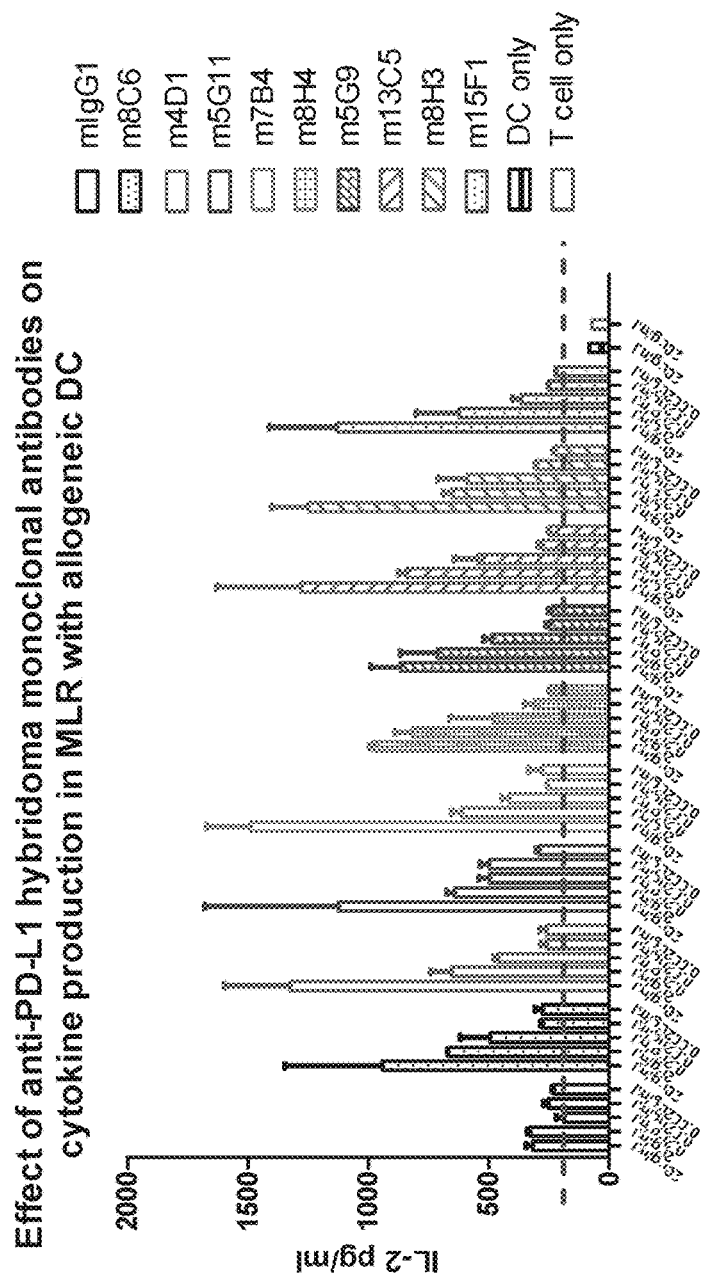
FIG. 13a is a graph showing IL-2 (pg/mL) production in an MLR in response to different concentrations of hybridoma anti-PD-L1 antibodies.
Figure 13B:
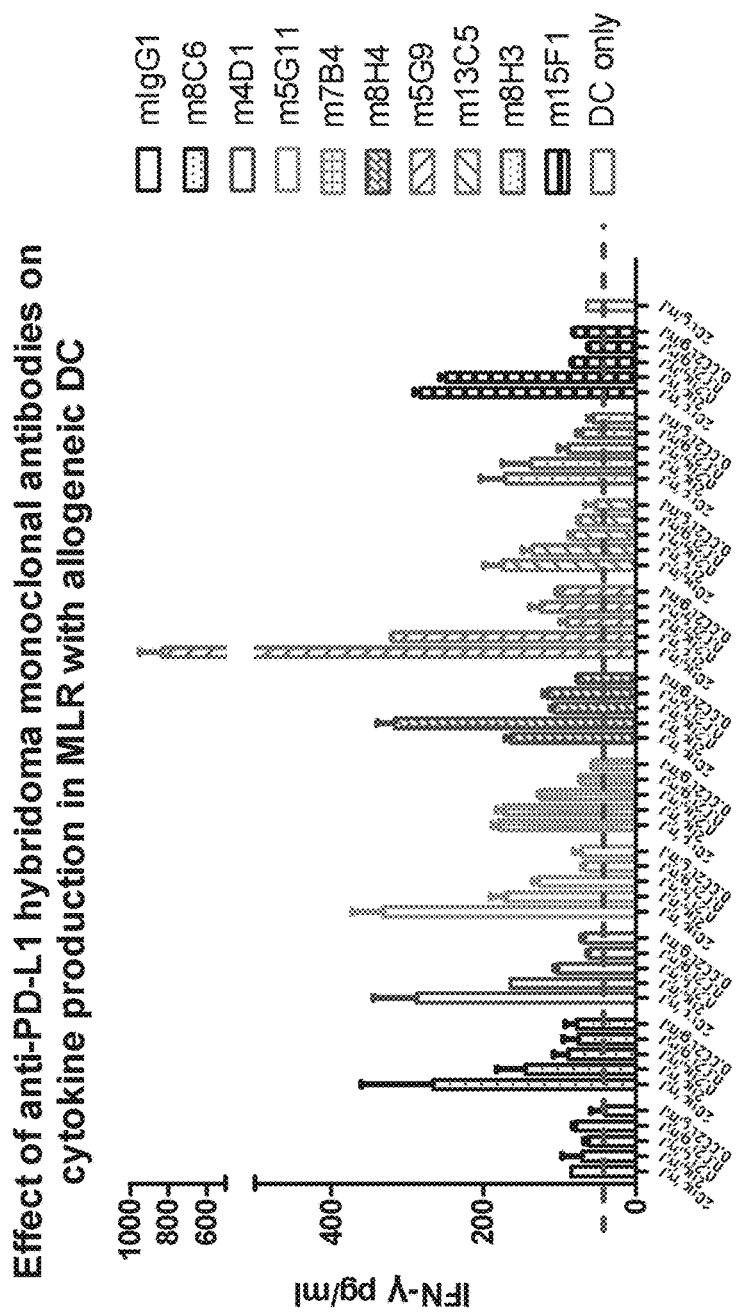
FIG. 13b is a graph showing IFNγ (pg/mL) production in an MLR in response to different concentrations of hybridoma anti-PD-L1 antibodies. For both FIGS. 13a and 13b, the antibodies tested were, from left to right, control mIgG1, m8C6, m4D1, m5G11, m7B4, m8H4, m5G9, m13C5, m8H3, and m15F1. T cell only and/or DC only wells were also included as negative controls. As shown on the x-axis for both FIGS. 13a and 13b, each antibody was tested at 20 µg/mL, 2 µg/mL, 0.2 µg/mL, 0.02 µg/mL, and 0.002 µg/mL.
Figure 14:
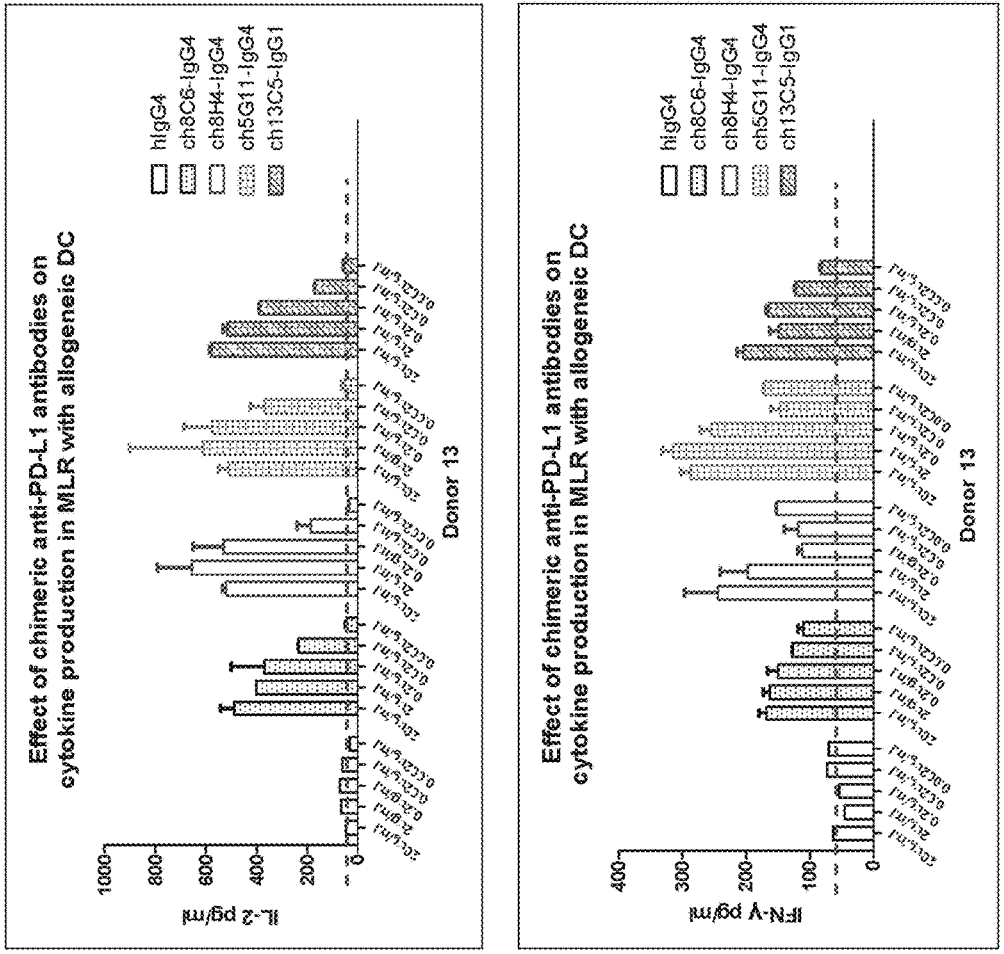
FIG. 14a is a graph showing IL-2 (pg/mL) production in an MLR in response to different concentrations of chimeric anti-PD-L1 antibodies.
FIG. 14b is a graph showing IFNγ (pg/mL) production in an MLR in response to different concentrations of chimeric anti-PD-L1 antibodies. For both FIGS. 14a and 14b, the antibodies tested were, from left to right, control hIgG4, chimeric 8C6-hIgG4, chimeric 8H4-hIgG4, chimeric 5G11-hIgG4, and chimeric 13C5-hIgG1. As shown on the x-axis for both FIGS. 14a and 14b, each antibody was tested at 20 µg/mL, 2 µg/mL, 0.2 µg/mL, 0.02 µg/mL, and 0.002 µg/mL.
Figure 15:
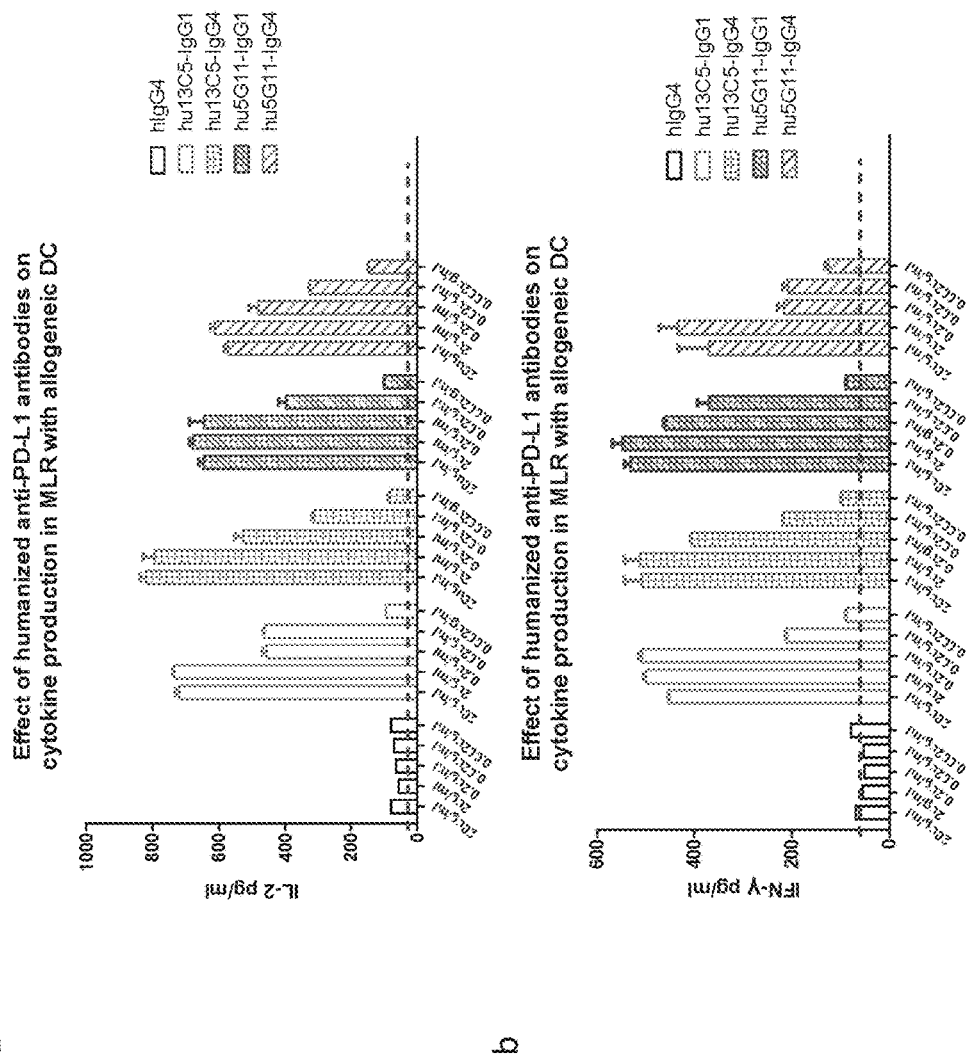
FIG. 15a is a graph showing IL-2 (pg/mL) production in an MLR in response to different concentrations of humanized anti-PD-L1 antibodies.
FIG. 15b is a graph showing IFNγ (pg/mL) production in an MLR in response to different concentrations of humanized anti-PD-L1 antibodies. For both FIGS. 15a and 15b, the antibodies tested were, from left to right, control hIgG4, hu13C5-hIgG1, hu13C5-hIgG4, hu5G11-hIgG1, and hu5G11-hIgG4. As shown on the x-axis for both FIGS. 15a and 15b, each antibody was tested at 20 µg/mL, 2 µg/mL, 0.2 µg/mL, 0.02 µg/mL, and 0.002 µg/mL.

The results are shown in FIGS. 13a, 14a, and 15a for IL-2 secretion, and FIGS. 13b, 14b, and 15b for IFN-γ secretion. The results of the study showed that hybridoma, chimeric, and humanized anti-PD-L1 antibodies promoted T-cell IFN-γ and IL-2 secretion in a concentration dependent manner. In contrast, cultures containing the isotype control antibody did not show increase in IFN-γ and IL-2 secretion.

Example 6: Effect of Anti-PD-L1 Antibody on the Function of T Regulatory Cells

Figure 16:
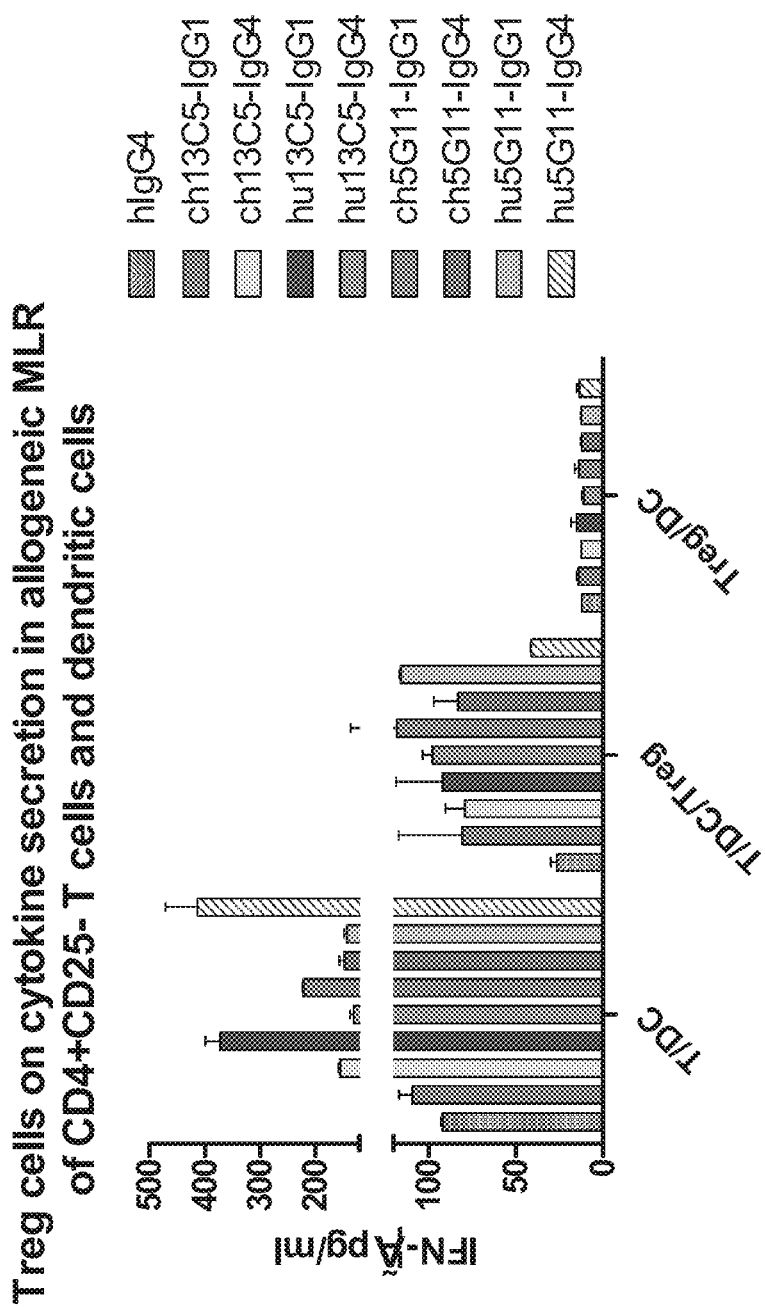
FIG. 16 shows the effects of chimeric (ch) or humanized (hu) anti-PD-L1 antibodies on Treg-mediated inhibition of IFNγ production (pg/mL), in an allogeneic MLR with CD4+ CD25+ Treg cells, CD4+CD25− T cells, and dendritic cells. The antibodies tested were, from left to right, control hIgG4, ch13C5-hIgG1, ch13C5-hIgG4, hu13C5-hIgG1, hu13C5-hIgG4, ch5G11-hIgG1, ch5G11-hIgG4, hu5G11-hIgG1, and hu5G11-hIgG4.

T regulatory cells (CD4+, CD25+) are lymphocytes that suppress the immune response. The effect of T regulatory cells on cytokine secretion of T effector cells in MLR was tested in the presence or absence of chimeric or humanized anti-PD-L1 antibodies. T regulatory cells (CD4+ CD25+) were purified from PBMC using a regulatory T cell isolation kit (Miltenyi Biotec, cat#130-091-301). Immature dendritic cells (DC) were derived from monocytes isolated from human PBMC using the Mo-DC Generation Toolbox (Miltenyi, cat#130-093-568). The cells were cultured with Mo-DC Differentiation Medium for 7 days, and were then induced to be mature DC with Mo-Dc Maturation medium for 2 days. T regulatory cells were added into a mixed lymphocyte reaction containing purified CD4$^+$ CD25$^-$ T cells and allogeneic dendritic cells in a 4:1 ratio of CD4$^+$ CD25$^-$ to T regulatory cells. For example: the reaction was added with $1 \times 10^5$ cells/well of CD4$^+$CD25$^-$ cells, $1 \times 10^4$ cells/well of mDC, and $0.25 \times 10^5$ cells/well of CD4$^+$CD25$^+$ cells. Antibody was added to each reaction at a concentration of 10 μg/ml. Either no antibody or an isotype control antibody was used as a negative control. The cells were cultured for 5 days at 37° C. On the $5^{th}$ day, 50 μl medium was taken to detect IL-2 and IFN-gamma concentration. After supplementing each well with 50 μl culture medium, the cells were cultured for another 2 days before analyzed for cell proliferation by CTG (Promega, G7573). The levels of IFN-γ and IL-2 in the culture medium were measured using a hIFN-γ ELISA kit (R&D, cat#DY285) and IL-2 ELISA kit (eBioscience). As shown in FIG. 16, chimeric and humanized anti-PD-L1 antibodies, ch-13C5-hIgG1, ch-13C5-hIgG4, hu-13C5-IgG1, hu-13C5-IgG4, ch-5G11-IgG1, ch-5G11-IgG4, hu-5G11-IgG1, and hu-5G11-IgG4, can reduce the inhibitory effect of Treg cells on the secretion of IFN-γ by CD4$^+$CD25$^-$ T effector cells, suggesting that anti-PD-L1 antibodies can modulate the immune suppression function of T regulatory cells.

Figure 17:
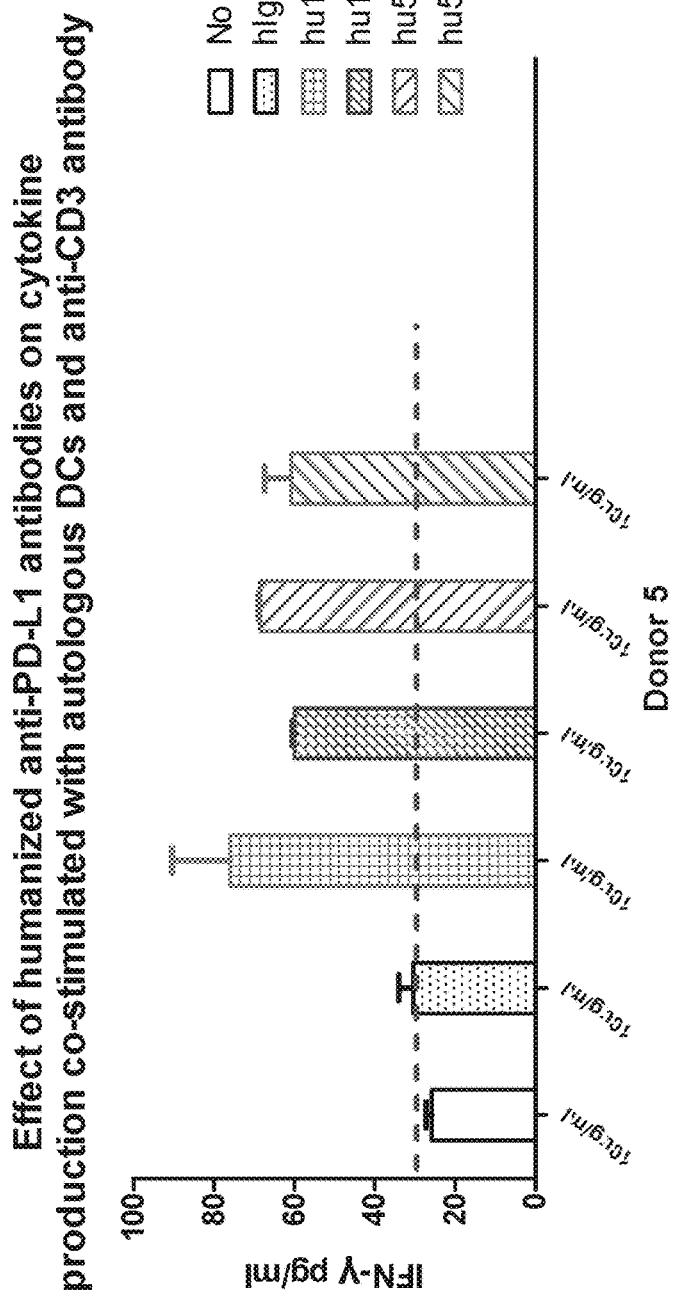
FIG. 17 shows IFN-γ production (pg/mL) from T cells in response to costimulation with autologous DCs and anti-CD3 antibody, in the presence of humanized anti-PD-L1 antibody (hu13C5-hIgG1, hu13C5-hIgG4, hu5G11-hIgG1, or hu5G11-hIgG4), isotype control (hIgG4) antibody, or no antibody.

Example 7: Effect of Humanized Anti-PD-L1 Antibody on Autologous T Cell Activation In this example, the effect of blocking PD-1/PD-L1 pathway by anti-PD-L1 antibody on T cell activation was examined. Purified human CD4+ T cells (Mitenyi Biotech, cat #130-091-155) were activated with 1 μg/ml soluble anti-CD3 antibody (R&D, cat#MAB100) in the presence of autologous monocyte-derived dendritic cells (DCs). After three days of activation in the presence or absence of titrated anti-PD-L1 antibody, culture medium was harvested and the concentration of IFNγ was measured with ELISA. The results are shown in FIG. 17 and suggest that PD-L1 blockage by humanized anti-PD-L1 antibodies enhanced IFN-γ secretion by T cells.

Figure 18:
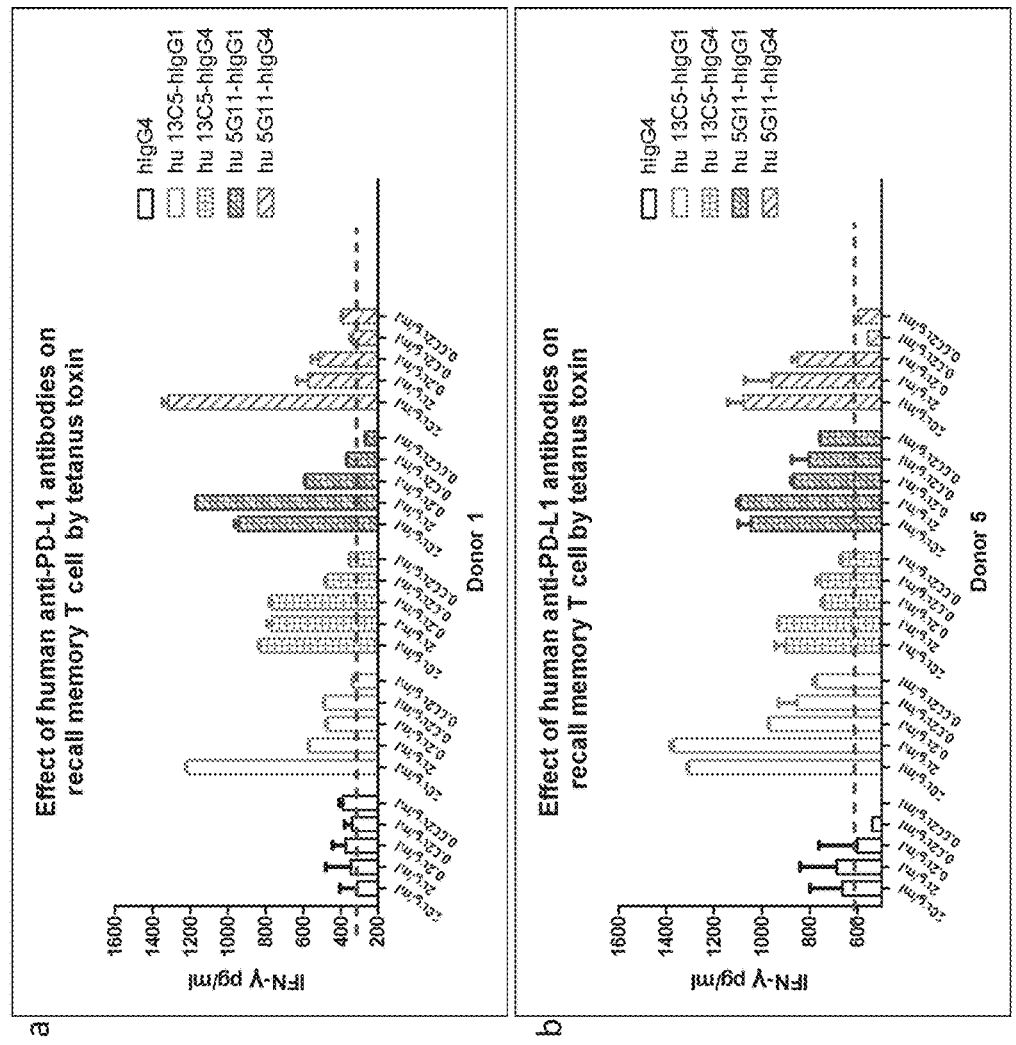
FIGS. 18a and 18b show the effect of humanized anti-PD-L1 antibodies on memory T cell responses recalled by tetanus toxin, as measured by IFN-γ production (pg/mL). Negative control hIgG4 or humanized antibody hu13C5-hIgG1, hu13C5-hIgG4, hu5G11-hIgG1, or hu5G11-hIgG4 were tested at the following concentrations: 20 µg/mL, 2 µg/mL, 0.2 µg/mL, 0.02 µg/mL, and 0.002 µg/mL.

Example 8: Human Recall T Cell Response to Tetanus Toxoid Challenge is Enhanced by Humanized Anti-PD-L1 Antibody To investigate whether the antigen-specific T cell receptor triggering was modulated by blocking PD-1/PD-L1 pathway with anti-PD-L1 antibodies, the human T-cell recall assay was employed using tetanus toxoid (TT) antigen to stimulate pre-existing memory T cells in the blood of healthy TT immunized donors. To this end, fresh PBMC from recently [<1 year] TT immunized donors were plated into 96-well round bottom plates (costar, cat #3799) at 4×10^5 cells/well using RPMI1640 (Invitrogen, cat #A10491-01) supplemented with 80 U/ml penicillin, 80 g/ml streptomycin and 30% autologous serum, added with humanized 5G11 or 13C5 at various concentrations, and stimulated with 0.1 ug/ml SEB and 1 μg/ml TT (Astarte Biologies). After co-culture for 7 days at 37° C., 5% $CO_2$, the supernatant was harvested and the concentration of IFN-γ was measured. FIGS. 18a and 18b provide the results of the assay using PBMC from two separate donors. The results of the study demonstrate that, compared to TT antigen alone, PD-L1 blockage with anti-PD-L1 antibody resulted in enhanced IFN-γ secretion by memory T cells.

In summary, the humanized 5G11 and 13C5 antibody retained the functional activity of their parental antibodies during the humanization process.

The invention claimed is:

1. An isolated antibody or fragment thereof that binds to PD-L1, wherein the antibody or fragment thereof comprises
    (i) a heavy chain CDR1, CDR2, and CDR3 sequence comprising SEQ ID NO: 81, 82, and 83, respectively, and a light chain CDR1, CDR2, and CDR3 sequence comprising SEQ ID NO: 84, 85, and 86, respectively;
    (ii) a heavy chain CDR1, CDR2, and CDR3 sequence comprising SEQ ID NO: 93, 94, and 95, respectively, and a light chain CDR1, CDR2, and CDR3 sequence comprising SEQ ID NO: 96, 97, and 98, respectively;
    (iii) a heavy chain CDR1, CDR2, and CDR3 sequence comprising SEQ ID NO: 99, 100, and 101, respectively, and a light chain CDR1, CDR2, and CDR3 sequence comprising SEQ ID NO: 102, 103, and 104, respectively;
    (iv) a heavy chain CDR1, CDR2, and CDR3 sequence comprising SEQ ID NO: 111, 112, and 113, respectively, and a light chain CDR1, CDR2, and CDR3 sequence comprising SEQ ID NO: 114, 115, and 116, respectively; or
    (v) a heavy chain CDR1, CDR2, and CDR3 sequence comprising SEQ ID NO: 123, 124, and 125, respectively, and a light chain CDR1, CDR2, and CDR3 sequence comprising SEQ ID NO: 126, 127, and 128, respectively.

2. The antibody or fragment of claim 1, wherein the antibody or fragment thereof comprises a heavy chain CDR1, CDR2, and CDR3 comprising an amino acid sequence according to SEQ ID NOs: 81, 82, and 83, respectively; and a light chain CDR1, CDR2, and CDR3 comprising an amino acid sequence according to SEQ ID NOs: 84, 85, and 86, respectively.

3. The antibody or fragment of claim 1, wherein the antibody or fragment thereof comprises a heavy chain CDR1, CDR2, and CDR3 comprising an amino acid sequence according to SEQ ID NOs: 93, 94, and 95, respectively; and a light chain CDR1, CDR2, and CDR3 comprising an amino acid sequence according to SEQ ID NOs: 96, 97, and 98, respectively.

4. The antibody or fragment of claim 1, wherein the antibody or fragment thereof comprises a heavy chain CDR1, CDR2, and CDR3 comprising an amino acid sequence according to SEQ ID NOs: 99, 100, and 101, respectively; and a light chain CDR1, CDR2, and CDR3 comprising an amino acid sequence according to SEQ ID NOs: 102, 103, and 104, respectively.

5. The antibody or fragment of claim 1, wherein the antibody or fragment thereof comprises a heavy chain CDR1, CDR2, and CDR3 comprising an amino acid sequence according to SEQ ID NOs: 111, 112, and 113, respectively; and a light chain CDR1, CDR2, and CDR3 comprising an amino acid sequence according to SEQ ID NOs: 114, 115, and 116, respectively.

6. The antibody or fragment of claim 1, wherein the antibody or fragment thereof comprises a heavy chain CDR1, CDR2, and CDR3 comprising an amino acid sequence according to SEQ ID NOs: 123, 124, and 125, respectively; and a light chain CDR1, CDR2, and CDR3 comprising an amino acid sequence according to SEQ ID NOs: 126, 127, and 128, respectively.

7. The isolated antibody or fragment thereof of claim 1, wherein the antibody or fragment thereof is chimeric or humanized.

8. The isolated antibody or fragment thereof of claim 1, wherein the antibody or fragment thereof comprises:
    (i) a heavy chain variable region comprising SEQ ID NO: 2 and a light chain variable region comprising SEQ ID NO: 4;
    (ii) a heavy chain variable region comprising SEQ ID NO: 10 and a light chain variable region comprising SEQ ID NO: 12;
    (iii) a heavy chain variable region comprising SEQ ID NO: 14 and a light chain variable region comprising SEQ ID NO: 16;
    (iv) a heavy chain variable region comprising SEQ ID NO: 22 and a light chain variable region comprising SEQ ID NO: 24;
    (v) a heavy chain variable region comprising SEQ ID NO: 30 and a light chain variable region comprising SEQ ID NO: 32; or
    (vi) a heavy chain variable region comprising SEQ ID NO: 46 and a light chain variable region comprising SEQ ID NO: 48.

9. The isolated antibody or fragment thereof of claim 1, wherein the antibody or fragment thereof comprises a heavy chain variable region according to SEQ ID NO: 42 and a light chain variable region according to SEQ ID NO: 44.

10. The isolated antibody or fragment thereof of claim 1, wherein the antibody or fragment thereof comprises a heavy chain variable region according to SEQ ID NO: 46 and a light chain variable region according to SEQ ID NO: 48.

11. The isolated antibody or fragment thereof of claim 1, wherein the antibody or fragment thereof comprises a heavy chain according to SEQ ID NO: 70 and a light chain according to SEQ ID NO: 74.

12. The isolated antibody or fragment thereof of claim 1, wherein the antibody or fragment thereof comprises a heavy chain according to SEQ ID NO: 72 and a light chain according to SEQ ID NO: 74.

13. The isolated antibody or fragment thereof of claim 1, wherein the antibody or fragment thereof comprises a heavy chain according to SEQ ID NO: 76 and a light chain according to SEQ ID NO: 80.

14. The isolated antibody or fragment thereof of claim 1, wherein the antibody or fragment thereof comprises a heavy chain according to SEQ ID NO: 78 and a light chain according to SEQ ID NO: 80.

15. The isolated antibody or fragment thereof of claim 1, wherein the antibody or fragment thereof is selected from the group consisting of a monoclonal antibody, an scFv, a Fab fragment, an Fab' fragment, and an F(ab)' fragment.

16. An antibody or fragment thereof according to claim 1, wherein the antibody or fragment thereof is linked or conjugated to a therapeutic agent.

17. The antibody or fragment thereof according to claim 16, wherein the therapeutic agent is a cytotoxic drug, a radioactive isotope, an immunomodulator, or an antibody.

18. The isolated antibody or fragment thereof according to claim 1, wherein the antibody or fragment thereof has an affinity for PD-L1 of about 10 nM to about 0.01 nM.

19. The isolated antibody or fragment thereof according to claim 18, wherein the antibody or fragment thereof as an affinity for PD-L1 of about 10 nM or less.

20. The isolated antibody or fragment thereof according to claim 18, wherein the antibody or fragment thereof as an affinity for PD-L1 of about 1.0 nM or less.

21. The isolated antibody or fragment thereof according to claim 1, wherein the antibody has a binding EC50 of about 5 ng/mL to about 1000 ng/mL.

22. The isolated antibody or fragment thereof of claim 1, wherein the antibody blocks binding of PD-L1 to PD-1.

23. An isolated antibody or fragment thereof of claim 1, wherein the antibody or fragment thereof blocks the binding of PD-L1 to PD-1 at an IC50 of about 5 ng/mL to about 1000 ng/mL.

24. The isolated antibody or fragment thereof of claim 1, wherein the antibody or fragment increases T cell activation as measured by inflammatory cytokine production.

25. The isolated antibody or fragment thereof according to claim 24, wherein the antibody or fragment thereof increases T cell production of IL-2 and IFNγ.

26. A composition comprising the antibody or fragment thereof according to claim 1 and a pharmaceutically acceptable carrier.

27. An isolated polynucleotide encoding the antibody or fragment thereof according to claim 1.

28. An expression vector comprising the isolated polynucleotide according to claim 27.

29. A host cell comprising the expression vector according to claim 28.

30. A method for increasing T cell activation, the method comprising contacting T cells with an antibody or fragment thereof according to claim 1.

\* \* \* \* \*

SEQUENCE LISTING

<160> NUMBER OF SEQ ID NOS: 156

<210> SEQ ID NO 1
<211> LENGTH: 348
<212> TYPE: DNA
<213> ORGANISM: Mus sp.

<400> SEQUENCE: 1

```
gaggtgaagc tggtggagtc tgggggaggc ttagtgaagc ctggagggtc cctgaaactc      60
tcctgtgcag cctctggatt cattttcaga agctatggca tgtcttgggt tcgccagact     120
ccagagaaga ggctggagtg ggtcgcatcc attagtagtg gtggtagcac ctactatcca     180
gacagtgtga agggccgatt caccatctcc agagataatg ccaggaacat cttgtacctg     240
caaatgagca gtctgaggtc tgaggacacg gccatgtatg actgtgcaag aggctatgat     300
tcggggtttg cttattgggg ccaagggact ctggtcactg tctctgaa                  348
```

<210> SEQ ID NO 2
<211> LENGTH: 116
<212> TYPE: PRT
<213> ORGANISM: Mus sp.

<400> SEQUENCE: 2

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ile Phe Arg Ser Tyr
            20                  25                  30

Gly Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Glu
        115
```

<210> SEQ ID NO 3
<211> LENGTH: 336
<212> TYPE: DNA
<213> ORGANISM: Mus sp.

<400> SEQUENCE: 3

```
gacattgtgc tgacacagtc tcctgcttcc ttagctgttt ctctggggca gagggccacc      60
atctcatgca gggccagcca aagtgtcagt acttctagct ctagttttat gcactggtac     120
```
caacagaaac caggacagcc acccaaactc ctcatcaagt atgcatccaa cctagaatct    180 gggggtccctg ccaggttcag tggcagtggg tctgggacag acttcaccct caacatccat    240
cctgtggagg aggaggatac tgcaacatat tactgtcagc acagttggga gattccgtac    300
acgttcggag gggggaccaa gctggaaata aaacgg                              336

```
<210> SEQ ID NO 4
<211> LENGTH: 112
<212> TYPE: PRT
<213> ORGANISM: Mus sp.

<400> SEQUENCE: 4
```

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Ser Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

```
<210> SEQ ID NO 5
<211> LENGTH: 348
<212> TYPE: DNA
<213> ORGANISM: Mus sp.

<400> SEQUENCE: 5
```
gaagtaaagt tggtggagtc tgggggaggc ttagtgaagc ctggagggtc cctgaaactc    60
tcctgtgcag cctctggatt cactttcaga agctatggca tgtcttgggt tcgccagact    120
ccagagaaga ggctggagtg ggtcgcatcc attagtagtg gtggtaccac ctactatcca    180
gacagtgtga aggccgatt catcatctcc agagataatg ccaggaacat cctgtacctg    240
caaatgagca gtctgaggtc tgaggacacg gccatgtatt attgtgcaaa aggctatgat    300
tcggggtttg cttactgggg ccaagggact ctggtcattg tctctgca                 348

```
<210> SEQ ID NO 6
<211> LENGTH: 116
<212> TYPE: PRT
<213> ORGANISM: Mus sp.

<400> SEQUENCE: 6
```

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Ser Tyr
            20                  25                  30

Gly Met Ser Trp Val Arg Gln Thr Pro Glu Lys Arg Leu Glu Trp Val
        35                  40                  45

Ala Ser Ile Ser Ser Gly Gly Thr Thr Tyr Tyr Pro Asp Ser Val Lys
    50                  55                  60

Gly Arg Phe Ile Ile Ser Arg Asp Asn Ala Arg Asn Ile Leu Tyr Leu

```
                65                  70                  75                  80
Gln Met Ser Ser Leu Arg Ser Glu Asp Thr Ala Met Tyr Tyr Cys Ala
                    85                  90                  95

Lys Gly Tyr Asp Ser Gly Phe Ala Tyr Trp Gly Gln Gly Thr Leu Val
            100                 105                 110

Ile Val Ser Ala
        115
```

<210> SEQ ID NO 7
<211> LENGTH: 333
<212> TYPE: DNA
<213> ORGANISM: Mus sp.

<400> SEQUENCE: 7

```
gacattgtgc tgacacagtc tcctccttcc ttagctgtat ctctggggca gagggccacc    60
atctcatgca gggccagcca agtgtcagt acatctagtt ctagttatat gcactggtac   120
caacagaaac caggacagcc tcccaaactc ctcatcaagt atgcatccaa cctagaatct   180
ggggtccctg ccaggttcag tggcagtggg tctgggacag acttcaccct caacatccat   240
cctgtggagg aggaggatac tgcaacatat tactgtcagc acagttggga gattccgtac   300
acgttcggag ggggaccaa gctggaaata aaa                                 333
```

<210> SEQ ID NO 8
<211> LENGTH: 111
<212> TYPE: PRT
<213> ORGANISM: Mus sp.

<400> SEQUENCE: 8

```
Asp Ile Val Leu Thr Gln Ser Pro Pro Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Ser Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110
```

<210> SEQ ID NO 9
<211> LENGTH: 348
<212> TYPE: DNA
<213> ORGANISM: Mus sp.

<400> SEQUENCE: 9

```
caggtgcagc tgaagcagtc aggacctggc ctagtgcagc cctcacagag cctgtccatc    60
acctgcacag tctctggttt ctcattaact acctatggtg tacactgggt tcgccagtct   120
ccaggaaagg gtctggaatg gctgggagtg atatggcgtg gtgtaaccac agactataat   180
gcagctttca tgtccagact gaccatcacc aaggacaatt ccaagagcca gttttctttt   240
aaaatgaaca gtctgcaagc taatgacaca gccatatatt actgtgccag actgggtttc   300
tatgctatgg actactgggg tcaaggaacc tcagtcaccg tctcctca                348
```

<210> SEQ ID NO 10
<211> LENGTH: 116
<212> TYPE: PRT
<213> ORGANISM: Mus sp.

<400> SEQUENCE: 10

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Arg Gly Val Thr Thr Asp Tyr Asn Ala Ala Phe Met
    50                  55                  60

Ser Arg Leu Thr Ile Thr Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Leu Gly Phe Tyr Ala Met Asp Tyr Trp Gly Gln Gly Thr Ser Val
            100                 105                 110

Thr Val Ser Ser
        115

<210> SEQ ID NO 11
<211> LENGTH: 324
<212> TYPE: DNA
<213> ORGANISM: Mus sp.

<400> SEQUENCE: 11
agtattgtga tgacccagac tcccaaattc ctgcttgtat cagcaggaga cagggttacc      60
ataacctgca aggccagtca gagtgtgagt aatgatgtag cttggtacca gcagaagcca     120
gggcagtctc ctaaactgct gatatattat gcagccaatc gctacactgg agtccctgat     180
cgcttcactg gcagtggata tgggacggat ttcactttca ccatcagcat tgtgcaggct     240
gaagacctgg cagtttattt ctgtcagcag gattataccc tccgtacac gttcggaggg     300 gggaccaagc tggaaataaa acgg                                            324

<210> SEQ ID NO 12
<211> LENGTH: 107
<212> TYPE: PRT
<213> ORGANISM: Mus sp.

<400> SEQUENCE: 12

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ala Asn Arg Tyr Thr Gly Val Pro Asp Arg Phe Thr Gly
    50                  55                  60

Ser Gly Tyr Gly Thr Asp Phe Thr Phe Thr Ile Ser Ile Val Gln Ala
65                  70                  75                  80

Glu Asp Leu Ala Val Tyr Phe Cys Gln Gln Asp Tyr Thr Ser Pro Tyr
                85                  90                  95

```
Thr Phe Gly Gly Gly Thr Lys Leu Glu Ile Lys
            100                 105
```

<210> SEQ ID NO 13
<211> LENGTH: 348
<212> TYPE: DNA
<213> ORGANISM: Mus sp.

<400> SEQUENCE: 13

| | | | | | |
|---|---|---|---|---|---|
| caggtgcagc | tgaagcagtc | aggacctggc | ctagtgcagc | cctcacagag | cctgtccatc | 60 |
| acctgcacag | tctctggttt | ctcattaact | agctatggtg | tacactgggt | tcgccagtct | 120 |
| ccaggaaagg | gtctggagtg | gctgggagtg | atatggagtg | gtggagtcac | agactataat | 180 |
| gcagctttca | tatccagact | gagcatcagc | aaggacaatt | ccaagagcca | gttttctttt | 240 |
| aaaatgaaca | gtctgcaagc | taatgacaca | gccatatatt | actgtgccag | actcggtttc | 300 |
| tatgctatgg | actactgggg | tcaaggaacc | tcagtcaccg | tctcctca | | 348 |

<210> SEQ ID NO 14
<211> LENGTH: 116
<212> TYPE: PRT
<213> ORGANISM: Mus sp.

<400> SEQUENCE: 14

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Val Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Leu Gly Phe Tyr Ala Met Asp Tyr Trp Gly Gln Gly Thr Ser Val
            100                 105                 110

Thr Val Ser Ser
        115
```

<210> SEQ ID NO 15
<211> LENGTH: 321
<212> TYPE: DNA
<213> ORGANISM: Mus sp.

<400> SEQUENCE: 15

| | | | | | |
|---|---|---|---|---|---|
| agtattgtga | tgacccagac | tcccaaattc | ctacttgtat | cagcaggaga | cagggttacc | 60 |
| ataacctgca | aggccagtca | gagtgtgagt | aatgatgtag | gttggtacca | acagaagcca | 120 |
| gggcagtctc | ctaaactact | gatatactat | gcatccaatc | gctactctgg | agtccctgat | 180 |
| cgcttcactg | gcagtggata | tgggacggat | ttcactttca | ccatcagcac | tgtgcaggct | 240 |
| gaagacctgg | cagtttattt | ctgtcaacaa | gattatacct | ctccgtacac | gttcggaggg | 300 |
| gggaccaagc | tggaaataaa | a | | | | 321 |

<210> SEQ ID NO 16
<211> LENGTH: 107
<212> TYPE: PRT

```
<213> ORGANISM: Mus sp.

<400> SEQUENCE: 16

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
                20                  25                  30

Val Gly Trp Tyr Gln Gln Lys Pro Gly Gln Ser Pro Lys Leu Leu Ile
            35                  40                  45

Tyr Tyr Ala Ser Asn Arg Tyr Ser Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Thr Ser Pro Tyr
                85                  90                  95

Thr Phe Gly Gly Gly Thr Lys Leu Glu Ile Lys
                100                 105

<210> SEQ ID NO 17
<211> LENGTH: 357
<212> TYPE: DNA
<213> ORGANISM: Mus sp.

<400> SEQUENCE: 17
gaggtgaagc tgttcgagtc tggaggtggc ctggtgcagc ctggaggatc cctgaaactc      60
tcctgtgtag cctcaggatt cgattttagt acatactgga tgcattgggt ccggcaggct     120
ccagggcaag ggctagaatg gattggacaa attaatccag atagcactac gataaactat     180
gcgccatctc taaggatag attcatcatc tccagagaca acgccaaaaa tacgctgttc       240
ctgcaaatga gcaaagtgag atctgaggac actgcccttt attactgtgc aaaacccggg     300
gactatggtt acgactttga ctgctggggc caaggcacca ctctcacagt ctcctca         357

<210> SEQ ID NO 18
<211> LENGTH: 119
<212> TYPE: PRT
<213> ORGANISM: Mus sp.

<400> SEQUENCE: 18

Glu Val Lys Leu Phe Glu Ser Gly Gly Gly Leu Val Gln Pro Gly Gly
1               5                   10                  15

Ser Leu Lys Leu Ser Cys Val Ala Ser Gly Phe Asp Phe Ser Thr Tyr
                20                  25                  30

Trp Met His Trp Val Arg Gln Ala Pro Gly Gln Gly Leu Glu Trp Ile
            35                  40                  45

Gly Gln Ile Asn Pro Asp Ser Thr Thr Ile Asn Tyr Ala Pro Ser Leu
        50                  55                  60

Lys Asp Arg Phe Ile Ile Ser Arg Asp Asn Ala Lys Asn Thr Leu Phe
65                  70                  75                  80

Leu Gln Met Ser Lys Val Arg Ser Glu Asp Thr Ala Leu Tyr Tyr Cys
                85                  90                  95

Ala Lys Pro Gly Asp Tyr Gly Tyr Asp Phe Asp Cys Trp Gly Gln Gly
                100                 105                 110

Thr Thr Leu Thr Val Ser Ser
        115

<210> SEQ ID NO 19
```

<211> LENGTH: 339
<212> TYPE: DNA
<213> ORGANISM: Mus sp.

<400> SEQUENCE: 19

```
gatgttttga tgacccaaac tccactctac ctgcctgtca gtcttggaga tcaggcctcc    60
atctcttgca gatctagtca gatcattgta catagtaatg caaacaccta tttagaatgg   120
ttcctgcaga aaccaggcca gtctccaaag ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttccg   300
tacacgttcg gagggggac caagctggaa ataaaacgg                           339
```

<210> SEQ ID NO 20
<211> LENGTH: 112
<212> TYPE: PRT
<213> ORGANISM: Mus sp.

<400> SEQUENCE: 20

```
Asp Val Leu Met Thr Gln Thr Pro Leu Tyr Leu Pro Val Ser Leu Gly
1               5                   10                  15

Asp Gln Ala Ser Ile Ser Cys Arg Ser Ser Gln Ile Ile Val His Ser
            20                  25                  30

Asn Ala Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110
```

<210> SEQ ID NO 21
<211> LENGTH: 357
<212> TYPE: DNA
<213> ORGANISM: Mus sp.

<400> SEQUENCE: 21

```
gaggtgcagc ttcaggagtc aggacctagc ctcgtgaaac cttctcagac tctgtccctc    60
acctgttctg tcactggcga ctccatcacc agtggttact ggaactggat ccggaaattc   120
ccagggaata acttgagta catggggtac ataagctaca gtggtagcac ttactacaat   180
ccatctctca aaagtcgaat ctccatcact cgagacacat ccaagaacca gtactacctg   240
cagttgaatt ctgtgactac tgaggacaca gccacatatt actgtgcaag aagtctacta   300
tggttctcta cggggtttgc ttactggggc caaggactc tggtcactgt ctctgca       357
```

<210> SEQ ID NO 22
<211> LENGTH: 119
<212> TYPE: PRT
<213> ORGANISM: Mus sp.

<400> SEQUENCE: 22

```
Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
```

```
            20                  25                  30
Tyr Trp Asn Trp Ile Arg Lys Phe Pro Gly Asn Lys Leu Glu Tyr Met
        35                  40                  45

Gly Tyr Ile Ser Tyr Ser Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Ser Leu Leu Trp Phe Ser Thr Gly Phe Ala Tyr Trp Gly Gln Gly
            100                 105                 110

Thr Leu Val Thr Val Ser Ala
        115
```

<210> SEQ ID NO 23
<211> LENGTH: 324
<212> TYPE: DNA
<213> ORGANISM: Mus sp.

<400> SEQUENCE: 23

```
caaattgttc tcacccagtc tccagcaatc atgtctgcat ctcctgggga gaaggtcacc    60
ttgacctgca gtgccagctc aagtgtaagt tccagctact tgtactggaa ccagcagaag   120
ccaggatcct cccccaaagt ctggatttat aacacatcca acctggcttc tggagtccct   180
gctcgcttca gtggcagtgg gtctgggacc tcttactctc tcacaatcag cagcatggag   240
gctgaagatg ctgcctctta tttctgccat cagtggagaa gttacccacc cacgctcggt   300
gctgggacca agctggagct gaaa                                          324
```

<210> SEQ ID NO 24
<211> LENGTH: 108
<212> TYPE: PRT
<213> ORGANISM: Mus sp.

<400> SEQUENCE: 24

```
Gln Ile Val Leu Thr Gln Ser Pro Ala Ile Met Ser Ala Ser Pro Gly
1               5                   10                  15

Glu Lys Val Thr Leu Thr Cys Ser Ala Ser Ser Ser Val Ser Ser
            20                  25                  30

Tyr Leu Tyr Trp Asn Gln Gln Lys Pro Gly Ser Ser Pro Lys Val Trp
        35                  40                  45

Ile Tyr Asn Thr Ser Asn Leu Ala Ser Gly Val Pro Ala Arg Phe Ser
    50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Arg Ser Tyr Pro
                85                  90                  95

Pro Thr Leu Gly Ala Gly Thr Lys Leu Glu Leu Lys
            100                 105
```

<210> SEQ ID NO 25
<211> LENGTH: 348
<212> TYPE: DNA
<213> ORGANISM: Mus sp.

<400> SEQUENCE: 25

```
caggtgcagc tgaagcagtc aggacctggc ctagtgcagc cctcacagag cctgtccatc    60
```

| | |
|---|---|
| acctgcacag tctctggttt ctcattaact agctatggtg tacactgggt tcgccagtct | 120 |
| ccaggaaagg gtctggagtg gctgggagtg atatggagtg gtggaatcac agactataat | 180 |
| gcagctttca atccagact gagcatcagc aaggacaatt ccaagagcca agttttcttt | 240 |
| aagatgaaca gtctgcaagc taatgacaca gccatatatt tctgtgccag actgggtttt | 300 |
| tatgctatgg actactgggg tcaaggaacc tcagtcaccg tctcctca | 348 |

<210> SEQ ID NO 26
<211> LENGTH: 116
<212> TYPE: PRT
<213> ORGANISM: Mus sp.

<400> SEQUENCE: 26

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ile Thr Asp Tyr Asn Ala Ala Phe Lys
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Phe Cys Ala
                85                  90                  95

Arg Leu Gly Phe Tyr Ala Met Asp Tyr Trp Gly Gln Gly Thr Ser Val
            100                 105                 110

Thr Val Ser Ser
        115
```

<210> SEQ ID NO 27
<211> LENGTH: 318
<212> TYPE: DNA
<213> ORGANISM: Mus sp.

<400> SEQUENCE: 27

| | |
|---|---|
| caaattgttc tcacccagtc tccagcaatc atgtctgcat ctccagggga gaaggtcacc | 60 |
| atgacctgca gtgccaactc aagtgtaagt tacatgcact ggtaccagca gaagtcaggc | 120 |
| acttccccca aaagatggat ttatgacaca tccaaactgg cttctggagt ccctgctcgc | 180 |
| ttcagtggca gtgggtctgg gacctcttac tctctcacaa tcagcagcat ggggctgaa | 240 |
| gatgctgcca cttattactg ccagcagtgg agtagtaacc catggacgtt cggtggaggc | 300 |
| accaagctgg aaatcaaa | 318 |

<210> SEQ ID NO 28
<211> LENGTH: 106
<212> TYPE: PRT
<213> ORGANISM: Mus sp.

<400> SEQUENCE: 28

```
Gln Ile Val Leu Thr Gln Ser Pro Ala Ile Met Ser Ala Ser Pro Gly
1               5                   10                  15

Glu Lys Val Thr Met Thr Cys Ser Ala Asn Ser Ser Val Ser Tyr Met
            20                  25                  30

His Trp Tyr Gln Gln Lys Ser Gly Thr Ser Pro Lys Arg Trp Ile Tyr
        35                  40                  45
```

```
Asp Thr Ser Lys Leu Ala Ser Gly Val Pro Ala Arg Phe Ser Gly Ser
        50                  55                  60
Gly Ser Gly Thr Ser Tyr Ser Leu Thr Ile Ser Ser Met Gly Ala Glu
 65                  70                  75                  80
Asp Ala Ala Thr Tyr Tyr Cys Gln Gln Trp Ser Ser Asn Pro Trp Thr
                85                  90                  95
Phe Gly Gly Gly Thr Lys Leu Glu Ile Lys
            100                 105
```

<210> SEQ ID NO 29
<211> LENGTH: 348
<212> TYPE: DNA
<213> ORGANISM: Mus sp.

<400> SEQUENCE: 29

```
gaagtgaaac tggtggagtc tgggggaggc ttagtgaagc ctggagggtc cctgaaactc      60
tcctgtgcag cctctggatt cactttcagg agctatggca tgtcttgggc tcgccagatt     120
ccagagaaga ggctggagtg ggtcgcatcc attagtagtg gtggaaccac ctactatcta     180
gggagtgtgc agggccgatt cacaatctcc agagataatg ccaggaacat cctgtacctg     240
caaatgagca gtctgaggtc tgaggacacg gccatgtatt attgtgcaag aggctatgat     300
gcgggatttg cttactgggg ccaagggact ctggtcagtg tctctgaa                   348
```

<210> SEQ ID NO 30
<211> LENGTH: 116
<212> TYPE: PRT
<213> ORGANISM: Mus sp.

<400> SEQUENCE: 30

```
Glu Val Lys Leu Val Glu Ser Gly Gly Gly Leu Val Lys Pro Gly Gly
 1               5                  10                  15
Ser Leu Lys Leu Ser Cys Ala Ala Ser Gly Phe Thr Phe Arg Ser Tyr
            20                  25                  30
Gly Met Ser Trp Ala Arg Gln Ile Pro Glu Lys Arg Leu Glu Trp Val
        35                  40                  45
Ala Ser Ile Ser Ser Gly Gly Thr Thr Tyr Tyr Leu Gly Ser Val Gln
    50                  55                  60
Gly Arg Phe Thr Ile Ser Arg Asp Asn Ala Arg Asn Ile Leu Tyr Leu
 65                  70                  75                  80
Gln Met Ser Ser Leu Arg Ser Glu Asp Thr Ala Met Tyr Tyr Cys Ala
                85                  90                  95
Arg Gly Tyr Asp Ala Gly Phe Ala Tyr Trp Gly Gln Gly Thr Leu Val
            100                 105                 110
Ser Val Ser Glu
        115
```

<210> SEQ ID NO 31
<211> LENGTH: 333
<212> TYPE: DNA
<213> ORGANISM: Mus sp.

<400> SEQUENCE: 31

```
gacattgtgc tgacacagtc tcctgcttcc ttagctgtat ctctggggca gagggccacc      60
atctcatgca gggccagcca aagtgtcagt acatctagct atagttatat gcactggtac     120
caacagaaac caggacagcc tcccaaactc ctcatcaagt atgcatccaa cctagaatct     180
ggggtccctg ccaggttcag tggcagtggg tctgggacag acttcaccct caacatccat     240
```

```
cctgtggagg aggaggatac tgcaacatat tactgtcaga acagttggga gattccgtac    300
acgttcggag gggggaccaa gctggaaata aaa                                 333
```

<210> SEQ ID NO 32
<211> LENGTH: 111
<212> TYPE: PRT
<213> ORGANISM: Mus sp.

<400> SEQUENCE: 32

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln Asn Ser Trp
                85                  90                  95

Glu Ile Pro Tyr Thr Phe Gly Gly Gly Thr Lys Leu Glu Ile Lys
            100                 105                 110

<210> SEQ ID NO 33
<211> LENGTH: 351
<212> TYPE: DNA
<213> ORGANISM: Mus sp.

<400> SEQUENCE: 33

```
gaggtgcagc ttcaggagtc aggacctagc ctcgtcaaac cttctcagac tctgtccctc    60
acctgttctg tcactggcga ctccatcacc agtggttact ggacctggat ccggaaattc    120
ccagggaata acttgaata catgggatac ataagctaca ctggtagcac ttactacaat    180
ccatctctca aaagtcgaat ctccatctct cgagacacat ccaagagcca gtactacctg    240
cagttgaatt ctgtgactac tgaggacaca gccacatatt actgtgcaag acagagggat    300
tggttagggt ttgcttactg gggccaaggg actctggtca ctgtctctgc a             351
```

<210> SEQ ID NO 34
<211> LENGTH: 117
<212> TYPE: PRT
<213> ORGANISM: Mus sp.

<400> SEQUENCE: 34

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Thr Trp Ile Arg Lys Phe Pro Gly Asn Lys Leu Glu Tyr Met
        35                  40                  45

Gly Tyr Ile Ser Tyr Thr Gly Ser Thr Tyr Tyr Asn Pro Ser Leu Lys
    50                  55                  60

Ser Arg Ile Ser Ile Ser Arg Asp Thr Ser Lys Ser Gln Tyr Tyr Leu
65                  70                  75                  80

Gln Leu Asn Ser Val Thr Thr Glu Asp Thr Ala Thr Tyr Tyr Cys Ala
                85                  90                  95

Arg Gln Arg Asp Trp Leu Gly Phe Ala Tyr Trp Gly Gln Gly Thr Leu
            100                 105                 110

Val Thr Val Ser Ala
        115

<210> SEQ ID NO 35
<211> LENGTH: 339
<212> TYPE: DNA
<213> ORGANISM: Mus sp.

<400> SEQUENCE: 35
gatattgtga tgacacagac tccatcctcc ctagctgtgt cacttggaga gaaggttact    60
atgagctgca agtccagtca gagccttta tatagtagca atcaaaagaa ctccttggcc   120
tggtaccagc agaaaccagg acagtctcct aaactgctga tttactgggc atccaatagg   180
gaatctgggg tccctgatcg cttcacaggc agtagctctg ggacagattt cactctcacc   240
atcagcagtg tgaaggctga agacctggca gtttattact gtcagcaata ttatagctat   300
ccgctcacgt tcggtgctgg gaccaagctg gagctgaaa                          339

<210> SEQ ID NO 36
<211> LENGTH: 113
<212> TYPE: PRT
<213> ORGANISM: Mus sp.

<400> SEQUENCE: 36

Asp Ile Val Met Thr Gln Thr Pro Ser Ser Leu Ala Val Ser Leu Gly
1               5                   10                  15

Glu Lys Val Thr Met Ser Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Ser Pro Lys Leu Leu Ile Tyr Trp Ala Ser Asn Arg Glu Ser Gly Val
    50                  55                  60

Pro Asp Arg Phe Thr Gly Ser Ser Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
            100                 105                 110

Lys

<210> SEQ ID NO 37
<211> LENGTH: 348
<212> TYPE: DNA
<213> ORGANISM: Mus sp.

<400> SEQUENCE: 37
gaagagaagc tggtggagtc tgggggaggc ttagtgaagc ctggagggtc cctgaaactc    60
tcctgtgcag cctctggatt cagtttcagt agttatggca tgtcttgggt tcgtcagact   120
ccagagaaga ggctggagtg gtcgcatcc atcagtagtg gtggtagtat ctactatcca   180
gacagtgtga agggccgatt caccatctcc agagataatg ccaggaacat cctgtacctg   240
caaatgagca gtctgaggtc tgaggacacg gccatgtatt attgtgcaag aggctatgat   300
gcggggtttg ctttctgggg ccaagggaca ctggtcactg cctctgca                348

-continued

<210> SEQ ID NO 38
<211> LENGTH: 116
<212> TYPE: PRT
<213> ORGANISM: Mus sp.

<400> SEQUENCE: 38

Glu Glu Lys Leu Val Glu Ser Gly Gly Gly Leu Val Lys Pro Gly Gly
1               5                   10                  15

Ser Leu Lys Leu Ser Cys Ala Ala Ser Gly Phe Ser Phe Ser Ser Tyr
            20                  25                  30

Gly Met Ser Trp Val Arg Gln Thr Pro Glu Lys Arg Leu Glu Trp Val
        35                  40                  45

Ala Ser Ile Ser Ser Gly Gly Ser Ile Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Gly Tyr Asp Ala Gly Phe Ala Phe Trp Gly Gln Gly Thr Leu Val
            100                 105                 110

Thr Ala Ser Ala
        115

<210> SEQ ID NO 39
<211> LENGTH: 333
<212> TYPE: DNA
<213> ORGANISM: Mus sp.

<400> SEQUENCE: 39
gacattgtgc tgacacagtc tcctgcttcc ttagctgtat ctctggggca gagggccacc      60
atctcatgca gggccagcca agtgtcagt acatctagtt atagttatgt gcactggtac      120
caacagaaac caggacagcc acccaaactc ctcatcaagt atgcatccaa cctagaatct     180
ggggtccctg ccaggttcag tggcagtggg tctgggacag acttcaccct caacatccat     240
cctgtggagg aggaggatac tgcaacatat tactgtcagc acagttggga gattccgtac     300
acgttcggag gggggaccaa gctggaaata aaa                                  333

<210> SEQ ID NO 40
<211> LENGTH: 111
<212> TYPE: PRT
<213> ORGANISM: Mus sp.

<400> SEQUENCE: 40

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Val His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110

<210> SEQ ID NO 41
<211> LENGTH: 348
<212> TYPE: DNA
<213> ORGANISM: Artificial Sequence
<220> FEATURE:
<223> OTHER INFORMATION: Humanized 5G11 antibody heavy chain variable
      region sequence

<400> SEQUENCE: 41

```
cagatcacac tgaaagaaag cggccctacc ctggtcaagc caactcagac cctgacactg     60
acttgcaccg tgtctgggtt ctctctgagt acatacggag tccactgtga caggcagccc    120
cctggcaaag ctctggagtg gctgggagtg atttggcggg gcgtcaccac agactataac    180
gccgctttta tgtcaagact gacaatcact aaggataaca gcaaaaatca ggtggtcctg    240
accatgaaca atatggaccc cgtggatacc gcaacatact attgtgcccg ctgggggttc    300
tacgccatgg actattgggg ccaggggact ctggtgaccg tctcgagc                 348
```

<210> SEQ ID NO 42
<211> LENGTH: 116
<212> TYPE: PRT
<213> ORGANISM: Artificial Sequence
<220> FEATURE:
<223> OTHER INFORMATION: Humanized 5G11 antibody heavy chain variable
      region sequence

<400> SEQUENCE: 42

```
Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
            20                  25                  30

Gly Val His Trp Ile Arg Gln Pro Pro Gly Lys Ala Leu Glu Trp Leu
        35                  40                  45

Gly Val Ile Trp Arg Gly Val Thr Thr Asp Tyr Asn Ala Ala Phe Met
    50                  55                  60

Ser Arg Leu Thr Ile Thr Lys Asp Asn Ser Lys Asn Gln Val Val Leu
65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser
        115
```

<210> SEQ ID NO 43
<211> LENGTH: 321
<212> TYPE: DNA
<213> ORGANISM: Artificial Sequence
<220> FEATURE:
<223> OTHER INFORMATION: Humanized 5G11 antibody light chain variable
      region sequence

<400> SEQUENCE: 43

```
gatatccaga tgactcagtc tccaagcagc ctgtctgcat ctgtggggga cagggtcacc     60
atcacatgca aagcatctca gagtgtgtca acgatgtcg cctggtacca gcagaagccc    120
ggaaaagctc ctaagctgct gatttactat gccgctaatc ggtacactgg cgtgccagac    180
agattcagcg gatccggata tggaaccgat ttcactttta ccatcagctc cctgcagcca    240
gaggacattg ccacatattt ctgtcagcag gattacacaa gcccctatac ttttggccag    300
```

```
gggaccaaac tggaaatcaa g                                              321
```

<210> SEQ ID NO 44
<211> LENGTH: 107
<212> TYPE: PRT
<213> ORGANISM: Artificial Sequence
<220> FEATURE:
<223> OTHER INFORMATION: Humanized 5G11 antibody light chain variable
      region sequence

<400> SEQUENCE: 44

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ala Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Thr Ser Pro Tyr
                85                  90                  95

Thr Phe Gly Gln Gly Thr Lys Leu Glu Ile Lys
            100                 105
```

<210> SEQ ID NO 45
<211> LENGTH: 348
<212> TYPE: DNA
<213> ORGANISM: Artificial Sequence
<220> FEATURE:
<223> OTHER INFORMATION: Humanized 13C5 antibody heavy chain variable
      region sequence

<400> SEQUENCE: 45

```
gaggtgcagc tggtcgagtc aggagggggg ctggtcaagc caggagggtc actgcgactg    60
agctgcgcag cttccgggtt catctttagg tcttatggca tgagttgggt gcgccaggca   120
ccagggaaag gactggagtg ggtcgcttca atcagctccg gaggcagcac ttactatcct   180
gactccgtga agggccggtt caccatttct agagataacg ccaaaaatag tctgtacctg   240
cagatgaact ctctgcgagc agaagacaca gccgtctacg attgtgctag aggatatgac   300
agcggctttg catactgggg ccaggggacc ctggtgacag tctcgagc               348
```

<210> SEQ ID NO 46
<211> LENGTH: 116
<212> TYPE: PRT
<213> ORGANISM: Artificial Sequence
<220> FEATURE:
<223> OTHER INFORMATION: Humanized 13C5 antibody heavy chain variable
      region sequence

<400> SEQUENCE: 46

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Arg Ser Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
```

```
            50                  55                  60
Gly Arg Phe Thr Ile Ser Arg Asp Asn Ala Lys Asn Ser Leu Tyr Leu
 65                  70                  75                  80

Gln Met Asn Ser Leu Arg Ala Glu Asp Thr Ala Val Tyr Asp Cys Ala
                 85                  90                  95

Arg Gly Tyr Asp Ser Gly Phe Ala Tyr Trp Gly Gln Gly Thr Leu Val
            100                 105                 110

Thr Val Ser Ser
        115

<210> SEQ ID NO 47
<211> LENGTH: 333
<212> TYPE: DNA
<213> ORGANISM: Artificial Sequence
<220> FEATURE:
<223> OTHER INFORMATION: Humanized 13C5 antibody light chain variable
      region sequence

<400> SEQUENCE: 47
gacattgtgc tgactcagag ccccgcttca ctggcagtgt ctccagggca gcgggcaacc      60
atcacatgca gagcctcaca gagcgtctcc accagctcct ctagtttcat gcactggtac     120
cagcagaagc ccggacagcc ccctaagctg ctgatcaaat atgctagcaa cctggagtcc     180
ggcgtgccag ccaggttctc tggcagtggg tcaggaaccg acttactct gaccattaat      240 cccgtcgaag ccaacgatac agctaattac tattgtcagc attcctggga gatcccttac     300
acatttggcc aggggactaa gctggagatc aag                                   333

<210> SEQ ID NO 48
<211> LENGTH: 111
<212> TYPE: PRT
<213> ORGANISM: Artificial Sequence
<220> FEATURE:
<223> OTHER INFORMATION: Humanized 13C5 antibody light chain variable
      region sequence

<400> SEQUENCE: 48

Asp Ile Val Leu Thr Gln Ser Pro Ala Ser Leu Ala Val Ser Pro Gly
  1               5                  10                  15

Gln Arg Ala Thr Ile Thr Cys Arg Ala Ser Gln Ser Val Ser Thr Ser
             20                  25                  30

Ser Ser Ser Phe Met His Trp Tyr Gln Gln Lys Pro Gly Gln Pro Pro
         35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asn Asp Thr Ala Asn Tyr Tyr Cys Gln His Ser Trp
                 85                  90                  95

Glu Ile Pro Tyr Thr Phe Gly Gln Gly Thr Lys Leu Glu Ile Lys
            100                 105                 110

<210> SEQ ID NO 49
<211> LENGTH: 1329
<212> TYPE: DNA
<213> ORGANISM: Artificial Sequence
<220> FEATURE:
<223> OTHER INFORMATION: 8C6-IgG4 (F234A/L235A) chimeric antibody heavy
      chain full length sequence

<400> SEQUENCE: 49
```

```
caggtgcagc tgaagcagtc aggacctggc ctagtgcagc cctcacagag cctgtccatc    60
acctgcacag tctctggttt ctcattaact agctatggtg tacactgggt tcgccagtct   120
ccaggaaagg gtctggagtg gctgggagtg atatggagtg gtggagtcac agactataat   180
gcagctttca tatccagact gagcatcagc aaggacaatt ccaagagcca agttttcttt   240
aaaatgaaca gtctgcaagc taatgacaca gccatatatt actgtgccag actcggtttc   300
tatgctatgg actactgggg tcaaggaacc tcagtcaccg tctcgagcgc ctccaccaag   360
ggacccagcg tgtttcccct ggccccctgt tccagatcca cctccgaaag cacagccgct   420
ctcggctgcc tggtcaagga ttacttccct gagcccgtga cagtctcctg gaatagcggc   480
gctctgacct ccggcgtgca taccttccct gctgtgctgc aatcctccgg actgtacagc   540
ctgagcagcg tggtcaccgt gccttcctcc agcctgggaa ccaaaaccta catgtgcaac   600
gtggaccaca agcccagcaa caccaaagtg gacaagaggg tggagtccaa gtacggaccc   660
ccttgtcctc cctgccctgc tcctgaagcc gctggaggac ctagcgtgtt cctgtttccc   720
cccaagccca aggacaccct catgatctcc aggacccccg aggtgacctg tgtcgtggtg   780
gacgtgagcc aagaggaccc cgaggtgcag ttcaactggt acgtggatgg cgtcgaggtc   840
cataacgcca agaccaagcc tagggaggag cagttcaaca gcacctacag agtggtgagc   900
gtcctgaccg tgctccacca agactggctg aacggcaagg aatacaagtg caaggtctcc   960
aacaagggac tcccttcctc catcgagaag accatcagca aggccaaggg ccagcccaga  1020
gaaccccaag tctacacact gccccccagc caagaggaaa tgaccaagaa ccaggtgagc  1080
ctgacctgcc tggtgaaagg cttctacccc agcgacattg ctgtcgaatg ggagagcaac  1140
ggccaacccg agaacaacta caagaccacc ccccctgtgc tcgacagcga cggctccttc  1200
ttcctctaca gcaggctgac agtggacaag tccaggtggc agagggcaa tgtcttcagc  1260
tgtagcgtca tgcacgaggc cctccacaac cactacaccc agaagagcct gtccctctcc  1320
ctgggctga                                                           1329
```

<210> SEQ ID NO 50
<211> LENGTH: 442
<212> TYPE: PRT
<213> ORGANISM: Artificial Sequence
<220> FEATURE:
<223> OTHER INFORMATION: 8C6-IgG4 (F234A/L235A) chimeric antibody heavy
      chain full length sequence

<400> SEQUENCE: 50

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Val Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Leu Gly Phe Tyr Ala Met Asp Tyr Trp Gly Gln Gly Thr Ser Val
            100                 105                 110

Thr Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 51
<211> LENGTH: 645
<212> TYPE: DNA
<213> ORGANISM: Artificial Sequence
<220> FEATURE:
<223> OTHER INFORMATION: 8C6 chimeric antibody light chain full length
      sequence

<400> SEQUENCE: 51
agtattgtga tgacccagac tcccaaattc ctacttgtat cagcaggaga cagggttacc      60
ataacctgca aggccagtca gagtgtgagt aatgatgtag gttggtacca acagaagcca     120
gggcagtctc ctaaactact gatatactat gcatccaatc gctactctgg agtccctgat     180

```
cgcttcactg gcagtggata tgggacggat ttcactttca ccatcagcac tgtgcaggct    240
gaagacctgg cagtttattt ctgtcaacaa gattatacct ctccgtacac gttcggaggg    300
gggaccaagc tggaaataaa acgtacggtg gccgcaccaa gcgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagctttaac agaggcgagt gctga    645
```

<210> SEQ ID NO 52
<211> LENGTH: 214
<212> TYPE: PRT
<213> ORGANISM: Artificial Sequence
<220> FEATURE:
<223> OTHER INFORMATION: 8C6 chimeric antibody light chain full length
      sequence

<400> SEQUENCE: 52

```
Ser Ile Val Met Thr Gln Thr Pro Lys Phe Leu Leu Val Ser Ala Gly
 1               5                   10                  15

Asp Arg Val Thr Ile Thr Cys Lys Ala Ser Gln Ser Val Ser Asn Asp
            20                  25                  30

Val Gly Trp Tyr Gln Gln Lys Pro Gly Gln Ser Pro Lys Leu Leu Ile
        35                  40                  45

Tyr Tyr Ala Ser Asn Arg Tyr Ser Gly Val Pro Asp Arg Phe Thr Gly
 50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Thr Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 53
<211> LENGTH: 1329
<212> TYPE: DNA
<213> ORGANISM: Artificial Sequence
<220> FEATURE:
<223> OTHER INFORMATION: 8H4-IgG4 (F234A/L235A) chimeric antibody heavy
      chain full length sequence

<400> SEQUENCE: 53

```
gaagtgaaac tggtggagtc tgggggaggc ttagtgaagc ctggagggtc cctgaaactc      60
tcctgtgcag cctctggatt cactttcagg agctatggca tgtcttgggc tcgccagatt     120
ccagagaaga ggctggagtg gtcgcatcc attagtagtg gtggaaccac ctactatcta     180
gggagtgtgc agggccgatt cacaatctcc agagataatg ccaggaacat cctgtacctg     240
caaatgagca gtctgaggtc tgaggacacg gccatgtatt attgtgcaag aggctatgat     300
gcgggatttg cttactgggg ccaagggact ctggtcagtg tctcgagcgc tccaccaag     360
ggacccagcg tgtttcccct ggccccctgt ccagatcca cctccgaaag cacagccgct     420
ctcggctgcc tggtcaagga ttacttccct gagcccgtga cagtctcctg aatagcggc     480
gctctgacct ccggcgtgca taccttccct gctgtgctgc aatcctccgg actgtacagc     540
ctgagcagcg tggtcaccgt gccttcctcc agcctgggaa ccaaaaccta cacatgcaac     600
gtggaccaca gcccagcaa caccaaagtg acaagaggg tggagtccaa gtacggaccc      660
ccttgtcctc cctgccctgc tcctgaagcc gctggaggac ctagcgtgtt cctgtttccc     720
cccaagccca aggacaccct catgatctcc aggaccccg aggtgacctg tgtcgtggtg     780
gacgtgagcc aagaggaccc cgaggtgcag ttcaactggt acgtggatgg cgtcgaggtc     840
cataacgcca agaccaagcc tagggaggag cagttcaaca gcacctacag agtggtgagc     900
gtcctgaccg tgctccacca agactggctg aacggcaagg aatacaagtg caaggtctcc     960
aacaagggac tcccttcctc catcgagaag accatcagca aggccaaggg ccagccccaga    1020
gaacccaag tctacacact gccccccagc caagaggaaa tgaccaagaa ccaggtgagc     1080
ctgacctgcc tggtgaaagg cttctacccc agcgacattg ctgtcgaatg ggagagcaac    1140
ggccaacccg agaacaacta caagaccacc cccctgtgc tcgacagcga cggctccttc     1200
ttcctctaca gcaggctgac agtggacaag tccaggtggc agagggcaa tgtcttcagc    1260
tgtagcgtca tgcacgaggc cctccacaac cactacaccc cagaagagcct gtccctctcc    1320
ctgggctga                                                               1329
```

<210> SEQ ID NO 54
<211> LENGTH: 442
<212> TYPE: PRT
<213> ORGANISM: Artificial Sequence
<220> FEATURE:
<223> OTHER INFORMATION: 8H4-IgG4 (F234A/L235A) chimeric antibody heavy
      chain full length sequence

<400> SEQUENCE: 54

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Arg Ser Tyr
            20                  25                  30

Gly Met Ser Trp Ala Arg Gln Ile Pro Glu Lys Arg Leu Glu Trp Val
        35                  40                  45

Ala Ser Ile Ser Ser Gly Gly Thr Thr Tyr Tyr Leu Gly Ser Val Gln
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg Gly Tyr Asp Ala Gly Phe Ala Tyr Trp Gly Gln Gly Thr Leu Val
            100                 105                 110
```

Ser Val Ser Ser Ala Ser Thr Lys Gly Pro Ser Val Phe Pro Leu Ala
            115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205

Lys Val Asp Lys Arg Val Glu Ser Lys Tyr Gly Pro Pro Cys Pro Pro
    210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 55
<211> LENGTH: 657
<212> TYPE: DNA
<213> ORGANISM: Artificial Sequence
<220> FEATURE:
<223> OTHER INFORMATION: 8H4 chimeric antibody light chain full length
      sequence

<400> SEQUENCE: 55
gacattgtgc tgacacagtc tcctgcttcc ttagctgtat ctctggggca gagggccacc      60
atctcatgca gggccagcca aagtgtcagt acatctagct atagttatat gcactggtac     120

```
caacagaaac caggacagcc tcccaaactc ctcatcaagt atgcatccaa cctagaatct    180
ggggtccctg ccaggttcag tggcagtggg tctgggacag acttcaccct caacatccat    240
cctgtggagg aggaggatac tgcaacatat tactgtcaga acagttggga gattccgtac    300
acgttcggag gggggaccaa gctggaaata aaacgtacgg tggccgcacc aagcgtcttc    360
atcttcccgc catctgatga gcagttgaaa tctggaactg cctctgttgt gtgcctgctg    420
aataacttct atcccagaga ggccaaagta cagtggaagg tggataacgc cctccaatcg    480
ggtaactccc aggagagtgt cacagagcag gacagcaagg acagcaccta cagcctcagc    540
agcaccctga cgctgagcaa agcagactac gagaaacaca agtctacgc ctgcgaagtc    600 acccatcagg gcctgagctc gcccgtcaca aagagcttta cagaggcga gtgctga      657
```

<210> SEQ ID NO 56
<211> LENGTH: 218
<212> TYPE: PRT
<213> ORGANISM: Artificial Sequence
<220> FEATURE:
<223> OTHER INFORMATION: 8H4 chimeric antibody light chain full length
      sequence

<400> SEQUENCE: 56

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln Asn Ser Trp
                85                  90                  95

Glu Ile Pro Tyr Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 57
<211> LENGTH: 1341
<212> TYPE: DNA
<213> ORGANISM: Artificial Sequence
<220> FEATURE:
<223> OTHER INFORMATION: 5G11-IgG1 (D265A) chimeric antibody heavy chain
      full length sequence

<400> SEQUENCE: 57

```
caggtgcagc tgaagcagtc aggacctggc ctagtgcagc cctcacagag cctgtccatc      60
acctgcacag tctctggttt ctcattaact acctatggtg tacactgggt tcgccagtct     120
ccaggaaagg gtctggaatg gctgggagtg atatggcgtg gtgtaaccac agactataat     180
gcagctttca tgtccagact gaccatcacc aaggacaatt ccaagagcca gttttctttt     240
aaaatgaaca gtctgcaagc taatgacaca gccatatatt actgtgccag actgggtttc     300
tatgctatgg actactgggg tcaaggaacc tcagtcaccg tctcgagcgc ctccactaag     360
ggcccatccg tgttccctct ggcaccctcc agcaagagca agcggagg caccgccgca       420
ctgggctgcc tcgtgaagga ctacttccca gaacccgtga ccgtcagctg aatagcggc      480
gctctgacca gcggagtcca cactttcccg cagtgctgc agtccagcgg cctgtacagc     540
ctgagcagcg tggtcactgt gccaagcagc agcctgggca ctcagaccta catctgcaac     600
gtcaaccaca gcccagcaa cacaaaggtg gacaagaagg tcgagcccaa gtcctgcgat      660
aagacccaca cctgccctcc atgtcccgcc ccgagctgc tgggaggacc cagcgtcttc      720
ctgtttcccc ccaagccaaa ggacaccctg atgatcagca ggaccccga agtgacctgc      780
gtcgtggtgg ccgtgagcca cgaagatccc gaggtgaagt tcaactggta cgtggacggc     840
gtggaagtgc acaacgccaa gacaaaaccc agggaggagc agtatgccag cacctacagg     900
gtcgtgagcg tcctgaccgt gctgcaccaa gactggctga acggcaagga gtataagtgc     960
aaggtgagca caaggcact gcccgccccc atcgagaaga ccatttccaa ggccaagggg     1020
caacctaggg agccacaggt ctacactctg cccctagca gggacgagct gaccaagaac    1080
caggtctccc tgacttgcct ggtgaagggg ttttatccca gcgacatcgc cgtcgagtgg    1140
gagagcaatg gccagcccga aaacaactac aagaccacac ccctgtgct ggacagcgac    1200
ggcagcttct ttctgtatag caaactgaca gtggataaga gcagatggca gcagggcaac    1260
gtgttctcct gctccgtgat gcacgaggcc ctgcacaatc actacaccca gaagtccctg    1320
agcctgtccc ccggaaaatg a                                              1341
```

<210> SEQ ID NO 58
<211> LENGTH: 446
<212> TYPE: PRT
<213> ORGANISM: Artificial Sequence
<220> FEATURE:
<223> OTHER INFORMATION: 5G11-IgG1 (D265A) chimeric antibody heavy chain full length sequence

<400> SEQUENCE: 58

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
                20                  25                  30

Gly Val His Trp Val Arg Gln Ser Pro Gly Lys Gly Leu Glu Trp Leu
            35                  40                  45

Gly Val Ile Trp Arg Gly Val Thr Thr Asp Tyr Asn Ala Ala Phe Met
        50                  55                  60

Ser Arg Leu Thr Ile Thr Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Leu Gly Phe Tyr Ala Met Asp Tyr Trp Gly Gln Gly Thr Ser Val
```

```
            100                 105                 110
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Val Glu Pro Lys Ser Cys Asp Lys Thr His Thr
210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Ala Val Ser His Glu Asp Pro Glu Val
                260                 265                 270
Lys Phe Asn Trp Tyr Val Asp Gly Val Glu Val His Asn Ala Lys Thr
                275                 280                 285
Lys Pro Arg Glu Glu Gln Tyr Ala Ser Thr Tyr Arg Val Val Ser Val
                290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
                340                 345                 350
Ser Arg Asp Glu Leu Thr Lys Asn Gln Val Ser Leu Thr Cys Leu Val
                355                 360                 365
Lys Gly Phe Tyr Pro Ser Asp Ile Ala Val Glu Trp Glu Ser Asn Gly
370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys
                435                 440                 445

<210> SEQ ID NO 59
<211> LENGTH: 1329
<212> TYPE: DNA
<213> ORGANISM: Artificial Sequence
<220> FEATURE:
<223> OTHER INFORMATION: 5G11-IgG4 (F234A/L235A) chimeric antibody heavy
      chain full length sequence

<400> SEQUENCE: 59
caggtgcagc tgaagcagtc aggacctggc ctagtgcagc cctcacagag cctgtccatc     60
acctgcacag tctctggttt ctcattaact acctatggtg tacactgggt tcgccagtct    120
```

```
ccaggaaagg gtctggaatg gctgggagtg atatggcgtg gtgtaaccac agactataat      180
gcagctttca tgtccagact gaccatcacc aaggacaatt ccaagagcca agttttcttt      240
aaaatgaaca gtctgcaagc taatgacaca gccatatatt actgtgccag actgggtttc      300
tatgctatgg actactgggg tcaaggaacc tcagtcaccg tctcgagcgc ctccaccaag      360
ggacccagcg tgtttcccct ggcccccgt tccagatcca cctccgaaag cacagccgct       420
ctcggctgcc tggtcaagga ttacttccct gagcccgtga cagtctcctg gaatagcggc      480
gctctgacct ccggcgtgca taccttccct gctgtgctgc aatcctccgg actgtacagc      540
ctgagcagcg tggtcaccgt gccttcctcc agcctgggaa ccaaaaccta cacatgcaac      600
gtggaccaca gcccagcaa caccaaagtg gacaagaggg tggagtccaa gtacggaccc       660
ccttgtcctc cctgccctgc tcctgaagcc gctggaggac ctagcgtgtt cctgtttccc      720
cccaagccca aggacaccct catgatctcc aggacccccg aggtgacctg tgtcgtggtg      780
gacgtgagcc aagaggaccc cgaggtgcag ttcaactggt acgtggatgg cgtcgaggtc      840
cataacgcca agaccaagcc tagggaggag cagttcaaca gcacctacag agtggtgagc      900
gtcctgaccg tgctccacca agactggctg aacggcaagg aatacaagtg caaggtctcc      960
aacaagggac tcccttcctc catcgagaag accatcagca aggccaaggg ccagcccaga     1020 gaacccaag tctacacact gccccccagc caagaggaaa tgaccaagaa ccaggtgagc      1080
ctgacctgcc tggtgaaagg cttctacccc agcgacattg ctgtcgaatg ggagagcaac     1140
ggccaacccg agaacaacta caagaccacc cccctgtgc tcgacagcga cggctccttc      1200
ttcctctaca gcaggctgac agtggacaag tccaggtggc agagggcaa tgtcttcagc       1260 tgtagcgtca tgcacgaggc cctccacaac cactacaccc agaagagcct gtccctctcc     1320
ctgggctga                                                            1329
```

<210> SEQ ID NO 60
<211> LENGTH: 442
<212> TYPE: PRT
<213> ORGANISM: Artificial Sequence
<220> FEATURE:
<223> OTHER INFORMATION: 5G11-IgG4 (F234A/L235A) chimeric antibody heavy
      chain full length sequence

<400> SEQUENCE: 60

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Thr Tyr
            20                  25                  30

Gly Val His Trp Val Arg Gln Ser Pro Gly Lys Gly Leu Glu Trp Leu
        35                  40                  45

Gly Val Ile Trp Arg Gly Val Thr Thr Asp Tyr Asn Ala Ala Phe Met
    50                  55                  60

Ser Arg Leu Thr Ile Thr Lys Asp Asn Ser Lys Ser Gln Val Phe Phe
65                  70                  75                  80

Lys Met Asn Ser Leu Gln Ala Asn Asp Thr Ala Ile Tyr Tyr Cys Ala
                85                  90                  95

Arg Leu Gly Phe Tyr Ala Met Asp Tyr Trp Gly Gln Gly Thr Ser Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu

```
                130             135             140
Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
                260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
                340                 345                 350

Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
                420                 425                 430

Thr Gln Lys Ser Leu Ser Leu Ser Leu Gly
            435                 440

<210> SEQ ID NO 61
<211> LENGTH: 645
<212> TYPE: DNA
<213> ORGANISM: Artificial Sequence
<220> FEATURE:
<223> OTHER INFORMATION: 5G11 chimeric antibody light chain full length
      sequence

<400> SEQUENCE: 61
agtattgtga tgacccagac tcccaaattc ctgcttgtat cagcaggaga cagggttacc    60
ataacctgca aggccagtca gagtgtgagt aatgatgtag cttggtacca gcagaagcca   120
gggcagtctc ctaaactgct gatatattat gcagccaatc gctacactgg agtccctgat   180
cgcttcactg gcagtggata tgggacggat tcacttttca ccatcagcat tgtgcaggct   240
gaagacctgg cagtttattt ctgtcagcag gattatacct ctccgtacac gttcggaggg   300
```

```
gggaccaagc tggaaataaa acgtacggtg ccgcaccaa gcgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag     480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagctttaac agaggcgagt gctga                   645
```

<210> SEQ ID NO 62
<211> LENGTH: 214
<212> TYPE: PRT
<213> ORGANISM: Artificial Sequence
<220> FEATURE:
<223> OTHER INFORMATION: 5G11 chimeric antibody light chain full length sequence

<400> SEQUENCE: 62

```
Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ala Asn Arg Tyr Thr Gly Val Pro Asp Arg Phe Thr Gly
    50                  55                  60

Ser Gly Tyr Gly Thr Asp Phe Thr Phe Thr Ile Ser Ile Val Gln Ala
65                  70                  75                  80

Glu Asp Leu Ala Val Tyr Phe Cys Gln Gln Asp Tyr Thr Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 63
<211> LENGTH: 1341
<212> TYPE: DNA
<213> ORGANISM: Artificial Sequence
<220> FEATURE:
<223> OTHER INFORMATION: 13C5-IgG1 (D265A) chimeric antibody heavy chain full length sequence

<400> SEQUENCE: 63

```
gaagtgaagc tggtggagtc tgggggaggc ttagtgaagc ctggagggtc cctgaaactc    60
```

```
tcctgtgcag cctctggatt cattttcaga agctatggca tgtcttgggt tcgccagact      120
ccagagaaga ggctggagtg ggtcgcatcc attagtagtg gtggtagcac ctactatcca      180
gacagtgtga agggccgatt caccatctcc agagataatg ccaggaacat cttgtacctg      240
caaatgagca gtctgaggtc tgaggacacg gccatgtatg actgtgcaag aggctatgat      300
tcggggtttg cttattgggg ccaagggact ctggtcactg tctcgagcgc ctccactaag      360
ggcccatccg tgttccctct ggcaccctcc agcaagagca agcggagg caccgccgca        420 ctgggctgcc tcgtgaagga ctacttccca gaacccgtga ccgtcagctg aatagcggc       480 gctctgacca gcggagtcca cactttcccc gcagtgctgc agtccagcgg cctgtacagc      540
ctgagcagcg tggtcactgt gccaagcagc agcctgggca ctcagaccta catctgcaac      600
gtcaaccaca gcccagcaa cacaaaggtg gacaagaagg tcgagcccaa gtcctgcgat       660
aagacccaca cctgccctcc atgtcccgcc cccgagctgc tgggaggacc cagcgtcttc      720
ctgtttcccc ccaagccaaa ggacaccctg atgatcagca ggaccccga agtgacctgc       780 gtcgtggtgg ccgtgagcca cgaagatccc gaggtgaagt tcaactggta cgtggacggc      840
gtggaagtgc acaacgccaa gacaaaaccc agggaggagc agtatgccag cacctacagg      900
gtcgtgagcg tcctgaccgt gctgcaccaa gactggctga acggcaagga gtataagtgc      960
aaggtgagca acaaggcact gcccgcccccc atcgagaaga ccatttccaa ggccaagggg    1020
caacctaggg agccacaggt ctacactctg cccccctagca gggacgagct gaccaagaac    1080
caggtctccc tgacttgcct ggtgaagggg ttttatccca gcgacatcgc cgtcgagtgg    1140
gagagcaatg gccagcccga aaacaactac aagaccacac cccctgtgct ggacagcgac    1200
ggcagcttct ttctgtatag caaactgaca gtggataaga gcagatggca gcaggcaac    1260 gtgttctcct gctccgtgat gcacgaggcc ctgcacaatc actacacccca gaagtccctg   1320 agcctgtccc ccggaaaatg a                                               1341
```

<210> SEQ ID NO 64
<211> LENGTH: 446
<212> TYPE: PRT
<213> ORGANISM: Artificial Sequence
<220> FEATURE:
<223> OTHER INFORMATION: 13C5-IgG1 (D265A) chimeric antibody heavy chain
      full length sequence

<400> SEQUENCE: 64

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ile Phe Arg Ser Tyr
            20                  25                  30

Gly Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Ala Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 65
<211> LENGTH: 1329
<212> TYPE: DNA
<213> ORGANISM: Artificial Sequence
<220> FEATURE:
<223> OTHER INFORMATION: 13C5-IgG4 (F234A/L235A) chimeric antibody heavy
      chain full length sequence

<400> SEQUENCE: 65
gaagtgaagc tggtggagtc tgggggaggc ttagtgaagc ctggagggtc cctgaaactc     60
tcctgtgcag cctctggatt cattttcaga agctatggca tgtcttgggt tcgccagact    120
ccagagaaga ggctggagtg ggtcgcatcc attagtagtg gtggtagcac ctactatcca    180
gacagtgtga agggccgatt caccatctcc agagataatg ccaggaacat cttgtacctg    240

```
caaatgagca gtctgaggtc tgaggacacg gccatgtatg actgtgcaag aggctatgat        300
tcggggtttg cttattgggg ccaagggact ctggtcactg tctcgagcgc ctccaccaag        360
ggacccagcg tgtttcccct ggccccctgt tccagatcca cctccgaaag cacagccgct        420
ctcggctgcc tggtcaagga ttacttccct gagcccgtga cagtctcctg gaatagcggc        480
gctctgacct ccggcgtgca taccttccct gctgtgctgc aatcctccgg actgtacagc        540
ctgagcagcg tggtcaccgt gccttcctcc agcctgggaa ccaaaaccta cacatgcaac        600
gtggaccaca agcccagcaa caccaaagtg gacaagaggg tggagtccaa gtacggaccc        660
ccttgtcctc cctgccctgc tcctgaagcc gctggaggac ctagcgtgtt cctgtttccc        720
cccaagccca aggacaccct catgatctcc aggaccccccg aggtgacctg tgtcgtggtg        780
gacgtgagcc aagaggaccc cgaggtgcag ttcaactggt acgtggatgg cgtcgaggtc        840
cataacgcca agaccaagcc tagggaggag cagttcaaca gcacctacag agtggtgagc        900
gtcctgaccg tgctccacca agactggctg aacggcaagg aatacaagtg caaggtctcc        960
aacaagggac tcccttcctc catcgagaag accatcagca aggccaaggg ccagcccaga       1020
gaaccccaag tctacacact gcccccccagc caagaggaaa tgaccaagaa ccaggtgagc       1080
ctgacctgcc tggtgaaagg cttctacccc agcgacattg ctgtcgaatg ggagagcaac       1140
ggccaacccg agaacaacta caagaccacc ccccctgtgc tcgacagcga cggctccttc       1200
ttcctctaca gcaggctgac agtggacaag tccaggtggc agagggcaa tgtcttcagc       1260 tgtagcgtca tgcacgaggc cctccacaac cactacaccc agaagagcct gtccctctcc       1320
ctgggctga                                                               1329
```

<210> SEQ ID NO 66
<211> LENGTH: 442
<212> TYPE: PRT
<213> ORGANISM: Artificial Sequence
<220> FEATURE:
<223> OTHER INFORMATION: 13C5-IgG4 (F234A/L235A) chimeric antibody heavy
      chain full length sequence

<400> SEQUENCE: 66

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Ile Phe Arg Ser Tyr
            20                  25                  30

Gly Met Ser Trp Val Arg Gln Thr Pro Glu Lys Arg Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Arg Asn Ile Leu Tyr Leu
65                  70                  75                  80

Gln Met Ser Ser Leu Arg Ser Glu Asp Thr Ala Met Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

| | | | | | | | | | | | | |
|---|---|---|---|---|---|---|---|---|---|---|---|---|
|Ala|Leu|Thr|Ser|Gly|Val|His|Thr|Phe|Pro|Ala|Val|Leu|Gln|Ser|Ser|
| | | | |165| | | |170| | | |175| | | |

Ala Leu Thr Ser Gly Val His Thr Phe Pro Ala Val Leu Gln Ser Ser
                165                 170                 175

Gly Leu Tyr Ser Leu Ser Ser Val Thr Val Pro Ser Ser Ser Leu
            180                 185                 190

Gly Thr Lys Thr Tyr Thr Cys Asn Val Asp His Lys Pro Ser Asn Thr
            195                 200                 205

Lys Val Asp Lys Arg Val Glu Ser Lys Tyr Gly Pro Pro Cys Pro Pro
        210                 215                 220

Cys Pro Ala Pro Glu Ala Ala Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser Gln Glu Asp Pro Glu Val Gln Phe Asn
            260                 265                 270

Trp Tyr Val Asp Gly Val Glu Val His Asn Ala Lys Thr Lys Pro Arg
            275                 280                 285

Glu Glu Gln Phe Asn Ser Thr Tyr Arg Val Val Ser Val Leu Thr Val
        290                 295                 300

Leu His Gln Asp Trp Leu Asn Gly Lys Glu Tyr Lys Cys Lys Val Ser
305                 310                 315                 320

Asn Lys Gly Leu Pro Ser Ser Ile Glu Lys Thr Ile Ser Lys Ala Lys
                325                 330                 335

Gly Gln Pro Arg Glu Pro Gln Val Tyr Thr Leu Pro Pro Ser Gln Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Arg Leu Thr Val Asp Lys Ser Arg Trp Gln Glu Gly
                405                 410                 415

Asn Val Phe Ser Cys Ser Val Met His Glu Ala Leu His Asn His Tyr
            420                 425                 430

Thr Gln Lys Ser Leu Ser Leu Ser Leu Gly
        435                 440

<210> SEQ ID NO 67
<211> LENGTH: 663
<212> TYPE: DNA
<213> ORGANISM: Artificial Sequence
<220> FEATURE:
<223> OTHER INFORMATION: 13C5 chimeric antibody light chain full length
      sequence

<400> SEQUENCE: 67

```
gacattgtgc tgacacagtc tcctgcttcc ttagctgttt ctctggggca gagggccacc    60
atctcatgca gggccagcca agtgtcagt acttctagct ctagttttat gcactggtac    120
caacagaaac caggacagcc acccaaactc ctcatcaagt atgcatccaa cctagaatct    180
ggggtccctg ccaggttcag tggcagtggg tctgggacag acttcaccct caacatccat    240
cctgtggagg aggaggatac tgcaacatat tactgtcagc acagttggga gattccgtac    300
acgttcggag gggggaccaa gctggaaata aaacgtacgc gtacggtggc cgcaccaagc    360
gtcttcatct tcccgccatc tgatgagcag ttgaaatctg gaactgcctc tgttgtgtgc    420
```

```
ctgctgaata acttctatcc cagagaggcc aaagtacagt ggaaggtgga taacgccctc    480
caatcgggta actcccagga gagtgtcaca gagcaggaca gcaaggacag cacctacagc    540
ctcagcagca ccctgacgct gagcaaagca gactacgaga aacacaaagt ctacgcctgc    600
gaagtcaccc atcagggcct gagctcgccc gtcacaaaga gctttaacag aggcgagtgc    660
tga                                                                  663
```

<210> SEQ ID NO 68
<211> LENGTH: 220
<212> TYPE: PRT
<213> ORGANISM: Artificial Sequence
<220> FEATURE:
<223> OTHER INFORMATION: 13C5 chimeric antibody light chain full length
      sequence

<400> SEQUENCE: 68

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Ser Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

Thr Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 69
<211> LENGTH: 1341
<212> TYPE: DNA
<213> ORGANISM: Artificial Sequence
<220> FEATURE:
<223> OTHER INFORMATION: Humanized 5G11-IgG1 (D265A) antibody heavy
      chain full length sequence

<400> SEQUENCE: 69

```
cagatcacac tgaaagaaag cggccctacc ctggtcaagc caactcagac cctgacactg    60
acttgcaccg tgtctggggtt ctctctgagt acatacggag tccactggat caggcagccc   120
cctggcaaag ctctggagtg gctgggagtg atttggcggg gcgtcaccac agactataac   180
```

```
gccgctttta tgtcaagact gacaatcact aaggataaca gcaaaaatca ggtggtcctg    240
accatgaaca atatggaccc cgtggatacc gcaacatact attgtgcccg gctggggttc    300
tacgccatgg actattgggg ccaggggact ctggtgaccg tctcgagcgc ctccactaag    360
ggcccatccg tgttccctct ggcaccctcc agcaagagca agcggagg caccgccgca      420 ctgggctgcc tcgtgaagga ctacttccca gaacccgtga ccgtcagctg aatagcggc    480 gctctgacca gcggagtcca cactttcccc gcagtgctgc agtccagcgg cctgtacagc    540
ctgagcagcg tggtcactgt gccaagcagc agcctgggca ctcagaccta catctgcaac    600
gtcaaccaca gcccagcaa cacaaaggtg gacaagaagg tcgagcccaa gtcctgcgat     660
aagacccaca cctgccctcc atgtcccgcc cccgagctgc tgggaggacc cagcgtcttc    720
ctgtttcccc ccaagccaaa ggacaccctg atgatcagca ggacccccga agtgacctgc    780
gtcgtggtgg ccgtgagcca cgaagatccc gaggtgaagt tcaactggta cgtggacggc    840
gtggaagtgc acaacgccaa gacaaaaccc agggaggagc agtataacag cacctacagg    900
gtcgtgagcg tcctgaccgt gctgcaccaa gactggctga acggcaagga gtataagtgc    960
aaggtgagca caaggcact gcccgccccc atcgagaaga ccatttccaa ggccaagggg    1020
caacctaggg agccacaggt ctacactctg cccctagca gggacgagct gaccaagaac    1080
caggtctccc tgacttgcct ggtgaagggg ttttatccca gcgacatcgc cgtcgagtgg    1140
gagagcaatg ccagcccga aaacaactac aagaccacac ccctgtgct ggacagcgac     1200 ggcagcttct ttctgtatag caaactgaca gtggataaga gcagatggca gcagggcaac    1260
gtgttctcct gctccgtgat gcacgaggcc ctgcacaatc actacaccca gaagtccctg    1320
agcctgtccc ccggaaaatg a                                              1341

<210> SEQ ID NO 70
<211> LENGTH: 446
<212> TYPE: PRT
<213> ORGANISM: Artificial Sequence
<220> FEATURE:
<223> OTHER INFORMATION: Humanized 5G11-IgG1 (D265A) antibody heavy
      chain full length sequence

<400> SEQUENCE: 70

Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
            20                  25                  30

Gly Val His Trp Ile Arg Gln Pro Gly Lys Ala Leu Glu Trp Leu
        35                  40                  45

Gly Val Ile Trp Arg Gly Val Thr Thr Asp Tyr Asn Ala Ala Phe Met
    50                  55                  60

Ser Arg Leu Thr Ile Thr Lys Asp Asn Ser Lys Asn Gln Val Val Leu
65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140
```

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
            195                 200                 205

Lys Val Asp Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
            260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 71
<211> LENGTH: 1329
<212> TYPE: DNA
<213> ORGANISM: Artificial Sequence
<220> FEATURE:
<223> OTHER INFORMATION: Humanized 5G11-IgG4 (F234A/L235A) antibody
      heavy chain full length sequence

<400> SEQUENCE: 71
cagatcacac tgaaagaaag cggccctacc ctggtcaagc caactcagac cctgacactg      60
acttgcaccg tgtctggggtt ctctctgagt acatacggag tccactggat caggcagccc     120
cctggcaaag ctctggagtg gctggagtg atttggcggg gcgtcaccac agactataac     180
gccgctttta tgtcaagact gacaatcact aaggataaca gcaaaaatca ggtggtcctg     240
accatgaaca atatggaccc cgtggatacc gcaacatact attgtgcccg gctgggttc     300 tacgccatgg actattgggg ccaggggact ctggtgaccg tctcgagcgc ctccaccaag     360

```
ggacccagcg tgtttcccct ggcccccctgt tccagatcca cctccgaaag cacagccgct    420
ctcggctgcc tggtcaagga ttacttccct gagcccgtga cagtctcctg aatagcggc     480 gctctgacct ccggcgtgca taccttccct gctgtgctgc aatcctccgg actgtacagc    540
ctgagcagcg tggtcaccgt gccttcctcc agcctgggaa ccaaaaccta cacatgcaac    600
gtggaccaca agcccagcaa caccaaagtg gacaagaggg tggagtccaa gtacggaccc    660
ccttgtcctc cctgccctgc tcctgaagcc gctggaggac ctagcgtgtt cctgtttccc    720
cccaagccca aggacaccct catgatctcc aggacccccg aggtgacctg tgtcgtggtg    780
gacgtgagcc aagaggaccc cgaggtgcag ttcaactggt acgtggatgg cgtcgaggtc    840
cataacgcca agaccaagcc tagggaggag cagttcaaca gcacctacag agtggtgagc    900
gtcctgaccg tgctccacca agactggctg aacggcaagg aatacaagtg caaggtctcc    960
aacaagggac tcccttcctc catcgagaag accatcagca aggccaaggg ccagcccaga   1020 gaacccaag tctacacact gccccccagc aagaggaaa tgaccaagaa ccaggtgagc      1080
ctgacctgcc tggtgaaagg cttctacccc agcgacattg ctgtcgaatg ggagagcaac   1140
ggccaacccg agaacaacta caagaccacc cccctgtgc tcgacagcga cggctccttc     1200
ttcctctaca gcaggctgac agtggacaag tccaggtggc aagagggcaa tgtcttcagc   1260
tgtagcgtca tgcacgaggc cctccacaac cactacaccc agaagagcct gtccctctcc   1320
ctgggctga                                                           1329

<210> SEQ ID NO 72
<211> LENGTH: 442
<212> TYPE: PRT
<213> ORGANISM: Artificial Sequence
<220> FEATURE:
<223> OTHER INFORMATION: Humanized 5G11-IgG4 (F234A/L235A) antibody
      heavy chain full length sequence

<400> SEQUENCE: 72

Gln Ile Thr Leu Lys Glu Ser Gly Pro Thr Leu Val Lys Pro Thr Gln
1               5                   10                  15

Thr Leu Thr Leu Thr Cys Thr Val Ser Gly Phe Ser Leu Ser Thr Tyr
                20                  25                  30

Gly Val His Trp Ile Arg Gln Pro Pro Gly Lys Ala Leu Glu Trp Leu
            35                  40                  45

Gly Val Ile Trp Arg Gly Val Thr Thr Asp Tyr Asn Ala Ala Phe Met
        50                  55                  60

Ser Arg Leu Thr Ile Thr Lys Asp Asn Ser Lys Asn Gln Val Val Leu
65                  70                  75                  80

Thr Met Asn Asn Met Asp Pro Val Asp Thr Ala Thr Tyr Tyr Cys Ala
                85                  90                  95

Arg Leu Gly Phe Tyr Ala Met Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
                180                 185                 190
Gly Thr Lys Thr Tyr Thr Cys Asn Val Asp His Lys Pro Ser Asn Thr
            195                 200                 205
Lys Val Asp Lys Arg Val Glu Ser Lys Tyr Gly Pro Pro Cys Pro Pro
        210                 215                 220
Cys Pro Ala Pro Glu Ala Ala Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
        275                 280                 285
Glu Glu Gln Phe Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Arg Leu Thr Val Asp Lys Ser Arg Trp Gln Glu Gly
                405                 410                 415
Asn Val Phe Ser Cys Ser Val Met His Glu Ala Leu His Asn His Tyr
            420                 425                 430
Thr Gln Lys Ser Leu Ser Leu Ser Leu Gly
        435                 440

<210> SEQ ID NO 73
<211> LENGTH: 645
<212> TYPE: DNA
<213> ORGANISM: Artificial Sequence
<220> FEATURE:
<223> OTHER INFORMATION: Humanized 5G11 antibody light chain full length
      sequence

<400> SEQUENCE: 73
gatatccaga tgactcagtc tccaagcagc ctgtctgcat ctgtggggga cagggtcacc      60
atcacatgca aagcatctca gagtgtgtca acgatgtcg cctggtacca gcagaagccc     120
ggaaaagctc ctaagctgct gatttactat gccgctaatc ggtacactgg cgtgccagac     180
agattcagcg gatccggata tggaaccgat ttcacttttaccatcagctc cctgcagcca     240 gaggacattg ccacatattt ctgtcagcag gattacacaa gcccctatac ttttggccag     300
gggaccaaac tggaaatcaa gcgtacggtg gccgcaccaa gcgtcttcat cttcccgcca     360
tctgatgagc agttgaaatc tggaactgcc tctgttgtgt gcctgctgaa taacttctat     420
cccagagagg ccaaagtaca gtggaaggtg ataacgccc tccaatcggg taactcccag     480
gagagtgtca cagagcagga cagcaaggac agcacctaca gcctcagcag caccctgacg     540
```

```
ctgagcaaag cagactacga gaaacacaaa gtctacgcct gcgaagtcac ccatcagggc      600
ctgagctcgc ccgtcacaaa gagctttaac agaggcgagt gctga                     645
```

<210> SEQ ID NO 74
<211> LENGTH: 214
<212> TYPE: PRT
<213> ORGANISM: Artificial Sequence
<220> FEATURE:
<223> OTHER INFORMATION: Humanized 5G11 antibody light chain full length
      sequence

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Lys Ala Pro Lys Leu Leu Ile
        35                  40                  45

Tyr Tyr Ala Ala Asn Arg Tyr Thr Gly Val Pro Asp Arg Phe Ser Gly
    50                  55                  60

Ser Gly Tyr Gly Thr Asp Phe Thr Phe Thr Ile Ser Ser Leu Gln Pro
65                  70                  75                  80

Glu Asp Ile Ala Thr Tyr Phe Cys Gln Gln Asp Tyr Thr Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 75
<211> LENGTH: 1341
<212> TYPE: DNA
<213> ORGANISM: Artificial Sequence
<220> FEATURE:
<223> OTHER INFORMATION: Humanized 13C5-IgG1 (D265A) antibody heavy
      chain full length sequence

<400> SEQUENCE: 75

```
gaggtgcagc tggtcgagtc aggagggggg ctggtcaagc caggagggtc actgcgactg      60
agctgcgcag cttccgggtt catctttagg tcttatggca tgagttgggt gcgccaggca     120
ccagggaaag gactggagtg ggtcgcttca atcagctccg gaggcagcac ttactatcct     180
gactccgtga aggccggttc accattttct agagataacg ccaaaaatag tctgtacctg     240
cagatgaact ctctgcgagc agaagacaca gccgtctacg attgtgctag aggatatgac     300
```

```
agcggctttg catactgggg ccaggggacc ctggtgacag tctcgagcgc ctccactaag    360
ggcccatccg tgttccctct ggcaccctcc agcaagagca caagcggagg caccgccgca    420
ctgggctgcc tcgtgaagga ctacttccca gaacccgtga ccgtcagctg gaatagcggc    480
gctctgacca gcggagtcca cactttcccc gcagtgctgc agtccagcgg cctgtacagc    540
ctgagcagcg tggtcactgt gccaagcagc agcctgggca ctcagaccta catctgcaac    600
gtcaaccaca agcccagcaa cacaaaggtg gacaagaagg tcgagcccaa gtcctgcgat    660
aagacccaca cctgccctcc atgtcccgcc ccgagctgc tgggaggacc cagcgtcttc    720
ctgtttcccc ccaagccaaa ggacaccctg atgatcagca ggaccccga agtgacctgc    780
gtcgtggtgg ccgtgagcca cgaagatccc gaggtgaagt tcaactggta cgtggacggc    840
gtggaagtgc acaacgccaa gacaaaaccc agggaggagc agtataacag cacctacagg    900
gtcgtgagcg tcctgaccgt gctgcaccaa gactggctga acggcaagga gtataagtgc    960
aaggtgagca acaaggcact gcccgccccc atcgagaaga ccatttccaa ggccaagggg   1020
caacctaggg agccacaggt ctacactctg cccctagca gggacgagct gaccaagaac    1080
caggtctccc tgacttgcct ggtgaagggg ttttatccca gcgacatcgc cgtcgagtgg   1140
gagagcaatg gccagcccga aaacaactac aagaccacac ccctgtgct ggacagcgac    1200
ggcagcttct ttctgtatag caaactgaca gtggataaga gcagatggca gcagggcaac   1260
gtgttctcct gctccgtgat gcacgaggcc ctgcacaatc actacaccca gaagtccctg   1320
agcctgtccc ccggaaaatg a                                             1341
```

<210> SEQ ID NO 76
<211> LENGTH: 446
<212> TYPE: PRT
<213> ORGANISM: Artificial Sequence
<220> FEATURE:
<223> OTHER INFORMATION: Humanized 13C5-IgG1 (D265A) antibody heavy chain full length sequence

<400> SEQUENCE: 76

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Arg Ser Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

```
Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Ala Val Ser His Glu Asp Pro Glu Val
                260                 265                 270

Lys Phe Asn Trp Tyr Val Asp Gly Val Glu Val His Asn Ala Lys Thr
            275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 77
<211> LENGTH: 1329
<212> TYPE: DNA
<213> ORGANISM: Artificial Sequence
<220> FEATURE:
<223> OTHER INFORMATION: Humanized 13C5-IgG4 (F234A/L235A) antibody
      heavy chain full length sequence

<400> SEQUENCE: 77
gaggtgcagc tggtcgagtc aggagggggg ctggtcaagc caggagggtc actgcgactg      60
agctgcgcag cttccgggtt catctttagg tcttatggca tgagttgggt cgcgccaggca    120 ccagggaaag gactggagtg gtcgcttca atcagctccg gaggcagcac ttactatcct     180
gactccgtga agggccggtt caccatttct agagataacg ccaaaaatag tctgtacctg    240
cagatgaact ctctgcgagc agaagacaca gccgtctacg attgtgctag aggatatgac    300
agcggctttg catactgggg ccagggggacc ctggtgacag tctcgagcgc ctccaccaag   360
ggacccagcg tgtttcccct ggccccccgt tccagatcca cctccgaaag cacagccgct    420
ctcggctgcc tggtcaagga ttacttccct gagcccgtga cagtctcctg gaatagcggc    480
```

```
gctctgacct ccggcgtgca taccttccct gctgtgctgc aatcctccgg actgtacagc    540
ctgagcagcg tggtcaccgt gccttcctcc agcctgggaa ccaaaaccta cacatgcaac    600
gtggaccaca agcccagcaa caccaaagtg gacaagaggg tggagtccaa gtacggaccc    660
ccttgtcctc cctgccctgc tcctgaagcc gctggaggac ctagcgtgtt cctgtttccc    720
cccaagccca aggacaccct catgatctcc aggaccccccg aggtgacctg tgtcgtggtg    780
gacgtgagcc aagaggaccc cgaggtgcag ttcaactggt acgtggatgg cgtcgaggtc    840
cataacgcca agaccaagcc tagggaggag cagttcaaca gcacctacag agtggtgagc    900
gtcctgaccg tgctccacca agactggctg aacggcaagg aatacaagtg caaggtctcc    960
aacaagggac tcccttcctc catcgagaag accatcagca aggccaaggg ccagcccaga   1020 gaacccaag tctacacact gccccccagc caagaggaaa tgaccaagaa ccaggtgagc   1080
ctgacctgcc tggtgaaagg cttctacccc agcgacattg ctgtcgaatg ggagagcaac   1140
ggccaacccg agaacaacta caagaccacc ccccctgtgc tcgacagcga cggctccttc   1200
ttcctctaca gcaggctgac agtggacaag tccaggtggc aagagggcaa tgtcttcagc   1260
tgtagcgtca tgcacgaggc cctccacaac cactacaccc agaagagcct gtccctctcc   1320
ctgggctga                                                           1329
```

<210> SEQ ID NO 78
<211> LENGTH: 442
<212> TYPE: PRT
<213> ORGANISM: Artificial Sequence
<220> FEATURE:
<223> OTHER INFORMATION: Humanized 13C5-IgG4 (F234A/L235A) antibody
heavy chain full length sequence

<400> SEQUENCE: 78

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Arg Ser Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Asp Cys Ala
                85                  90                  95

Arg Gly Tyr Asp Ser Gly Phe Ala Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Cys Ser Arg Ser Thr Ser Glu Ser Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Lys Thr Tyr Thr Cys Asn Val Asp His Lys Pro Ser Asn Thr
        195                 200                 205
```

Lys Val Asp Lys Arg Val Glu Ser Lys Tyr Gly Pro Pro Cys Pro
    210                 215                 220
Cys Pro Ala Pro Glu Ala Ala Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser Gln Glu Asp Pro Glu Val Gln Phe Asn
            260                 265                 270
Trp Tyr Val Asp Gly Val Glu Val His Asn Ala Lys Thr Lys Pro Arg
        275                 280                 285
Glu Glu Gln Phe Asn Ser Thr Tyr Arg Val Val Ser Val Leu Thr Val
    290                 295                 300
Leu His Gln Asp Trp Leu Asn Gly Lys Glu Tyr Lys Cys Lys Val Ser
305                 310                 315                 320
Asn Lys Gly Leu Pro Ser Ser Ile Glu Lys Thr Ile Ser Lys Ala Lys
                325                 330                 335
Gly Gln Pro Arg Glu Pro Gln Val Tyr Thr Leu Pro Pro Ser Gln Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Val Leu Asp Ser Asp Gly Ser Phe
385                 390                 395                 400
Phe Leu Tyr Ser Arg Leu Thr Val Asp Lys Ser Arg Trp Gln Glu Gly
                405                 410                 415
Asn Val Phe Ser Cys Ser Val Met His Glu Ala Leu His Asn His Tyr
            420                 425                 430
Thr Gln Lys Ser Leu Ser Leu Ser Leu Gly
        435                 440

<210> SEQ ID NO 79
<211> LENGTH: 657
<212> TYPE: DNA
<213> ORGANISM: Artificial Sequence
<220> FEATURE:
<223> OTHER INFORMATION: Humanized 13C5 antibody light chain full length
      sequence

<400> SEQUENCE: 79
gacattgtgc tgactcagag ccccgcttca ctggcagtgt ctccagggca gcgggcaacc      60
atcacatgca gagcctcaca gagcgtctcc accagctcct ctagtttcat gcactggtac     120
cagcagaagc ccggacagcc ccctaagctg ctgatcaaat atgctagcaa cctggagtcc     180
ggcgtgccag ccaggttctc tggcagtggg tcaggaaccg acttactct gaccattaat     240 cccgtcgaag ccaacgatac agctaattac tattgtcagc attcctggga gatcccttac     300
acatttggcc aggggactaa gctggagatc aagcgtacgg tggccgcacc aagcgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta gcctcagc     540 agcaccctga cgctgagcaa agcagactac gagaaacaca agtctacgc ctgcgaagtc     600 acccatcagg gcctgagctc gcccgtcaca aagagcttta cagaggcga gtgctga      657

```
<210> SEQ ID NO 80
<211> LENGTH: 218
<212> TYPE: PRT
<213> ORGANISM: Artificial Sequence
<220> FEATURE:
<223> OTHER INFORMATION: Humanized 13C5 antibody light chain full length
      sequence

<400> SEQUENCE: 80

Asp Ile Val Leu Thr Gln Ser Pro Ala Ser Leu Ala Val Ser Pro Gly
1               5                   10                  15

Gln Arg Ala Thr Ile Thr Cys Arg Ala Ser Gln Ser Val Ser Thr Ser
            20                  25                  30

Ser Ser Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Thr Ile Asn
65                  70                  75                  80

Pro Val Glu Ala Asn Asp Thr Ala Asn Tyr Tyr Cys Gln His Ser Trp
                85                  90                  95

Glu Ile Pro Tyr Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 81
<211> LENGTH: 5
<212> TYPE: PRT
<213> ORGANISM: Mus sp.

<400> SEQUENCE: 81

Ser Tyr Gly Met Ser
1               5

<210> SEQ ID NO 82
<211> LENGTH: 16
<212> TYPE: PRT
<213> ORGANISM: Mus sp.

<400> SEQUENCE: 82

Ser Ile Ser Ser Gly Gly Ser Thr Tyr Tyr Pro Asp Ser Val Lys Gly
1               5                   10                  15

<210> SEQ ID NO 83
<211> LENGTH: 8
<212> TYPE: PRT
```

```
<213> ORGANISM: Mus sp.

<400> SEQUENCE: 83

Gly Tyr Asp Ser Gly Phe Ala Tyr
1               5

<210> SEQ ID NO 84
<211> LENGTH: 15
<212> TYPE: PRT
<213> ORGANISM: Mus sp.

<400> SEQUENCE: 84

Arg Ala Ser Gln Ser Val Ser Thr Ser Ser Ser Ser Phe Met His
1               5                   10                  15

<210> SEQ ID NO 85
<211> LENGTH: 7
<212> TYPE: PRT
<213> ORGANISM: Mus sp.

<400> SEQUENCE: 85

Tyr Ala Ser Asn Leu Glu Ser
1               5

<210> SEQ ID NO 86
<211> LENGTH: 9
<212> TYPE: PRT
<213> ORGANISM: Mus sp.

<400> SEQUENCE: 86

Gln His Ser Trp Glu Ile Pro Tyr Thr
1               5

<210> SEQ ID NO 87
<211> LENGTH: 5
<212> TYPE: PRT
<213> ORGANISM: Mus sp.

<400> SEQUENCE: 87

Ser Tyr Gly Met Ser
1               5

<210> SEQ ID NO 88
<211> LENGTH: 16
<212> TYPE: PRT
<213> ORGANISM: Mus sp.

<400> SEQUENCE: 88

Ser Ile Ser Ser Gly Gly Thr Thr Tyr Tyr Pro Asp Ser Val Lys Gly
1               5                   10                  15

<210> SEQ ID NO 89
<211> LENGTH: 8
<212> TYPE: PRT
<213> ORGANISM: Mus sp.

<400> SEQUENCE: 89

Gly Tyr Asp Ser Gly Phe Ala Tyr
1               5

<210> SEQ ID NO 90
<211> LENGTH: 15
<212> TYPE: PRT
<213> ORGANISM: Mus sp.
```

```
<400> SEQUENCE: 90

Arg Ala Ser Gln Ser Val Ser Thr Ser Ser Ser Tyr Met His
1               5                   10                  15

<210> SEQ ID NO 91
<211> LENGTH: 7
<212> TYPE: PRT
<213> ORGANISM: Mus sp.

<400> SEQUENCE: 91

Tyr Ala Ser Asn Leu Glu Ser
1               5

<210> SEQ ID NO 92
<211> LENGTH: 9
<212> TYPE: PRT
<213> ORGANISM: Mus sp.

<400> SEQUENCE: 92

Gln His Ser Trp Glu Ile Pro Tyr Thr
1               5

<210> SEQ ID NO 93
<211> LENGTH: 5
<212> TYPE: PRT
<213> ORGANISM: Mus sp.

<400> SEQUENCE: 93

Thr Tyr Gly Val His
1               5

<210> SEQ ID NO 94
<211> LENGTH: 16
<212> TYPE: PRT
<213> ORGANISM: Mus sp.

<400> SEQUENCE: 94

Val Ile Trp Arg Gly Val Thr Thr Asp Tyr Asn Ala Ala Phe Met Ser
1               5                   10                  15

<210> SEQ ID NO 95
<211> LENGTH: 8
<212> TYPE: PRT
<213> ORGANISM: Mus sp.

<400> SEQUENCE: 95

Leu Gly Phe Tyr Ala Met Asp Tyr
1               5

<210> SEQ ID NO 96
<211> LENGTH: 11
<212> TYPE: PRT
<213> ORGANISM: Mus sp.

<400> SEQUENCE: 96

Lys Ala Ser Gln Ser Val Ser Asn Asp Val Ala
1               5                   10

<210> SEQ ID NO 97
<211> LENGTH: 7
<212> TYPE: PRT
<213> ORGANISM: Mus sp.

<400> SEQUENCE: 97
```

Tyr Ala Ala Asn Arg Tyr Thr
1               5

<210> SEQ ID NO 98
<211> LENGTH: 9
<212> TYPE: PRT
<213> ORGANISM: Mus sp.

<400> SEQUENCE: 98

Gln Gln Asp Tyr Thr Ser Pro Tyr Thr
1               5

<210> SEQ ID NO 99
<211> LENGTH: 5
<212> TYPE: PRT
<213> ORGANISM: Mus sp.

<400> SEQUENCE: 99

Ser Tyr Gly Val His
1               5

<210> SEQ ID NO 100
<211> LENGTH: 16
<212> TYPE: PRT
<213> ORGANISM: Mus sp.

<400> SEQUENCE: 100

Val Ile Trp Ser Gly Gly Val Thr Asp Tyr Asn Ala Ala Phe Ile Ser
1               5                   10                  15

<210> SEQ ID NO 101
<211> LENGTH: 8
<212> TYPE: PRT
<213> ORGANISM: Mus sp.

<400> SEQUENCE: 101

Leu Gly Phe Tyr Ala Met Asp Tyr
1               5

<210> SEQ ID NO 102
<211> LENGTH: 11
<212> TYPE: PRT
<213> ORGANISM: Mus sp.

<400> SEQUENCE: 102

Lys Ala Ser Gln Ser Val Ser Asn Asp Val Gly
1               5                   10

<210> SEQ ID NO 103
<211> LENGTH: 7
<212> TYPE: PRT
<213> ORGANISM: Mus sp.

<400> SEQUENCE: 103

Tyr Ala Ser Asn Arg Tyr Ser
1               5

<210> SEQ ID NO 104
<211> LENGTH: 9
<212> TYPE: PRT
<213> ORGANISM: Mus sp.

<400> SEQUENCE: 104

Gln Gln Asp Tyr Thr Ser Pro Tyr Thr
1               5

<210> SEQ ID NO 105
<211> LENGTH: 5
<212> TYPE: PRT
<213> ORGANISM: Mus sp.

<400> SEQUENCE: 105

Thr Tyr Trp Met His
1               5

<210> SEQ ID NO 106
<211> LENGTH: 17
<212> TYPE: PRT
<213> ORGANISM: Mus sp.

<400> SEQUENCE: 106

Gln Ile Asn Pro Asp Ser Thr Thr Ile Asn Tyr Ala Pro Ser Leu Lys
1               5                   10                  15

Asp

<210> SEQ ID NO 107
<211> LENGTH: 10
<212> TYPE: PRT
<213> ORGANISM: Mus sp.

<400> SEQUENCE: 107

Pro Gly Asp Tyr Gly Tyr Asp Phe Asp Cys
1               5                   10

<210> SEQ ID NO 108
<211> LENGTH: 16
<212> TYPE: PRT
<213> ORGANISM: Mus sp.

<400> SEQUENCE: 108

Arg Ser Ser Gln Ile Ile Val His Ser Asn Ala Asn Thr Tyr Leu Glu
1               5                   10                  15

<210> SEQ ID NO 109
<211> LENGTH: 7
<212> TYPE: PRT
<213> ORGANISM: Mus sp.

<400> SEQUENCE: 109

Lys Val Ser Asn Arg Phe Ser
1               5

<210> SEQ ID NO 110
<211> LENGTH: 9
<212> TYPE: PRT
<213> ORGANISM: Mus sp.

<400> SEQUENCE: 110

Phe Gln Gly Ser His Val Pro Tyr Thr
1               5

<210> SEQ ID NO 111
<211> LENGTH: 5
<212> TYPE: PRT
<213> ORGANISM: Mus sp.

<400> SEQUENCE: 111

Ser Gly Tyr Trp Asn
1               5

<210> SEQ ID NO 112
<211> LENGTH: 16
<212> TYPE: PRT
<213> ORGANISM: Mus sp.

<400> SEQUENCE: 112

Tyr Ile Ser Tyr Ser Gly Ser Thr Tyr Tyr Asn Pro Ser Leu Lys Ser
1               5                   10                  15

<210> SEQ ID NO 113
<211> LENGTH: 11
<212> TYPE: PRT
<213> ORGANISM: Mus sp.

<400> SEQUENCE: 113

Ser Leu Leu Trp Phe Ser Thr Gly Phe Ala Tyr
1               5                   10

<210> SEQ ID NO 114
<211> LENGTH: 12
<212> TYPE: PRT
<213> ORGANISM: Mus sp.

<400> SEQUENCE: 114

Ser Ala Ser Ser Ser Val Ser Ser Ser Tyr Leu Tyr
1               5                   10

<210> SEQ ID NO 115
<211> LENGTH: 7
<212> TYPE: PRT
<213> ORGANISM: Mus sp.

<400> SEQUENCE: 115

Asn Thr Ser Asn Leu Ala Ser
1               5

<210> SEQ ID NO 116
<211> LENGTH: 9
<212> TYPE: PRT
<213> ORGANISM: Mus sp.

<400> SEQUENCE: 116

His Gln Trp Arg Ser Tyr Pro Pro Thr
1               5

<210> SEQ ID NO 117
<211> LENGTH: 5
<212> TYPE: PRT
<213> ORGANISM: Mus sp.

<400> SEQUENCE: 117

Ser Tyr Gly Val His
1               5

<210> SEQ ID NO 118
<211> LENGTH: 16
<212> TYPE: PRT
<213> ORGANISM: Mus sp.

<400> SEQUENCE: 118

Val Ile Trp Ser Gly Gly Ile Thr Asp Tyr Asn Ala Ala Phe Lys Ser
1               5                   10                  15

-continued

<210> SEQ ID NO 119
<211> LENGTH: 8
<212> TYPE: PRT
<213> ORGANISM: Mus sp.

<400> SEQUENCE: 119

Leu Gly Phe Tyr Ala Met Asp Tyr
1               5

<210> SEQ ID NO 120
<211> LENGTH: 10
<212> TYPE: PRT
<213> ORGANISM: Mus sp.

<400> SEQUENCE: 120

Ser Ala Asn Ser Ser Val Ser Tyr Met His
1               5                   10

<210> SEQ ID NO 121
<211> LENGTH: 7
<212> TYPE: PRT
<213> ORGANISM: Mus sp.

<400> SEQUENCE: 121

Asp Thr Ser Lys Leu Ala Ser
1               5

<210> SEQ ID NO 122
<211> LENGTH: 9
<212> TYPE: PRT
<213> ORGANISM: Mus sp.

<400> SEQUENCE: 122

Gln Gln Trp Ser Ser Asn Pro Trp Thr
1               5

<210> SEQ ID NO 123
<211> LENGTH: 5
<212> TYPE: PRT
<213> ORGANISM: Mus sp.

<400> SEQUENCE: 123

Ser Tyr Gly Met Ser
1               5

<210> SEQ ID NO 124
<211> LENGTH: 16
<212> TYPE: PRT
<213> ORGANISM: Mus sp.

<400> SEQUENCE: 124

Ser Ile Ser Ser Gly Gly Thr Thr Tyr Tyr Leu Gly Ser Val Gln Gly
1               5                   10                  15

<210> SEQ ID NO 125
<211> LENGTH: 8
<212> TYPE: PRT
<213> ORGANISM: Mus sp.

<400> SEQUENCE: 125

Gly Tyr Asp Ala Gly Phe Ala Tyr
1               5

<210> SEQ ID NO 126
<211> LENGTH: 15

```
<212> TYPE: PRT
<213> ORGANISM: Mus sp.

<400> SEQUENCE: 126

Arg Ala Ser Gln Ser Val Ser Thr Ser Ser Tyr Ser Tyr Met His
1               5                   10                  15

<210> SEQ ID NO 127
<211> LENGTH: 7
<212> TYPE: PRT
<213> ORGANISM: Mus sp.

<400> SEQUENCE: 127

Tyr Ala Ser Asn Leu Glu Ser
1               5

<210> SEQ ID NO 128
<211> LENGTH: 9
<212> TYPE: PRT
<213> ORGANISM: Mus sp.

<400> SEQUENCE: 128

Gln Asn Ser Trp Glu Ile Pro Tyr Thr
1               5

<210> SEQ ID NO 129
<211> LENGTH: 5
<212> TYPE: PRT
<213> ORGANISM: Mus sp.

<400> SEQUENCE: 129

Ser Gly Tyr Trp Thr
1               5

<210> SEQ ID NO 130
<211> LENGTH: 16
<212> TYPE: PRT
<213> ORGANISM: Mus sp.

<400> SEQUENCE: 130

Tyr Ile Ser Tyr Thr Gly Ser Thr Tyr Tyr Asn Pro Ser Leu Lys Ser
1               5                   10                  15

<210> SEQ ID NO 131
<211> LENGTH: 9
<212> TYPE: PRT
<213> ORGANISM: Mus sp.

<400> SEQUENCE: 131

Gln Arg Asp Trp Leu Gly Phe Ala Tyr
1               5

<210> SEQ ID NO 132
<211> LENGTH: 17
<212> TYPE: PRT
<213> ORGANISM: Mus sp.

<400> SEQUENCE: 132

Lys Ser Ser Gln Ser Leu Leu Tyr Ser Ser Asn Gln Lys Asn Ser Leu
1               5                   10                  15
Ala

<210> SEQ ID NO 133
<211> LENGTH: 7
```

```
<212> TYPE: PRT
<213> ORGANISM: Mus sp.

<400> SEQUENCE: 133

Trp Ala Ser Asn Arg Glu Ser
1               5

<210> SEQ ID NO 134
<211> LENGTH: 9
<212> TYPE: PRT
<213> ORGANISM: Mus sp.

<400> SEQUENCE: 134

Gln Gln Tyr Tyr Ser Tyr Pro Leu Thr
1               5

<210> SEQ ID NO 135
<211> LENGTH: 5
<212> TYPE: PRT
<213> ORGANISM: Mus sp.

<400> SEQUENCE: 135

Ser Tyr Gly Met Ser
1               5

<210> SEQ ID NO 136
<211> LENGTH: 16
<212> TYPE: PRT
<213> ORGANISM: Mus sp.

<400> SEQUENCE: 136

Ser Ile Ser Ser Gly Gly Ser Ile Tyr Tyr Pro Asp Ser Val Lys Gly
1               5                   10                  15

<210> SEQ ID NO 137
<211> LENGTH: 8
<212> TYPE: PRT
<213> ORGANISM: Mus sp.

<400> SEQUENCE: 137

Gly Tyr Asp Ala Gly Phe Ala Phe
1               5

<210> SEQ ID NO 138
<211> LENGTH: 15
<212> TYPE: PRT
<213> ORGANISM: Mus sp.

<400> SEQUENCE: 138

Arg Ala Ser Gln Ser Val Ser Thr Ser Ser Tyr Ser Tyr Val His
1               5                   10                  15

<210> SEQ ID NO 139
<211> LENGTH: 7
<212> TYPE: PRT
<213> ORGANISM: Mus sp.

<400> SEQUENCE: 139

Tyr Ala Ser Asn Leu Glu Ser
1               5

<210> SEQ ID NO 140
<211> LENGTH: 9
<212> TYPE: PRT
<213> ORGANISM: Mus sp.
```

<400> SEQUENCE: 140

Gln His Ser Trp Glu Ile Pro Tyr Thr
1               5

<210> SEQ ID NO 141
<211> LENGTH: 660
<212> TYPE: DNA
<213> ORGANISM: Homo sapiens

<400> SEQUENCE: 141
tttactgtca cggttcccaa ggacctatat gtggtagagt atggtagcaa tatgacaatt     60
gaatgcaaat tcccagtaga aaacaattga gacctggctg cactaattgt ctattgggaa    120
atggaggata agaacattat tcaatttgtg catggagagg aagacctgaa ggttcagcat    180
agtagctaca gacagagggc ccggctgttg aaggaccagc tctccctggg aaatgctgca    240
cttcagatca cagatgtgaa attgcaggat gcagggggtgt accgctgcat gatcagctat    300
ggtggtgccg actacaagcg aattactgtg aaagtcaatg ccccatacaa caaaatcaac    360
caaagaattt tggttgtgga tccagtcacc tctgaacatg aactgacatg tcaggctgag    420
ggctacccca aggccgaagt catctggaca agcagtgacc atcaagtcct gagtggtaag    480
accaccacca ccaattccaa gagagaggag aagcttttca atgtgaccag cacactgaga    540
atcaacacaa caactaatga gattttctac tgcacttta ggagattaga tcctgaggaa    600
aaccatacag ctgaattggt catcccagaa ctacctctgg cacatcctcc aaatgaaagg    660

<210> SEQ ID NO 142
<211> LENGTH: 220
<212> TYPE: PRT
<213> ORGANISM: Homo sapiens

<400> SEQUENCE: 142

Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
                20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

```
Phe Arg Arg Leu Asp Pro Glu Glu Asn His Thr Ala Glu Leu Val Ile
            195                 200                 205

Pro Glu Leu Pro Leu Ala His Pro Pro Asn Glu Arg
    210                 215                 220
```

<210> SEQ ID NO 143
<211> LENGTH: 681
<212> TYPE: DNA
<213> ORGANISM: Homo sapiens

<400> SEQUENCE: 143

```
tttactgtca cggttcccaa ggacctatat gtggtagagt atggtagcaa tatgacaatt      60
gaatgcaaat tcccagtaga aaacaatta gacctggctg cactaattgt ctattgggaa     120
atggaggata gaacattat tcaatttgtg catggagagg aagacctgaa ggttcagcat     180
agtagctaca gacagagggc ccggctgttg aaggaccagc tctccctggg aaatgctgca     240
cttcagatca cagatgtgaa attgcaggat gcagggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagaggag aagcttttca atgtgaccag cacactgaga     540
atcaacacaa caactaatga dattttctac tgcacttta ggagattaga tcctgaggaa     600
aaccatacag ctgaattggt catcccagaa ctacctctgg cacatcctcc aaatgaaagg     660
catcatcacc accatcacta a                                              681
```

<210> SEQ ID NO 144
<211> LENGTH: 226
<212> TYPE: PRT
<213> ORGANISM: Homo sapiens

<400> SEQUENCE: 144

```
Phe Thr Val Thr Val Pro Lys Asp Leu Tyr Val Val Glu Tyr Gly Ser
1               5                  10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175
```

-continued

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg His His His His
    210                 215                 220

His His
225

<210> SEQ ID NO 145
<211> LENGTH: 1344
<212> TYPE: DNA
<213> ORGANISM: Artificial Sequence
<220> FEATURE:
<223> OTHER INFORMATION: Human PD-L1-mFc sequence

<400> SEQUENCE: 145
tttactgtca cggttcccaa ggacctatat gtggtagagt atggtagcaa tatgacaatt      60
gaatgcaaat tcccagtaga aaacaatta gacctggctg cactaattgt ctattgggaa     120
atggaggata gaacattat tcaatttgtg catggagagg aagacctgaa ggttcagcat     180
agtagctaca acagagggc ccggctgttg aaggaccagc tctccctggg aaatgctgca     240
cttcagatca cagatgtgaa attgcaggat gcagggtgt accgctgcat gatcagctat     300
ggtggtgccg actacaagcg aattactgtg aaagtcaatg ccccatacaa caaaatcaac     360
caaagaattt tggttgtgga tccagtcacc tctgaacatg aactgacatg tcaggctgag     420
ggctacccca aggccgaagt catctggaca agcagtgacc atcaagtcct gagtggtaag     480
accaccacca ccaattccaa gagagaggag aagcttttca atgtgaccag cacactgaga     540
atcaacacaa caactaatga dattttctac tgcactttta ggagattaga tcctgaggaa     600
aaccatacag ctgaattggt catcccagaa ctacctctgg cacatcctcc aaatgaaagg     660
ggtaccagat ctagaggctg caaaccctgt atctgcacag tgcccgaggt gagctccgtg     720 ttcatcttc cccccaagcc caaggacgtg ctgaccatca cactcacacc caaggtcacc     780
tgcgtggtcg tggacatctc caaggacgac cccgaagtcc agttcagctg gttcgtggac     840
gacgtggagg tgcacaccgc tcagacccaa cccagagagg agcagtttaa ctccaccttc     900
aggtccgtgt ccgagctccc catcatgcac caggactggc tgaatggcaa ggagttcaag     960
tgcagggtga actccgctgc tttccccgcc cccattgaga agaccatctc caagaccaag    1020
ggaaggccca aggcccccca ggtgtacacc attcccctc ccaaggagca gatggccaag    1080
gacaaggtgt ccctgacctg tatgatcacc gacttctttc ccgaggacat caccgtcgaa    1140
tggcagtgga acggcagcc cgccgagaac tataagaaca cccaacccat catggacacc    1200
gacggcagct acttcgtgta tagcaagctc aacgtgcaga gagcaactg ggaagccgga    1260 aataccttca cctgctccgt cctgcacgag ggcctgcaca accaccatac cgaaaagagc    1320
ctgagccaca gccccggaaa gtaa                                           1344

<210> SEQ ID NO 146
<211> LENGTH: 447
<212> TYPE: PRT
<213> ORGANISM: Artificial Sequence
<220> FEATURE:
<223> OTHER INFORMATION: Human PD-L1-mFc sequence

<400> SEQUENCE: 146

```
Phe Thr Val Thr Val Pro Lys Asp Leu Tyr Val Glu Tyr Gly Ser
 1               5                  10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
            35                  40                  45

Phe Val His Gly Glu Glu Asp Leu Lys Val Gln His Ser Ser Tyr Arg
        50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
            115                 120                 125

Val Thr Ser Glu His Glu Leu Thr Cys Gln Ala Glu Gly Tyr Pro Lys
        130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Asn Glu Ile Phe Tyr Cys Thr
            180                 185                 190

Phe Arg Arg Leu Asp Pro Glu Glu Asn His Thr Ala Glu Leu Val Ile
            195                 200                 205

Pro Glu Leu Pro Leu Ala His Pro Pro Asn Glu Arg Gly Thr Arg Ser
210                 215                 220

Arg Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
            260                 265                 270

Val Gln Phe Ser Trp Phe Val Asp Asp Val Glu Val His Thr Ala Gln
        275                 280                 285

Thr Gln Pro Arg Glu Glu Gln Phe Asn Ser Thr Phe Arg Ser Val Ser
    290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
            340                 345                 350

Pro Pro Lys Glu Gln Met Ala Lys Asp Lys Val Ser Leu Thr Cys Met
        355                 360                 365

Ile Thr Asp Phe Phe Pro Glu Asp Ile Thr Val Glu Trp Gln Trp Asn
    370                 375                 380

Gly Gln Pro Ala Glu Asn Tyr Lys Asn Thr Gln Pro Ile Met Asp Thr
385                 390                 395                 400

Asp Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
```

```
                  420                425                430
His Asn His His Thr Glu Lys Ser Leu Ser His Ser Pro Gly Lys
         435                440                445
```

<210> SEQ ID NO 147
<211> LENGTH: 1374
<212> TYPE: DNA
<213> ORGANISM: Artificial Sequence
<220> FEATURE:
<223> OTHER INFORMATION: Human PD-L1-hFc sequence

<400> SEQUENCE: 147

| | | | | | |
|---|---|---|---|---|---|
| tttactgtca | cggttcccaa | ggacctatat | gtggtagagt | atggtagcaa | tatgacaatt | 60 |
| gaatgcaaat | tcccagtaga | aaaacaatta | gacctggctg | cactaattgt | ctattgggaa | 120 |
| atggaggata | agaacattat | tcaatttgtg | catggagagg | aagacctgaa | ggttcagcat | 180 |
| agtagctaca | gacagagggc | ccggctgttg | aaggaccagc | tctccctggg | aaatgctgca | 240 |
| cttcagatca | cagatgtgaa | attgcaggat | gcagggtgt | accgctgcat | gatcagctat | 300 |
| ggtggtgccg | actacaagcg | aattactgtg | aaagtcaatg | ccccatacaa | caaaatcaac | 360 |
| caaagaattt | tggttgtgga | tccagtcacc | tctgaacatg | aactgacatg | tcaggctgag | 420 |
| ggctacccca | aggccgaagt | catctggaca | agcagtgacc | atcaagtcct | gagtggtaag | 480 |
| accaccacca | ccaattccaa | gagagaggag | aagcttttca | atgtgaccag | cacactgaga | 540 |
| atcaacacaa | caactaatga | gattttctac | tgcacttta | ggagattaga | tcctgaggaa | 600 |
| aaccatacag | ctgaattggt | catcccagaa | ctacctctgg | cacatcctcc | aaatgaaagg | 660 |
| ggtaccagat | ctagagagcc | caaatcttct | gacaaaactc | acacatgccc | accgtgccca | 720 |
| gcacctgaat | cgagggtgc | accgtcagtc | ttcctcttcc | ccccaaaacc | caaggacacc | 780 |
| ctcatgatct | cccggactcc | tgaggtcaca | tgcgtggtgg | tggacgtaag | ccacgaagac | 840 |
| cctgaggtca | agttcaactg | gtacgtggac | ggcgtggagg | tgcataatgc | caagacaaag | 900 |
| ccgcgggagg | agcagtacaa | cagcacgtac | cgtgtggtca | gcgtcctcac | cgtcctgcac | 960 |
| caggactggc | tgaatggcaa | ggagtacaag | tgcaaggtct | ccaacaaagc | cctcccaacc | 1020 |
| cccatcgaga | aaaccatctc | caaagccaaa | gggcagcccc | gagaaccaca | ggtgtacacc | 1080 |
| ctgcccccat | cccgggatga | gctgaccaag | aaccaggtca | gcctgacctg | cctggtcaaa | 1140 |
| ggcttctatc | caagcgacat | cgccgtggag | tgggagagca | atgggcagcc | ggagaacaac | 1200 |
| tacaagacca | cgcctcccgt | gctggactcc | gacggctcct | tcttcctcta | cagcaagctc | 1260 |
| accgtggaca | agagcaggtg | gcagcagggg | aacgtcttct | catgctccgt | gatgcatgag | 1320 |
| gctctgcaca | accactacac | gcagaagagc | ctctccctgt | ctccgggtaa | atga | 1374 |

<210> SEQ ID NO 148
<211> LENGTH: 457
<212> TYPE: PRT
<213> ORGANISM: Artificial Sequence
<220> FEATURE:
<223> OTHER INFORMATION: Human PD-L1-hFc sequence

<400> SEQUENCE: 148

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45
```

-continued

```
Phe Val His Gly Glu Glu Asp Leu Lys Val Gln His Ser Ser Tyr Arg
 50                  55                  60

Gln Arg Ala Arg Leu Leu Lys Asp Gln Leu Ser Leu Gly Asn Ala Ala
 65                  70                  75                  80

Leu Gln Ile Thr Asp Val Lys Leu Gln Asp Ala Gly Val Tyr Arg Cys
                 85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
        195                 200                 205

Pro Glu Leu Pro Leu Ala His Pro Pro Asn Glu Arg Gly Thr Arg Ser
210                 215                 220

Arg Glu Pro Lys Ser Ser Asp Lys Thr His Thr Cys Pro Pro Cys Pro
225                 230                 235                 240

Ala Pro Glu Phe Glu Gly Ala Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Thr Pro Ile Glu Lys Thr Ile Ser Lys Ala Lys Gly Gln
            340                 345                 350

Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
450                 455
```

<210> SEQ ID NO 149
<211> LENGTH: 681
<212> TYPE: DNA
<213> ORGANISM: Artificial Sequence
<220> FEATURE:
<223> OTHER INFORMATION: Cyno-PD-L1-HisTag

<400> SEQUENCE: 149

```
tttactgtca cggttcccaa ggacctatat gtggtagagt atggcagcaa tatgacaatt      60
gaatgcaaat tcccagtaga aaacaatta gacctgactt cactaattgt ctattgggaa     120
atggaggata agaacattat tcaatttgtg catggagagg aagacctgaa ggttcagcat     180
agtaactaca gacagagggc ccagctgttg aaggaccagc tctccctggg aaatgctgca     240
cttcggatca cagatgtgaa attgcaggat gcaggggttt accgctgcat gatcagctat     300
ggtggtgccg actacaagcg gattaccgtg aaagtcaatg ctccatacaa caaaatcaac     360
caaagaattt tggttgtcga tccagtcacc tctgaacatg aactaacatg tcaggctgag     420
ggctaccca aggccgaagt catttggaca agcagtgacc atcaagtcct gagtggtaag     480
accaccacca ccaattccaa gagagaggag aagcttttaa atgtgaccag cacactgaga     540
atcaacacaa cagctaatga gattttctac tgcattttta ggagattaga tcctgaggaa     600
aaccatacag ctgaattggt catcccagaa ctacctctgg cgcttcctcc aaatgaaagg     660
catcatcacc accatcacta a                                              681
```

<210> SEQ ID NO 150
<211> LENGTH: 226
<212> TYPE: PRT
<213> ORGANISM: Artificial Sequence
<220> FEATURE:
<223> OTHER INFORMATION: Cyno-PD-L1-HisTag

<400> SEQUENCE: 150

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Thr Ser Leu Ile Val Tyr Trp Glu Met Glu Asp Lys Asn Ile Ile Gln
        35                  40                  45

Phe Val His Gly Glu Glu Asp Leu Lys Val Gln His Ser Asn Tyr Arg
    50                  55                  60

Gln Arg Ala Gln Leu Leu Lys Asp Gln Leu Ser Leu Gly Asn Ala Ala
65                  70                  75                  80

Leu Arg Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
    130                 135                 140

Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Leu Asn Val Thr
                165                 170                 175

Ser Thr Leu Arg Ile Asn Thr Thr Ala Asn Glu Ile Phe Tyr Cys Ile
            180                 185                 190
```

```
Phe Arg Arg Leu Asp Pro Glu Glu Asn His Thr Ala Glu Leu Val Ile
        195                 200                 205

Pro Glu Leu Pro Leu Ala Leu Pro Pro Asn Glu Arg His His His His
    210                 215                 220

His His
225

<210> SEQ ID NO 151
<211> LENGTH: 450
<212> TYPE: DNA
<213> ORGANISM: Homo sapiens

<400> SEQUENCE: 151
ccaggatggt tcttagactc cccagacagg ccctggaacc cccccacctt ctccccagcc      60
ctgctcgtgg tgaccgaagg ggacaacgcc accttcacct gcagcttctc caacacatcg    120
gagagcttcg tgctaaactg gtaccgcatg agccccagca accagacgga caagctggcc    180
gccttccccg aggaccgcag ccagcccggc caggactgcc gcttccgtgt cacacaactg    240
cccaacgggc gtgacttcca catgagcgtg gtcagggccc ggcgcaatga cagcggcacc    300
tacctctgtg gggccatctc cctggccccc aaggcgcaga tcaaagagag cctgcgggca    360
gagctcaggg tgacagagag aagggcagaa gtgcccacag cccaccccag cccctcaccc    420
aggccagccg gccagttcca aaccctggtg                                      450

<210> SEQ ID NO 152
<211> LENGTH: 150
<212> TYPE: PRT
<213> ORGANISM: Homo sapiens

<400> SEQUENCE: 152

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val
145                 150

<210> SEQ ID NO 153
<211> LENGTH: 1134
<212> TYPE: DNA
<213> ORGANISM: Artificial Sequence
<220> FEATURE:
<223> OTHER INFORMATION: Human PD-1-mFc sequence
```

<400> SEQUENCE: 153

```
ccaggatggt tcttagactc cccagacagg ccctggaacc ccccacctt ctccccagcc      60
ctgctcgtgg tgaccgaagg ggacaacgcc accttcacct gcagcttctc caacacatcg    120
gagagcttcg tgctaaactg gtaccgcatg agccccagca accagacgga caagctggcc    180
gccttccccg aggaccgcag ccagcccggc caggactgcc gcttccgtgt cacacaactg    240
cccaacgggc gtgacttcca catgagcgtg gtcaggaccc ggcgcaatga cagcggcacc    300
tacctctgtg gggccatctc cctggccccc aaggcgcaga tcaaagagag cctgcgggca    360
gagctcaggg tgacagagag aagggcagaa gtgcccacag cccaccccag ccctcacccc    420
aggccagccg gccagttcca aaccctggtg gtaccagat ctagaggctg caaaccctgt     480
atctgcacag tgcccgaggt gagctccgtg ttcatctttc ccccaagcc caaggacgtg     540
ctgaccatca cactcacacc caaggtcacc tgcgtggtcg tggacatctc caaggacgac    600
cccgaagtcc agttcagctg gttcgtggac gacgtggagg tgcacaccgc tcagacccaa    660
cccagagagg agcagtttaa ctccaccttc aggtccgtgt ccgagctccc catcatgcac    720
caggactggc tgaatggcaa ggagttcaag tgcagggtga actccgctgc tttccccgcc    780
cccattgaga agaccatctc caagaccaag ggaaggccca aggccccca ggtgtacacc     840
attccccctc caaggagca gatggccaag gacaaggtgt ccctgacctg tatgatcacc    900
gacttctttc ccgaggacat caccgtcgaa tggcagtgga acggccagcc cgccgagaac    960
tataagaaca cccaacccat catggacacc gacggcagct acttcgtgta tagcaagctc   1020
aacgtgcaga agagcaactg ggaagccgga aataccttca cctgctccgt cctgcacgag   1080
ggcctgcaca accaccatac cgaaaagagc ctgagccaca gccccggaaa gtaa         1134
```

<210> SEQ ID NO 154
<211> LENGTH: 377
<212> TYPE: PRT
<213> ORGANISM: Artificial Sequence
<220> FEATURE:
<223> OTHER INFORMATION: Human PD-1-mFc sequence

<400> SEQUENCE: 154

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Thr Arg Ser Arg Gly Cys Lys Pro Cys
```

```
                145                 150                 155                 160
        Ile Cys Thr Val Pro Glu Val Ser Ser Val Phe Ile Phe Pro Pro Lys
                        165                 170                 175

Pro Lys Asp Val Leu Thr Ile Thr Leu Thr Pro Lys Val Thr Cys Val
                        180                 185                 190

Val Val Asp Ile Ser Lys Asp Asp Pro Glu Val Gln Phe Ser Trp Phe
                        195                 200                 205

Val Asp Asp Val Glu Val His Thr Ala Gln Thr Gln Pro Arg Glu Glu
                        210                 215                 220

Gln Phe Asn Ser Thr Phe Arg Ser Val Ser Glu Leu Pro Ile Met His
        225                 230                 235                 240

Gln Asp Trp Leu Asn Gly Lys Glu Phe Lys Cys Arg Val Asn Ser Ala
                        245                 250                 255

Ala Phe Pro Ala Pro Ile Glu Lys Thr Ile Ser Lys Thr Lys Gly Arg
                        260                 265                 270

Pro Lys Ala Pro Gln Val Tyr Thr Ile Pro Pro Lys Glu Gln Met
                        275                 280                 285

Ala Lys Asp Lys Val Ser Leu Thr Cys Met Ile Thr Asp Phe Phe Pro
        290                 295                 300

Glu Asp Ile Thr Val Glu Trp Gln Trp Asn Gly Gln Pro Ala Glu Asn
        305                 310                 315                 320

Tyr Lys Asn Thr Gln Pro Ile Met Asp Thr Asp Gly Ser Tyr Phe Val
                        325                 330                 335

Tyr Ser Lys Leu Asn Val Gln Lys Ser Asn Trp Glu Ala Gly Asn Thr
                        340                 345                 350

Phe Thr Cys Ser Val Leu His Glu Gly Leu His Asn His His Thr Glu
                        355                 360                 365

Lys Ser Leu Ser His Ser Pro Gly Lys
                        370                 375

<210> SEQ ID NO 155
<211> LENGTH: 1164
<212> TYPE: DNA
<213> ORGANISM: Artificial Sequence
<220> FEATURE:
<223> OTHER INFORMATION: Human PD-1-hFc sequence

<400> SEQUENCE: 155
ccaggatggt tcttagactc cccagacagg ccctggaacc cccccacctt ctccccagcc    60
ctgctcgtgg tgaccgaagg ggacaacgcc accttcacct gcagcttctc caacacatcg   120
gagagcttcg tgctaaactg gtaccgcatg agccccagca accagacgga caagctggcc   180
gccttccccg aggaccgcag ccagcccggc caggactgcc gcttccgtgt cacacaactg   240
cccaacgggc gtgacttcca catgagcgtg gtcagggccc ggcgcaatga cagcggcacc   300
tacctctgtg gggccatctc cctggccccc aaggcgcaga tcaaagagag cctgcgggca   360
gagctcaggg tgacagagag aagggcagaa gtgcccacag cccaccccag ccctcaccc    420 aggccagccg gccagttcca aaccctggtg gtaccagat ctagagagcc caaatcttct   480
gacaaaactc acacatgccc accgtgccca gcacctgaat cgagggtgc accgtcagtc    540 ttcctcttcc cccaaaaacc caaggacacc ctcatgatct cccggactcc tgaggtcaca    600
tgcgtggtgg tggacgtaag ccacgaagac cctgaggtca agttcaactg gtacgtggac    660
ggcgtggagg tgcataatgc caagacaaag ccgcgggagg agcagtacaa cagcacgtac    720
cgtgtggtca gcgtcctcac cgtcctgcac caggactggc tgaatggcaa ggagtacaag    780
```

```
tgcaaggtct ccaacaaagc cctcccaacc cccatcgaga aaaccatctc caaagccaaa      840
gggcagcccc gagaaccaca ggtgtacacc ctgcccccat cccgggatga gctgaccaag      900
aaccaggtca gcctgacctg cctggtcaaa ggcttctatc caagcgacat cgccgtggag      960
tgggagagca atgggcagcc ggagaacaac tacaagacca cgcctcccgt gctggactcc     1020
gacggctcct tcttcctcta cagcaagctc accgtggaca agagcaggtg gcagcagggg     1080
aacgtcttct catgctccgt gatgcatgag gctctgcaca accactacac gcagaagagc     1140
ctctccctgt ctccgggtaa atga                                            1164
```

<210> SEQ ID NO 156
<211> LENGTH: 222
<212> TYPE: PRT
<213> ORGANISM: Artificial Sequence
<220> FEATURE:
<223> OTHER INFORMATION: Human PD-1-hFc sequence

<400> SEQUENCE: 156

```
Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His Pro Ser Pro Ser Pro Arg Pro Ala Gly
    130                 135                 140

Gln Phe Gln Thr Leu Val Gly Thr Arg Ser Arg Glu Pro Lys Ser Ser
145                 150                 155                 160

Asp Lys Thr His Thr Cys Pro Pro Cys Pro Ala Pro Glu Phe Glu Gly
                165                 170                 175

Ala Pro Ser Val Phe Leu Phe Pro Pro Lys Pro Lys Asp Thr Leu Met
            180                 185                 190

Ile Ser Arg Thr Pro Glu Val Thr Cys Val Val Val Asp Val Ser His
        195                 200                 205

Glu Asp Pro Glu Val Lys Phe Asn Trp Tyr Val Asp Gly Val
    210                 215                 220
```